(12) United States Patent
Hammond et al.

(10) Patent No.: US 11,590,030 B2
(45) Date of Patent: Feb. 28, 2023

(54) WOUND CLOSURE DEVICE WITH PROTECTIVE LAYER AND METHOD OF USE

(71) Applicant: Smith & Nephew PLC, Watford (GB)

(72) Inventors: Victoria Jody Hammond, Hull (GB); Neill John Rawson, Doncaster (GB); Iain Webster, Hull (GB)

(73) Assignee: Smith & Nephew PLC, Watford (GB)

( * ) Notice: Subject to any disclaimer, the term of this patent is extended or adjusted under 35 U.S.C. 154(b) by 0 days.

(21) Appl. No.: 16/637,258

(22) PCT Filed: Aug. 3, 2018

(86) PCT No.: PCT/EP2018/071116
§ 371 (c)(1),
(2) Date: Feb. 6, 2020

(87) PCT Pub. No.: WO2019/030136
PCT Pub. Date: Feb. 14, 2019

(65) Prior Publication Data
US 2020/0237564 A1 Jul. 30, 2020

Related U.S. Application Data

(60) Provisional application No. 62/541,978, filed on Aug. 7, 2017.

(51) Int. Cl.
*A61F 13/02* (2006.01)
*A61F 13/00* (2006.01)
*A61M 1/00* (2006.01)

(52) U.S. Cl.
CPC .... *A61F 13/0216* (2013.01); *A61F 13/00068* (2013.01); *A61M 1/90* (2021.05);
(Continued)

(58) Field of Classification Search
CPC . A61M 1/90; A61M 1/0088; A61F 13/00068; A61F 2013/00182;
(Continued)

(56) References Cited

U.S. PATENT DOCUMENTS 2,245,909 A 6/1941 Helen et al.
3,014,483 A 12/1961 Frank et al.
(Continued)

FOREIGN PATENT DOCUMENTS

AU 2012261793 B2 11/2014
AU 2013206230 B2 5/2016
(Continued)

OTHER PUBLICATIONS

International Preliminary Report on Patentability for Application No. PCT/EP2018/071116, dated Feb. 20, 2020, 10 pages.
(Continued)

*Primary Examiner* — Adam Marcetich
*Assistant Examiner* — Nhu Q. Tran
(74) *Attorney, Agent, or Firm* — Knobbe, Martens Olson & Bear LLP

(57) ABSTRACT

A negative pressure wound closure system and methods for using such a system are described. Preferred embodiments of the invention facilitate closure of the wound by utilizing a stabilizing structure that preferentially contracts to provide for movement of the tissue. Some embodiments may utilize a protective layer, such as a mesh or net layer, attached to a top surface of the stabilizing structure. The protective layer prevents a drape positioned over the stabilizing structure from being drawn into cells of the stabilizing structure, and permits visualization of the collapse of the cells.

28 Claims, 42 Drawing Sheets

(52) U.S. Cl.
CPC ........... *A61F 2013/00225* (2013.01); *A61F 2013/00634* (2013.01); *A61M 2210/1021* (2013.01)

(58) Field of Classification Search
CPC ............ A61F 13/00029; A61F 13/0206; A61F 13/00059; A61F 13/0209; A61F 13/022
See application file for complete search history.

(56) References Cited

U.S. PATENT DOCUMENTS

| | | |
|---|---|---|
| 3,164,152 A | 1/1965 | Vere et al. |
| 3,186,405 A | 6/1965 | Bailey et al. |
| 3,194,239 A | 7/1965 | Sullivan et al. |
| 3,578,003 A | 5/1971 | Everett |
| 3,789,851 A | 2/1974 | Leveen |
| 3,812,616 A | 5/1974 | Koziol |
| 4,467,805 A | 8/1984 | Fukuda |
| 4,608,041 A | 8/1986 | Nielsen |
| 4,699,134 A | 10/1987 | Samuelsen |
| 4,815,468 A | 3/1989 | Annand |
| 5,176,663 A | 1/1993 | Svedman et al. |
| 5,264,218 A | 11/1993 | Rogozinski |
| 5,376,067 A | 12/1994 | Daneshvar |
| 5,409,472 A | 4/1995 | Rawlings et al. |
| 5,415,715 A | 5/1995 | Delage et al. |
| 5,423,857 A | 6/1995 | Rosenman et al. |
| 5,512,041 A | 4/1996 | Bogart |
| 5,562,107 A | 10/1996 | Lavender et al. |
| 5,584,859 A | 12/1996 | Brotz |
| 5,636,643 A | 6/1997 | Argenta et al. |
| 5,695,777 A | 12/1997 | Donovan et al. |
| 5,810,750 A | 9/1998 | Buser |
| 6,176,868 B1 | 1/2001 | Detour |
| 6,503,208 B1 | 1/2003 | Skovlund |
| 6,548,727 B1 | 4/2003 | Swenson |
| 6,566,575 B1 | 5/2003 | Stickels et al. |
| 6,685,681 B2 | 2/2004 | Lockwood et al. |
| 6,712,839 B1 | 3/2004 | Lonne |
| 6,770,794 B2 | 8/2004 | Fleischmann |
| 6,787,682 B2 | 9/2004 | Gilman |
| 6,883,531 B1 | 4/2005 | Perttu |
| 6,977,323 B1 | 12/2005 | Swenson |
| 7,004,915 B2 | 2/2006 | Boynton et al. |
| 7,144,390 B1 | 12/2006 | Hannigan et al. |
| 7,315,183 B2 | 1/2008 | Hinterscher |
| 7,351,250 B2 | 4/2008 | Zamierowski |
| 7,361,184 B2 | 4/2008 | Joshi |
| 7,438,705 B2 | 10/2008 | Karpowicz et al. |
| 7,494,482 B2 | 2/2009 | Orgill et al. |
| 7,615,036 B2 | 11/2009 | Joshi et al. |
| 7,622,629 B2 | 11/2009 | Aali |
| 7,625,362 B2 | 12/2009 | Boehringer et al. |
| 7,683,667 B2 | 3/2010 | Kim |
| 7,700,819 B2 | 4/2010 | Ambrosio et al. |
| 7,754,937 B2 | 7/2010 | Boehringer et al. |
| 7,779,625 B2 | 8/2010 | Joshi et al. |
| 7,815,616 B2 | 10/2010 | Boehringer et al. |
| 7,857,806 B2 | 12/2010 | Karpowicz et al. |
| 7,863,495 B2 | 1/2011 | Aali |
| 7,892,181 B2 | 2/2011 | Christensen et al. |
| 7,896,856 B2 | 3/2011 | Petrosenko et al. |
| 7,909,805 B2 | 3/2011 | Weston |
| 7,910,789 B2 | 3/2011 | Sinyagin |
| 7,931,774 B2 | 4/2011 | Hall et al. |
| 7,942,866 B2 | 5/2011 | Radl et al. |
| 7,951,124 B2 | 5/2011 | Boehringer et al. |
| 7,964,766 B2 | 6/2011 | Blott et al. |
| 7,976,519 B2 | 7/2011 | Bubb et al. |
| 7,976,524 B2 | 7/2011 | Kudo et al. |
| 8,030,534 B2 | 10/2011 | Radl et al. |
| 8,057,447 B2 | 11/2011 | Olson et al. |
| 8,062,331 B2 | 11/2011 | Zamierowski |
| 8,067,662 B2 | 11/2011 | Aali et al. |
| 8,070,773 B2 | 12/2011 | Zamierowski |
| 8,114,126 B2 | 2/2012 | Heaton et al. |
| 8,123,781 B2 | 2/2012 | Zamierowski |
| 8,142,419 B2 | 3/2012 | Heaton et al. |
| 8,172,816 B2 | 5/2012 | Kazala et al. |
| 8,187,237 B2 | 5/2012 | Seegert |
| 8,188,331 B2 | 5/2012 | Barta et al. |
| 8,197,467 B2 | 6/2012 | Heaton et al. |
| 8,207,392 B2 | 6/2012 | Haggstrom et al. |
| 8,235,955 B2 | 8/2012 | Blott et al. |
| 8,246,590 B2 | 8/2012 | Hu et al. |
| 8,246,606 B2 | 8/2012 | Stevenson et al. |
| 8,257,328 B2 | 9/2012 | Augustine et al. |
| 8,273,105 B2 | 9/2012 | Cohen et al. |
| 8,328,776 B2 | 12/2012 | Kelch et al. |
| 8,337,411 B2 | 12/2012 | Nishtala et al. |
| 8,353,931 B2 | 1/2013 | Stopek et al. |
| 8,357,131 B2 | 1/2013 | Olson |
| 8,376,972 B2 | 2/2013 | Fleischmann |
| 8,430,867 B2 | 4/2013 | Robinson et al. |
| 8,447,375 B2 | 5/2013 | Shuler |
| 8,454,990 B2 | 6/2013 | Canada et al. |
| 8,460,257 B2 | 6/2013 | Locke et al. |
| 8,481,804 B2 | 7/2013 | Timothy |
| 8,486,032 B2 | 7/2013 | Seegert et al. |
| 8,500,776 B2 | 8/2013 | Ebner |
| 8,608,776 B2 | 12/2013 | Coward et al. |
| 8,632,523 B2 | 1/2014 | Eriksson et al. |
| 8,673,992 B2 | 3/2014 | Eckstein et al. |
| 8,679,080 B2 | 3/2014 | Kazala et al. |
| 8,679,153 B2 | 3/2014 | Dennis |
| 8,680,360 B2 | 3/2014 | Greener et al. |
| 8,708,984 B2 | 4/2014 | Robinson et al. |
| 8,721,629 B2 | 5/2014 | Hardman et al. |
| 8,746,662 B2 | 6/2014 | Poppe |
| 8,764,732 B2 | 7/2014 | Hartwell |
| 8,791,315 B2 | 7/2014 | Lattimore et al. |
| 8,791,316 B2 | 7/2014 | Greener |
| 8,802,916 B2 | 8/2014 | Griffey et al. |
| 8,821,535 B2 | 9/2014 | Greener |
| 8,945,030 B2 | 2/2015 | Weston |
| 9,039,783 B2 | 5/2015 | Petter-Puchner et al. |
| 9,044,579 B2 | 6/2015 | Blott et al. |
| 9,061,095 B2 | 6/2015 | Adie et al. |
| 9,180,231 B2 | 11/2015 | Greener |
| 9,408,755 B2 | 8/2016 | Larsson |
| 9,421,132 B2 | 8/2016 | Dunn |
| 9,610,390 B2 | 4/2017 | Weston |
| 9,655,807 B2 | 5/2017 | Locke et al. |
| 9,801,986 B2 | 10/2017 | Greener |
| 9,849,023 B2 | 12/2017 | Hall et al. |
| 10,143,485 B2 | 12/2018 | Locke et al. |
| 10,695,472 B2 | 6/2020 | Greener |
| 11,058,807 B2 | 7/2021 | Weston |
| 2001/0034499 A1 | 10/2001 | Sessions et al. |
| 2002/0077661 A1 | 6/2002 | Saadat |
| 2002/0161346 A1 | 10/2002 | Lockwood et al. |
| 2004/0162512 A1 | 8/2004 | Liedtke et al. |
| 2004/0267312 A1 | 12/2004 | Kanner et al. |
| 2005/0142331 A1 | 6/2005 | Anderson et al. |
| 2005/0267424 A1 | 12/2005 | Eriksson et al. |
| 2006/0020269 A1 | 1/2006 | Cheng |
| 2006/0058842 A1 | 3/2006 | Wilke et al. |
| 2006/0069357 A1 | 3/2006 | Marasco |
| 2006/0155260 A1 | 7/2006 | Blott et al. |
| 2006/0217795 A1 | 9/2006 | Besselink et al. |
| 2006/0271018 A1 | 11/2006 | Korf |
| 2007/0052144 A1 | 3/2007 | Knirck et al. |
| 2007/0104941 A1 | 5/2007 | Kameda et al. |
| 2007/0118096 A1 | 5/2007 | Smith et al. |
| 2007/0123973 A1 | 5/2007 | Roth et al. |
| 2007/0129660 A1 | 6/2007 | McLeod et al. |
| 2007/0149910 A1 | 6/2007 | Zocher |
| 2007/0185463 A1 | 8/2007 | Mulligan |
| 2007/0213597 A1 | 9/2007 | Wooster |
| 2007/0282309 A1 | 12/2007 | Bengtson et al. |
| 2008/0041401 A1 | 2/2008 | Casola et al. |
| 2008/0108977 A1 | 5/2008 | Heaton et al. |
| 2008/0243096 A1 | 10/2008 | Svedman |
| 2008/0275409 A1 | 11/2008 | Kane et al. |

(56) References Cited

U.S. PATENT DOCUMENTS

| | | |
|---|---|---|
| 2008/0306456 A1 | 12/2008 | Riesinger |
| 2009/0005716 A1 | 1/2009 | Abuzaina et al. |
| 2009/0099519 A1 | 4/2009 | Kaplan |
| 2009/0105670 A1 | 4/2009 | Bentley et al. |
| 2009/0204423 A1 | 8/2009 | Degheest et al. |
| 2009/0299308 A1 | 12/2009 | Kazala, Jr. et al. |
| 2009/0312685 A1 | 12/2009 | Olsen et al. |
| 2010/0022990 A1 | 1/2010 | Karpowicz et al. |
| 2010/0047324 A1 | 2/2010 | Fritz et al. |
| 2010/0081983 A1 | 4/2010 | Zocher et al. |
| 2010/0137775 A1 | 6/2010 | Hu et al. |
| 2010/0150991 A1 | 6/2010 | Bernstein |
| 2010/0160874 A1 | 6/2010 | Robinson et al. |
| 2010/0179515 A1 | 7/2010 | Swain et al. |
| 2010/0198128 A1 | 8/2010 | Turnlund et al. |
| 2010/0262106 A1 | 10/2010 | Hartwell |
| 2010/0280468 A1 | 11/2010 | Haggstrom et al. |
| 2010/0312159 A1 | 12/2010 | Aali et al. |
| 2011/0021965 A1 | 1/2011 | Karp et al. |
| 2011/0022082 A1 | 1/2011 | Burke et al. |
| 2011/0059291 A1 | 3/2011 | Boyce et al. |
| 2011/0066096 A1 | 3/2011 | Svedman |
| 2011/0082480 A1 | 4/2011 | Viola |
| 2011/0110996 A1 | 5/2011 | Schoenberger et al. |
| 2011/0112458 A1 | 5/2011 | Holm et al. |
| 2011/0178451 A1 | 7/2011 | Robinson et al. |
| 2011/0213319 A1 | 9/2011 | Blott et al. |
| 2011/0224631 A1 | 9/2011 | Simmons et al. |
| 2011/0224632 A1 | 9/2011 | Zimnitsky et al. |
| 2011/0224634 A1 | 9/2011 | Locke et al. |
| 2011/0264138 A1 | 10/2011 | Avelar et al. |
| 2011/0270301 A1 | 11/2011 | Cornet et al. |
| 2011/0305736 A1 | 12/2011 | Wieland et al. |
| 2012/0016321 A1 | 1/2012 | Wu et al. |
| 2012/0029455 A1 | 2/2012 | Perez-Foullerat et al. |
| 2012/0059412 A1 | 3/2012 | Fleischmann |
| 2012/0090699 A1 | 4/2012 | Lau |
| 2012/0130327 A1 | 5/2012 | Marquez |
| 2012/0136326 A1 | 5/2012 | Croizat et al. |
| 2012/0136328 A1 | 5/2012 | Johannison et al. |
| 2012/0143113 A1 | 6/2012 | Robinson et al. |
| 2012/0172926 A1 | 7/2012 | Hotter |
| 2012/0191132 A1 | 7/2012 | Sargeant |
| 2012/0209226 A1 | 8/2012 | Simmons et al. |
| 2012/0209227 A1 | 8/2012 | Dunn |
| 2012/0238931 A1 | 9/2012 | Rastegar et al. |
| 2012/0253302 A1 | 10/2012 | Corley |
| 2013/0012891 A1 | 1/2013 | Gross et al. |
| 2013/0023842 A1 | 1/2013 | Song |
| 2013/0066365 A1 | 3/2013 | Belson et al. |
| 2013/0150813 A1 | 6/2013 | Gordon et al. |
| 2013/0190705 A1 | 7/2013 | Vess et al. |
| 2013/0197457 A1 | 8/2013 | Kazala, Jr. et al. |
| 2013/0204213 A1 | 8/2013 | Heagle et al. |
| 2013/0245527 A1 | 9/2013 | Croizat et al. |
| 2013/0325142 A1 | 12/2013 | Hunter et al. |
| 2013/0331757 A1 | 12/2013 | Belson |
| 2014/0094730 A1 | 4/2014 | Greener et al. |
| 2014/0163415 A1 | 6/2014 | Zaiken et al. |
| 2014/0180225 A1* | 6/2014 | Dunn ............... A61B 17/08 604/319 |
| 2014/0228732 A1 | 8/2014 | Steinbaugh et al. |
| 2014/0228789 A1 | 8/2014 | Wilkes et al. |
| 2014/0249495 A1 | 9/2014 | Mumby et al. |
| 2015/0065968 A1 | 3/2015 | Sealy et al. |
| 2015/0119837 A1 | 4/2015 | Thompson, Jr. et al. |
| 2015/0157758 A1 | 6/2015 | Blucher et al. |
| 2015/0196431 A1 | 7/2015 | Dunn et al. |
| 2015/0216732 A1 | 8/2015 | Hartwell et al. |
| 2015/0320602 A1 | 11/2015 | Locke et al. |
| 2015/0374561 A1 | 12/2015 | Hubbard, Jr. et al. |
| 2016/0144085 A1 | 5/2016 | Melin et al. |
| 2016/0184496 A1 | 6/2016 | Jaecklein et al. |
| 2017/0007751 A1* | 1/2017 | Hartwell ............... A61M 1/90 |
| 2017/0065458 A1* | 3/2017 | Mumby ............ A61F 13/00987 |
| 2017/0065751 A1 | 3/2017 | Toth |
| 2017/0165116 A1 | 6/2017 | Dunn |
| 2017/0281838 A1 | 10/2017 | Dunn |
| 2020/0188564 A1 | 6/2020 | Dunn |
| 2020/0353136 A1 | 11/2020 | Greener |

FOREIGN PATENT DOCUMENTS

| | | |
|---|---|---|
| CN | 101112326 A | 1/2008 |
| CN | 101744688 A | 6/2010 |
| CN | 201519362 U | 7/2010 |
| CN | 102038575 A | 5/2011 |
| CN | 202568632 U | 12/2012 |
| CN | 103071197 A | 5/2013 |
| CN | 203408163 U | 1/2014 |
| DE | 2949920 A1 | 3/1981 |
| EP | 1320342 A1 | 6/2003 |
| EP | 2185209 A2 | 5/2010 |
| EP | 2279016 A1 | 2/2011 |
| EP | 2567717 A1 | 3/2013 |
| EP | 2601984 A2 | 6/2013 |
| GB | 2389794 A | 12/2003 |
| GB | 2423019 A | 8/2006 |
| GB | 2489947 A | 10/2012 |
| GB | 2496310 A | 5/2013 |
| JP | S62-57560 A | 3/1987 |
| JP | 2006-528038 A | 12/2006 |
| JP | 2009-525087 A | 7/2009 |
| JP | 2012-105840 A | 6/2012 |
| RU | 62504 U1 | 4/2007 |
| SU | 1818103 A1 | 5/1993 |
| WO | WO 01/85248 A1 | 11/2001 |
| WO | WO 01/89392 A2 | 11/2001 |
| WO | WO 02/05737 A1 | 1/2002 |
| WO | WO 03/003948 A1 | 1/2003 |
| WO | WO 03/049598 A2 | 6/2003 |
| WO | WO 2005/046761 A1 | 5/2005 |
| WO | WO 2005/105174 A1 | 11/2005 |
| WO | WO 2006/646060 A2 | 5/2006 |
| WO | WO 2008/027449 A2 | 3/2008 |
| WO | WO 2008/064502 A1 | 6/2008 |
| WO | WO 2008/104609 A1 | 9/2008 |
| WO | WO 2009/112062 A1 | 9/2009 |
| WO | WO 2010/033725 A2 | 3/2010 |
| WO | WO 2010/097576 A1 | 9/2010 |
| WO | WO 2011/023384 A1 | 3/2011 |
| WO | WO 2012/082716 A2 | 6/2012 |
| WO | WO 2012/082876 A1 | 6/2012 |
| WO | WO 2012/136707 A1 | 10/2012 |
| WO | WO 2012/142473 A1 | 10/2012 |
| WO | WO 2013/012381 A1 | 1/2013 |
| WO | WO 2013/043258 A1 | 3/2013 |
| WO | WO 2013/071243 A2 | 5/2013 |
| WO | WO 2013/076450 A1 | 5/2013 |
| WO | WO 2013/079947 A1 | 6/2013 |
| WO | WO 2013/175309 A1 | 11/2013 |
| WO | WO 2013/175310 A2 | 11/2013 |
| WO | WO 2014/013348 A2 | 1/2014 |
| WO | WO 2014/014922 A1 | 1/2014 |
| WO | WO 2014/140578 A1 | 9/2014 |
| WO | WO 2014/158526 A1 | 10/2014 |
| WO | WO 2014/165275 A1 | 10/2014 |
| WO | WO 2014/178945 A1 | 11/2014 |
| WO | WO 2014/194786 A1 | 12/2014 |
| WO | WO 2015/008054 A1 | 1/2015 |
| WO | WO 2015/061352 A2 | 4/2015 |
| WO | WO 2015/109359 A1 | 7/2015 |
| WO | WO 2015/110409 A1 | 7/2015 |
| WO | WO 2015/110410 A1 | 7/2015 |
| WO | WO 2015/169637 A1 | 11/2015 |
| WO | WO 2015/193257 A1 | 12/2015 |
| WO | WO 2016/018448 A1 | 2/2016 |
| WO | WO 2016/176513 A1 | 11/2016 |
| WO | WO 2016/179245 A1 | 11/2016 |
| WO | WO 2017/106576 A1 | 6/2017 |
| WO | WO 2018/038665 A1 | 3/2018 |
| WO | WO 2018/041805 A1 | 3/2018 |
| WO | WO 2018/044944 A1 | 3/2018 |

(56) References Cited

FOREIGN PATENT DOCUMENTS

| WO | WO 2018/044949 A1 | 3/2018 |
| WO | WO 2018/085457 A1 | 5/2018 |
| WO | WO 2018/140386 A2 | 8/2018 |

OTHER PUBLICATIONS

International Search Report and Written Opinion for Application No. PCT/EP2018/071116, dated Nov. 14, 2018, 15 pages.

"Definition of 3D Printer," American Heritage Dictionary of the English Language, Fifth Edition, accessed on Feb. 22, 2018 from URL: https://www.thefreedictionary.co, 2016, 1 page.

"Definition of Adhere," The Free Dictionary, accessed on Mar. 23, 2017 from http://www.thefreedictionary.com/adhere, 6 pages.

"Definition of Oculiform," Webster's Revised Unabridged Dictionary, accessed from the Free Dictionary on May 30, 2018 from URL: https://www.thefreedictionary.com/Oculiform, 1913, 1 page.

"Definition of Throughout," Merriam-Webster Dictionary, accessed on Aug. 29, 2017 from https://www.merriam-webster.com/dictionary/throughout, 11 pages.

Hougaard, et al., "the Open Abdomen: Temporary Closure with a Modified Negative Pressure Therapy Technique," International Wound Journal, ISSN 1742-4801, 2014, pp. 13-16.

Kapischke M., et al., "Self-Fixating Mesh for the Lichtenstein Procedure-a Prestudy," Langenbecks Arch Surg, 2010, vol. 395, pp. 317-322.

\* cited by examiner

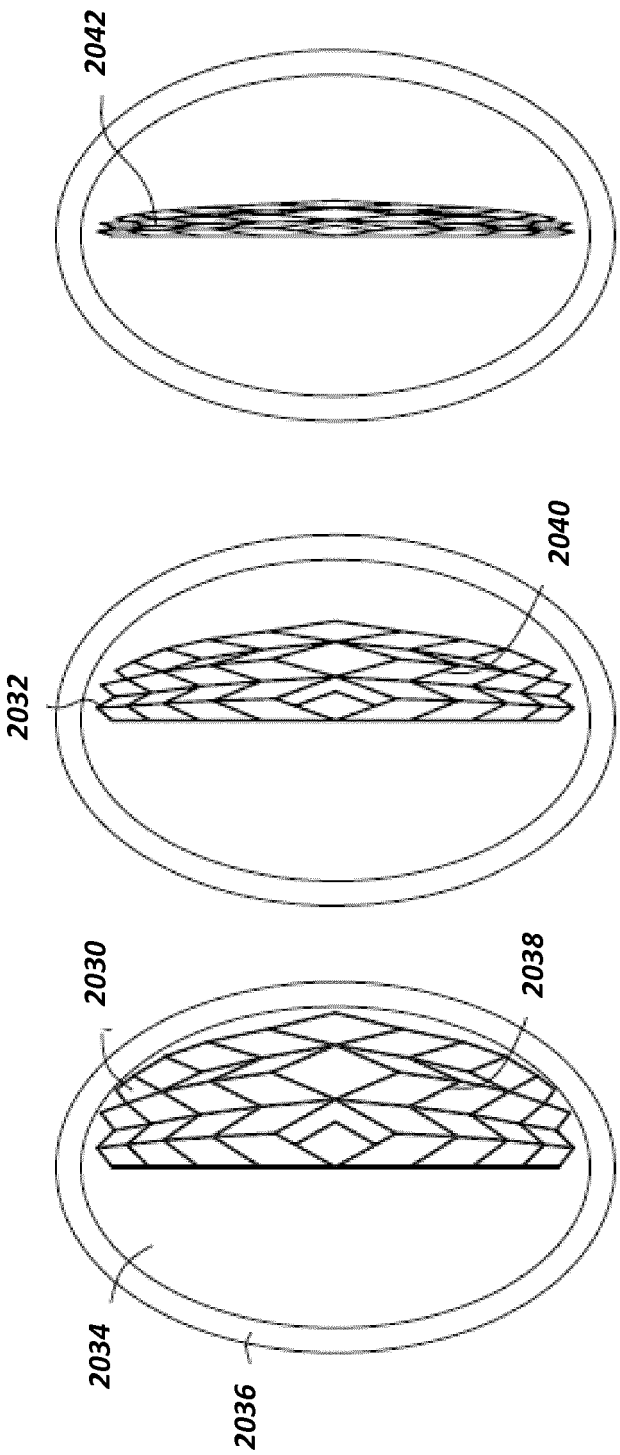

WOUND CLOSURE DEVICE WITH PROTECTIVE LAYER AND METHOD OF USE

CROSS-REFERENCE TO RELATED APPLICATIONS

This application is a U.S. national stage application of International Patent Application No. PCT/EP2018/071116, filed Aug. 3, 2018, which claims the benefit of U.S. Application No. 62/541,978, filed Aug. 7, 2017, the disclosure of each of which is hereby incorporated by reference in its entirety.

BACKGROUND

Field of the Invention

This application describes embodiments of apparatuses, methods, and systems for the treatment of wounds, specifically to aid in the closure of large wounds, in conjunction with the administration of negative pressure.

Description of the Related Art

Negative pressure wound therapy has been used in the treatment of wounds, and in many cases, can improve the rate of healing while also removing exudates and other deleterious substances from the wound site.

Abdominal compartment syndrome is caused by fluid accumulation in the peritoneal space due to edema and other such causes, and results in greatly increased intra-abdominal pressure that may cause organ failure eventually resulting in death. Causes may include sepsis or severe trauma. Treatment of abdominal compartment syndrome may require an abdominal incision to permit decompression of the abdominal space, and as such, a large wound may be created onto the patient. Closure of this wound, while minimizing the risk of secondary infections and other complications, and after the underlying edema has subsided, then becomes a priority. However, acute open abdominal conditions may be caused by other reasons in addition to compartment syndrome, as described further below.

Other large or incisional wounds, either as a result of surgery, trauma, or other conditions, may also require closure. For example, wounds resulting from sternotomies, fasciotomies, and other abdominal wounds may require closure. Wound dehiscence of existing wounds is another complication that may arise, possibly due to incomplete underlying fascial closure, or secondary factors such as infection.

Existing negative pressure treatment systems, while permitting eventual wound closure, still require lengthy closure times. Although these may be combined with other tissue securement means, such as sutures, there is also a risk that underlying muscular and fascial tissue is not appropriately reapproximated so as to permit complete wound closure. Further, when foam or other wound fillers are inserted into the wound, the application of negative pressure to the wound and the foam may cause atmospheric pressure to bear down onto the wound, compressing the foam downward and outward against the margins of the wound. This downward compression of the wound filler slows the healing process and slows or prevents the joining of wound margins. Additionally, inflammation of the fascia in the form of certain types of fasciitis can lead to rapid and excessive tissue loss, potentially meriting the need for more advanced negative pressure treatment systems. Accordingly, there is a need to provide for an improved apparatus, method, and system for the treatment and closure of wounds.

SUMMARY

Embodiments of the present invention relate to negative pressure wound closure devices, methods, and systems that facilitate closure of a wound. It will be understood by one of skill in the art that the wounds described herein this specification may encompass any wound, and are not limited to a particular location or type of wound. The devices, methods, and systems may operate to reduce the need for repetitive replacement of wound filler material currently employed and can advance the rate of healing. The devices, methods, and systems may be simultaneously used with negative pressure to remove wound fluids.

In certain embodiments, a wound closure device may comprise:
 a stabilizing structure for insertion into a wound, the stabilizing structure comprising a top surface and a bottom surface and a plurality of cells extending between the top surface and the bottom surface, the cells configured to allow the stabilizing structure to collapse; and
 a protective layer attached or attachable to the top surface of the stabilizing structure, the protective layer comprising a plurality of openings sized and configured to allow visualization of the cells underneath the protective layer.

In some embodiments, the protective layer may comprise a layer of mesh or net. The layer of mesh or net may comprise polyethylene. Each of the plurality of openings of the protective layer may have a size smaller than the cells. In some embodiments, the plurality of openings may have average size of 1-3 mm. The protective layer may conform to the shape of the stabilizing structure.

In some embodiments, the wound closure device may further comprise a bottom layer of foam positioned or positionable underneath the stabilizing structure, the bottom layer of foam comprising a lip that is configured to extend outward relative to the stabilizing structure. The bottom layer of foam may be attached to the bottom surface of the stabilizing structure. In some embodiments, the wound closure device may further comprise a middle layer of foam attached to the bottom surface of the stabilizing structure, the middle layer of foam conforming to the shape of the stabilizing structure. The bottom layer of foam may be attached to the middle layer of foam. In some embodiments, the bottom layer of foam may comprise cuts, the cuts defining frangible portions of the foam.

In some embodiments, the stabilizing structure may be configured to collapse more in a horizontal plane parallel to a length and a width of the stabilizing structure than in a vertical plane perpendicular to the horizontal plane. The wound closure device may further comprise a source of negative pressure and/or a drape configured to be positioned over the protective layer and the stabilizing structure to seal to skin surrounding the wound. The wound closure device may further comprise a port, wherein the port is configured to transmit negative pressure through the drape.

In certain embodiments, a method of treating a wound may comprise:
 positioning within the wound a stabilizing structure comprising a plurality of collapsible cells and a protective layer over the stabilizing structure having a plurality of openings;

applying one or more drapes over the stabilizing structure and the protective layer to create a fluid tight seal; and delivering negative pressure through or under the one or more drapes to cause collapse of the cells, wherein the protective layer permits the collapse of the cells to be visualized during delivery of negative pressure.

In some embodiments, the method may further comprise cutting the protective layer such that the protective layer conforms to the shape of the stabilizing structure. The stabilizing structure may be positioned within the wound with a bottom layer of foam attached to a bottom of the stabilizing structure, the bottom layer of foam comprising a lip extending outward of the stabilizing structure and positioned beneath tissue surrounding the stabilizing structure. The bottom layer of foam may comprise detachable portions, the method further comprising detaching portions of the bottom layer of foam before positioning the bottom layer of foam within the wound.

Other embodiments of wound closure devices, stabilizing structures and associated apparatuses are described below.

BRIEF DESCRIPTION OF THE DRAWINGS

Other features and advantages of the present invention will be apparent from the following detailed description of the invention, taken in conjunction with the accompanying drawings of which:

FIGS. 3A-E illustrate multiple views of another embodiment of a stabilizing structure and a method of creating the stabilizing structure.

FIG. 10 contains photographs of embodiments of steps of a method of treating a wound.

DETAILED DESCRIPTION

Figure 1:
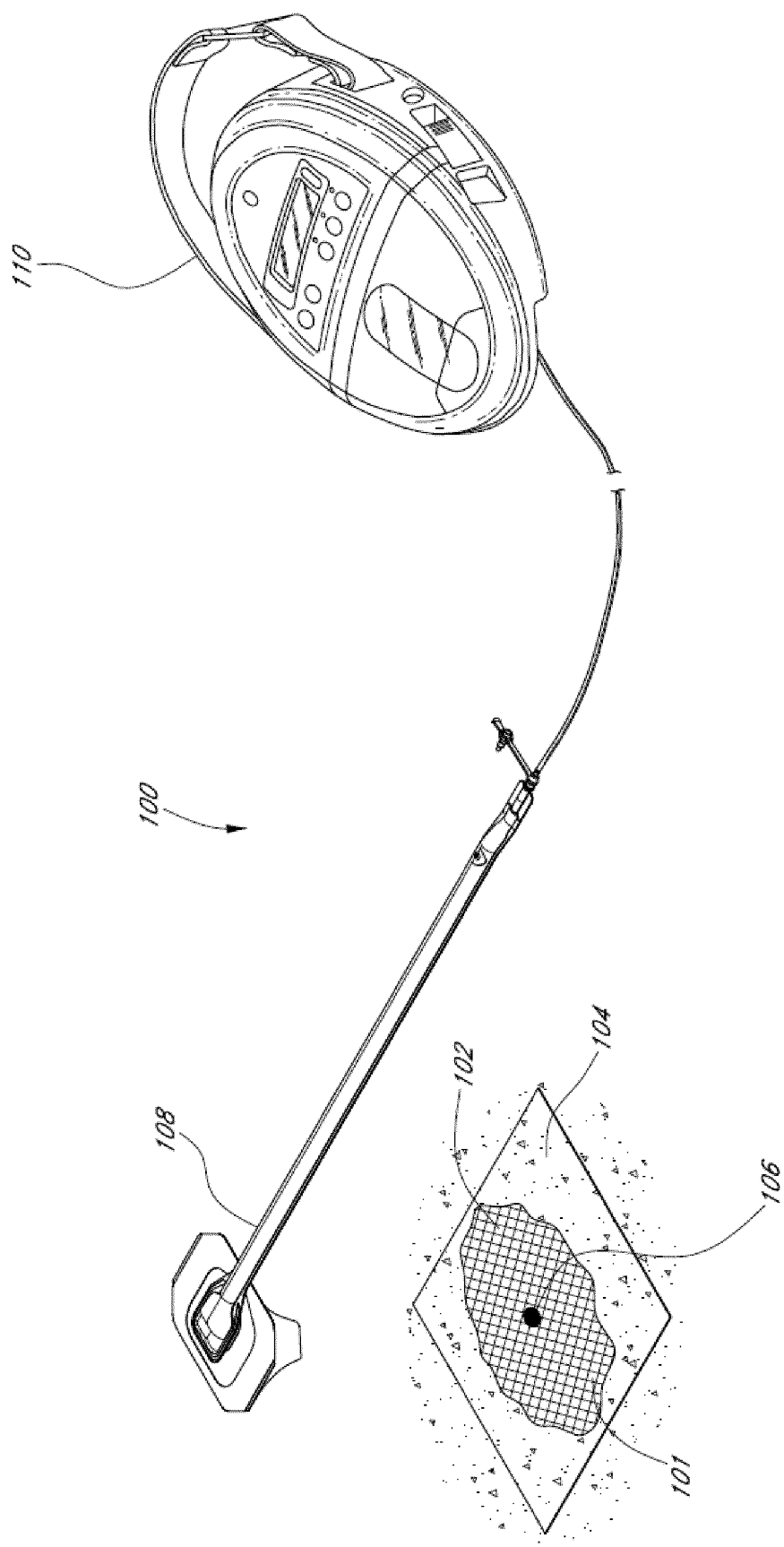
FIG. 1 illustrates an embodiment of a negative pressure treatment system.

Embodiments disclosed in this section or elsewhere in this specification relate to apparatuses and methods of treating a wound with reduced pressure, including pump and wound dressing components and apparatuses. The apparatuses and components comprising the wound overlay and packing materials, if any, are sometimes collectively referred to in this section or elsewhere in this specification as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sternotomies, fasciotomies, or other conditions, dehisced wounds, acute wounds, chronic wounds, subacute and dehisced wounds, traumatic wounds, flaps and skin grafts, lacerations, abrasions, contusions, burns, electrical burns, diabetic ulcers, pressure ulcers, stoma, surgical wounds, trauma and venous ulcers or the like.

As is used in this section or elsewhere in this specification, reduced or negative pressure levels, such as −X mmHg, represent pressure levels that are below standard atmospheric pressure, which corresponds to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760-X) mmHg. In addition, negative pressure that is "less" or "smaller" than −X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

The negative pressure range for some embodiments of the present disclosure can be approximately −80 mmHg, or between about −10 mmHg and −200 mmHg Note that these pressures are relative to normal ambient atmospheric pressure. Thus, −200 mmHg would be about 560 mmHg in practical terms. In some embodiments, the pressure range can be between about −40 mmHg and −150 mmHg. Alternatively, a pressure range of up to −75 mmHg, up to −80 mmHg or over −80 mmHg can be used. Also in other embodiments, a pressure range of below −75 mmHg can be used. Alternatively, a pressure range of over approximately −100 mmHg, or even −150 mmHg, can be supplied by the negative pressure apparatus. In some embodiments, the negative pressure range can be as small as about −20 mmHg or about −25 mmHg, which may be useful to reduce fistulas. In some embodiments of wound closure devices described here, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat).

Examples of such applications where additional disclosure relating to the preceding descriptions may be found include U.S. Pat. No. 8,235,955, titled "Wound treatment apparatus and method," issued Aug. 7, 2012 and U.S. Pat. No. 7,753,894, titled "Wound cleansing apparatus with stress," issued Jul. 13, 2010. Both applications are hereby incorporated by reference in their entirety. Other applications that may contain teachings relevant for use with the embodiments described in this section or elsewhere in this specification may include application Ser. No. 12/886,088, titled "Systems And Methods For Using Negative Pressure Wound Therapy To Manage Open Abdominal Wounds," filed Sep. 20, 2010, published as US 2011/0213287; application Ser. No. 13/092,042, titled "Wound Dressing And Method Of Use," filed Apr. 21, 2011, published as US 2011/0282309; and application Ser. No. 13/365,615, titled "Negative Pressure Wound Closure Device," filed Feb. 3, 2012, published as US 2012/0209227, the entireties of each of which are hereby incorporated by reference. Still more applications that may contain teachings relevant for use with the embodiments described in this specification are application Ser. No. 13/942,493, titled "Negative Pressure Wound Closure Device," filed Jul. 15, 2013, published as US 2014/0180225; PCT App. No. PCT/US2013/050619, filed Jul. 16, 2013 titled "Negative Pressure Wound Closure Device," published as WO 2014/014871 A1; PCT App. No. PCT/US2013/050698, filed Jul. 16, 2013 titled "Negative Pressure Wound Closure Device," published as WO 2014/014922 A1; PCT App. No. PCT/IB2013/01555, titled "Devices and Methods for Treating and Closing Wounds with Negative Pressure," filed May 5, 2013, published as WO 2013/175309 A1; PCT App. No. PCT/US2014/025059, titled "Negative Pressure Wound Closure Device and Systems and Methods of Use in Treating Wounds with Negative Pressure," filed Mar. 12, 2014, published as WO 2014/165275 A1; and PCT App. No. PCT/GB2014/050746, "Compressible Wound Fillers and Systems and Methods of Use In Treating Wounds With Negative Pressure," filed Mar. 13, 2014, published as WO 2014/140578 A1, and "Negative Pressure Wound Closure Device," filed Oct. 21, 2014, and published as PCT/US2014/061627. The entireties of the aforementioned applications are each hereby incorporated by reference and should be considered part of the present specification.

It will be understood that throughout this specification, in some embodiments, reference is made to an elongate, elongated or longitudinal strip or strips. It is to be understood that these terms are to be broadly construed and refer in some embodiments to an elongate material having two parallel or substantially parallel faces, where in cross-section a thickness of the material as measured perpendicular to the faces is relatively smaller than a height of the material measured parallel to the faces. While in some embodiments the strips may be constructed from discrete lengths of material, in other embodiments the strips may simply refer to elongate portions of an overall structure having two parallel or substantially parallel faces. The strips in some embodiments have a rectangular or generally rectangular-shaped faces, wherein a length of the face is longer than the height of the face. In some embodiments, the length of the face may be more than 2 times, 4 times, 6 times, 8 time, 10 times, 12 times or more greater than the height of the face.

As used in this section or elsewhere in this specification, the term "horizontal," when referring to a wound, indicates a direction or plane generally parallel to the skin surrounding the wound. The term "vertical," when referring to a wound, generally refers to a direction extending perpendicular to the horizontal plane. The term "longitudinal," when referring to a wound, generally refers to a direction in the horizontal plane taken in a direction along which the wound is longest. The term "lateral," when referring to a wound, generally refers to a direction in the horizontal plane perpendicular to the longitudinal direction. The terms "horizontal," "vertical," "longitudinal" and "lateral" may also be used to describe the stabilizing structures and wound closure devices described throughout this specification. When describing these structures or devices, these terms should not be construed to require that the structures or devices necessarily be placed into a wound in a certain orientation, though in certain embodiments, it may be preferable to do so.

FIG. 1 illustrates an embodiment of a negative pressure treatment system 100 that comprises a wound packer 102 inserted into a wound 101. The wound packer 102 may comprise porous materials such as foam, and in some embodiments, may comprise one or more embodiments of wound closure devices described in further detail in this section or elsewhere in this specification. In some embodiments, the perimeter or top of any wound closure device inserted into the wound 101 may also be covered with foam or other porous materials. A single drape 104 or multiple drapes may be placed over the wound 101, and is preferably adhered or sealed to the skin on the periphery of the wound 101 so as to create a fluid-tight seal. An aperture 106 may be made through the drape 104 which can be manually made or preformed into the drape 104 so as to provide a fluidic connection from the wound 101 to a source of negative pressure such as a pump 110. Preferably, the fluidic connection between the aperture 106 and the pump 110 is made via a conduit 108. In some embodiments, the conduit 108 may comprise a RENASYS® Soft Port™, manufactured by Smith & Nephew. Of course, in some embodiments, the drape 104 may not necessarily comprise an aperture 106, and the fluidic connection to the pump 110 may be made by placing the conduit 108 below the drape. In some wounds, particularly larger wounds, multiple conduits 108 may be used, fluidically connected via one or more apertures 106.

In some embodiments, the drape 104 may be provided with one or more corrugations or folds. Preferably, the corrugations are aligned along the longitudinal axis of the wound, and as such may support closure of the wound by preferentially collapsing in a direction perpendicular to the longitudinal axis of the wound. Such corrugations may aid in the application of contractile forces parallel to the wound surface and in the direction of wound closure. Examples of such drapes may be found in application Ser. No. 12/922,118, titled "Vacuum Closure Device," filed Nov. 17, 2010 (published as US 2011/0054365), which is hereby incorporated by reference in its entirety.

In use, the wound 101 is prepared and cleaned. In some cases, such as abdominal wounds, a non- or minimally-adherent organ protection layer (not illustrated) may be applied over any exposed viscera. The wound packer 102 is then inserted into the wound, and is covered with the drape 104 so as to form a fluid-tight seal. A first end of the conduit 108 is then placed in fluidic communication with the wound, for example via the aperture 106. The second end of the conduit 108 is connected to the pump 110. The pump 110 may then be activated so as to supply negative pressure to the wound 101 and evacuate wound exudate from the wound 101. As will be described in additional detail below and in relation to the embodiments of the foregoing wound closure devices, negative pressure may also aid in promoting closure of the wound 101, for example by approximating opposing wound margins.

Any structure or component disclosed herein this section or elsewhere in the specification may comprise a radiopaque material. A radiopaque material advantageously allows a clinician to more easily find pieces of the wound closure device that may have come loose from the structure and become lost in the wound. Some examples of radiopaque materials include barium sulfate, bismuth trioxide, bismuth subcarbonate, bismuth oxychloride, and tungsten.

Stabilizing Structures and Wound Closure Devices of FIG. 2A-3E

Figure 2A:
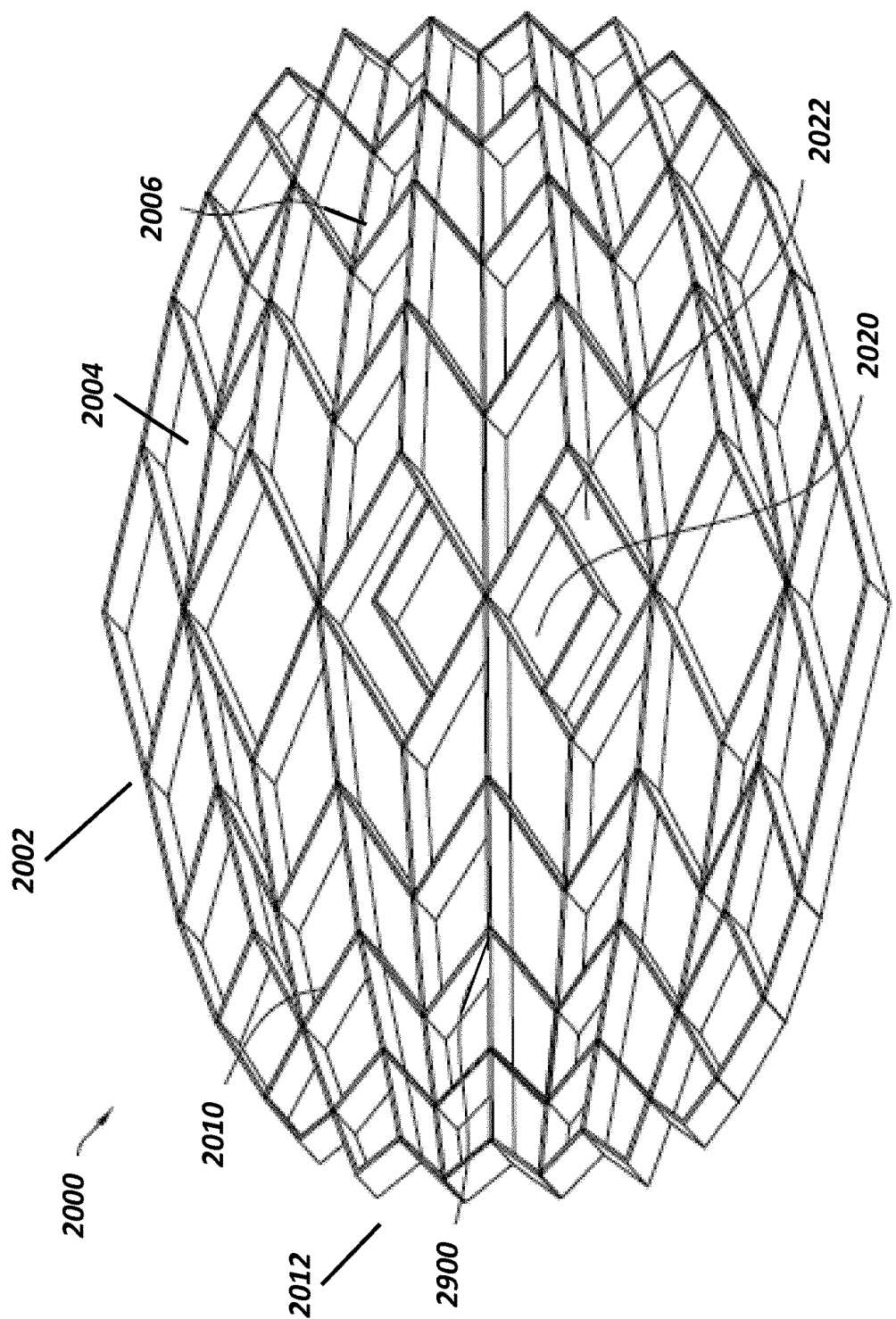
FIGS. 2A-C illustrate multiple views of an embodiment of a stabilizing structure.

FIG. 2A is a drawing of an embodiment of a stabilizing structure 2000 comprising a plurality of elongate strips 2006 arranged in parallel or semi-parallel, whose longitudinal length can be aligned with the longitudinal axis of a wound. In embodiments, the elongate strips 2006 may also be arranged in a non-parallel fashion. The various cells within this stabilizing structure 2000 may have a variety of shapes and sizes. As will be described in greater detail below, the length and shape of the elongate strips 2006, intervening members 2010, and cells 2004 may be designed so as to facilitate greater closure of the stabilizing structure. In certain embodiments, the junctions 2900 between the elongate strips and intervening members may be thinned to better facilitate rotation and closure of the stabilizing structures. In some embodiments, the stabilizing structure is tearable, such that the structure may be shaped into the shape of a wound. As described elsewhere in the specification, tears may be completed at the intersections between intervening members and elongate strips or at any suitable location along the elongate strip or intervening member.

All stabilizing structures described herein this section or elsewhere in the specification may be fashioned to accommodate any size of wound. However, to better accommodate the needs of the clinical environment, in certain embodiments, the stabilizing structures described herein may be provided in a pack of two sizes, one smaller stabilizing structure and one larger stabilizing structure about 1.25 times as larger, about 1.5 times as large, about 1.75 times as large, about 2 times as larger, about 2.5 times as larger, about 3 times as large, about 4 times as large, about 5 times as large, or more than about 5 times as large. In some embodiments, the pack may comprise more than two sizes, such as three sizes, four sizes, five sizes, or more than five sizes. The stabilizing structures within the pack may be of a variety of sizes in relation to one another such as the ratios described above.

In certain embodiments, the stabilizing structure 2000 can collapse in any manner described in this section or elsewhere in this specification with or without the application of negative pressure. For example, the stabilizing structure may collapse significantly more in one plane than in another plane upon application of negative pressure. In some embodiments, the stabilizing structure is configured to collapse more in a horizontal plane parallel to the length and width of the stabilizing structure than in a vertical plane perpendicular to the horizontal plane. In embodiments, particular rows may collapse in a first direction, while another row may collapse in the same or an opposing direction. In certain embodiments, the stabilizing structure may collapse along the width of the stabilizing structure while remaining relatively rigid along the length of the stabilizing structure and in the vertical direction.

The stabilizing structure may be comprised of any materials described in this section or elsewhere in this specification, including: flexible plastics such as silicone, polyurethane, rigid plastics such as polyvinyl chloride, semi-rigid plastics, semi-flexible plastics, biocompatible materials, composite materials, metals, and foam. In certain embodiments, the stabilizing structure may comprise a radio opaque material, to more readily allow a clinician to find pieces of the stabilizing structure within the wound.

Returning to FIG. 2A, stabilizing structure 2000 may have an outer perimeter that defines an at least partially elliptical shape. As described above, stabilizing structure 2000 may comprise a plurality of cells 2004 provided side-by-side, each cell defined by one or more walls, each cell having a top end and a bottom end with an opening extending through the top and bottom ends. As with the other stabilizing structures described herein this section and elsewhere in the specification, the stabilizing structure 2000 is configured to collapse by collapsing one or more cells 2004. In some embodiments, the cells are all of the same approximate shape and size; however, in other embodiments, the cells are of different shapes and sizes. In some embodiments, the stabilizing structures as described herein this section or elsewhere in the specification may be domed, such that the central portion of the stabilizing structure bulges upward. For example, a lower portion of the stabilizing structure may be concave, while an upper portion of the stabilizing structure is convex.

The elongate strips 2006 may be made from one single material, such as those described elsewhere in the specification, or the elongate strips may be made from multiple materials. For example, elongate strips 2006 may comprise sections of more rigid material and sections of more flexible material. The elongate strips 2006 may be curved along their length so as to facilitate the curved outer perimeter of the stabilizing structure 2000. The elongate strips may be curved along their lengths outward away from a center of the stabilizing structure 2000. The arch of the curves of the elongate strips 2006 may vary considerably, with some strips 2006 being highly curved while other are minimally curved or even straight.

Similarly, the stabilizing structure 2000 can further comprise a plurality of intervening members 2010 connected to the elongate strips 2006. The intervening members 2010 may all be of a similar shape and size or they may be of a variety of shapes and sizes. The intervening members may be constructed from any material disclosed herein this section or elsewhere in the specification. Further, the intervening members may be constructed from multiple materials.

Advantageously, the elliptical shape of stabilizing structure 2000 may allow the structure to better accommodate the shape of the wound. Most wounds are in shapes that are rounded, thus, an elliptically shaped stabilizing structure 2000 may better fit into a wound.

In embodiments, the outer perimeter 2002 may have a reduced edge 2012 so as to facilitate collapse of the stabilizing structure. By removing mass of the stabilizing structure at reduced edge 2012, the stabilizing structure can collapse more freely at reduced edge 2012, thus allowing for a better fit within the wound. Further, by reduced the mass at reduced edge 2012, there may be less pinching of the surrounding tissue during and after collapse of the stabilizing structure 2000.

The stabilizing structure 2000 and all stabilizing structures and wound closure devices described in this section or elsewhere in this specification can collapse on a variety of timescales in a dynamic fashion. In certain embodiments, the majority of the collapse may occur within the first few minutes upon application of negative pressure. However, after the initial collapse, the stabilizing structure or wound closure device may continue to collapse at a much slower rate, thereby applying increasing longitudinal tension over a long period of time and drawing the edges of the wound closer together. By slowly drawing the wound edges closer together over time, the stabilizing structure or wound closure device allows the surrounding healing tissue to remodel synergistically with the closure of the device or stabilizing structure. Slow, dynamic wound closure may allow the surrounding tissue to heal at an accelerated rate, because the collapsing structure or device slowly brings the edges of the wound closer together without stressing the newly formed or weakened tissue too quickly.

In some embodiments, the stabilizing structures described in this section or elsewhere in this specification can be placed into a wound for a period of time and then removed or replaced with another stabilizing structure. For example, a stabilizing structure could be inserted into a wound for a period of time, promoting closure of the wound by drawing the edges closer together. After a period of time has passed, the stabilizing structure can be replaced by a stabilizing structure of a different size or collapsibility, for example a stabilizing structure of a smaller size or decreased density. This process could be repeated over and over, thereby continuously drawing the edges of the wound together over time and allowing for continuing repair and remodeling of the surrounding tissue. In certain embodiments, the stabilizing structure is configured to remain in the wound for at least about less than 1 hour, at least about 1 hour, at least about 2 hours, at least about 4 hours, at least about 6 hours, at least about 8 hours, at least about 12 hours, at least about 24 hours, at least about 2 days, at least about 4 days, at least about 6 days, at least about 1 week, at least about 2 weeks, at least about 3 weeks, or more than 3 weeks.

In certain embodiments, up to 90% of the collapse of the stabilizing structure or wound closure device may occur within the first few minutes upon application of negative pressure, while the remaining 10% of the collapse may occur slowly over a period of many minutes, hours, days, weeks, or months. In other embodiments, up to about 80% of the collapse, up to about 70%, up to about 60%, up to about 50%, up to about 40%, up to about 30%, up to about 20%, up to about 10%, or about 0% of the collapse will occur immediately within the first few minutes upon application of negative pressure while the remainder of the collapse occurs at a much slower rate such as over the course of many minutes, hours, days weeks, or months. In other embodiments, the stabilizing structure can collapse at a variable rate. In some embodiments, the entirety of the collapse occurs at a slowed rate, while in other embodiments the entirety of the collapse occurs almost immediately within the first few minutes. In further embodiments, the collapse can occur at any rate and the rate can vary over time. In certain embodiments, the rate of collapse can be altered in a variable fashion by adding and/or removing portions of the structure or by controlling the application of negative pressure and irrigant fluid.

Returning to FIG. 2A, in some embodiments, the pattern of the stabilizing structure 2000 is designed in such a way as to facilitate maximum closure of the stabilizing structure. Preferably, maximum closure is in a direction perpendicular to the length of the elongate members and within the horizontal plane. As will be described in greater detail below, greater closure may be achieved by varying the length of the elongate strips 2006, the length of the intervening members 2010, and the shape of the cells 2004. The shape of the cells 2004 may comprise any shape described herein this section or elsewhere in the specification. For example, as depicted in FIG. 2A, the cells 2004 may be diamond-shaped or parallelepiped with smaller diamond-like shapes 2020 located within larger diamonds 2022. Such a construction may provide greater overall closure of the stabilizing device 2000 to provide for maximum closure of the wound. Additionally, the smaller diamond-like shapes 2020 located within larger diamonds 2022 can spread the load over a greater area reducing the chance of damage to the tissue structures below the matrix. This construction can also reduce the likelihood of the foam or the drape being pulled into the matrix and preventing closure of the wound.

Figure 2B:
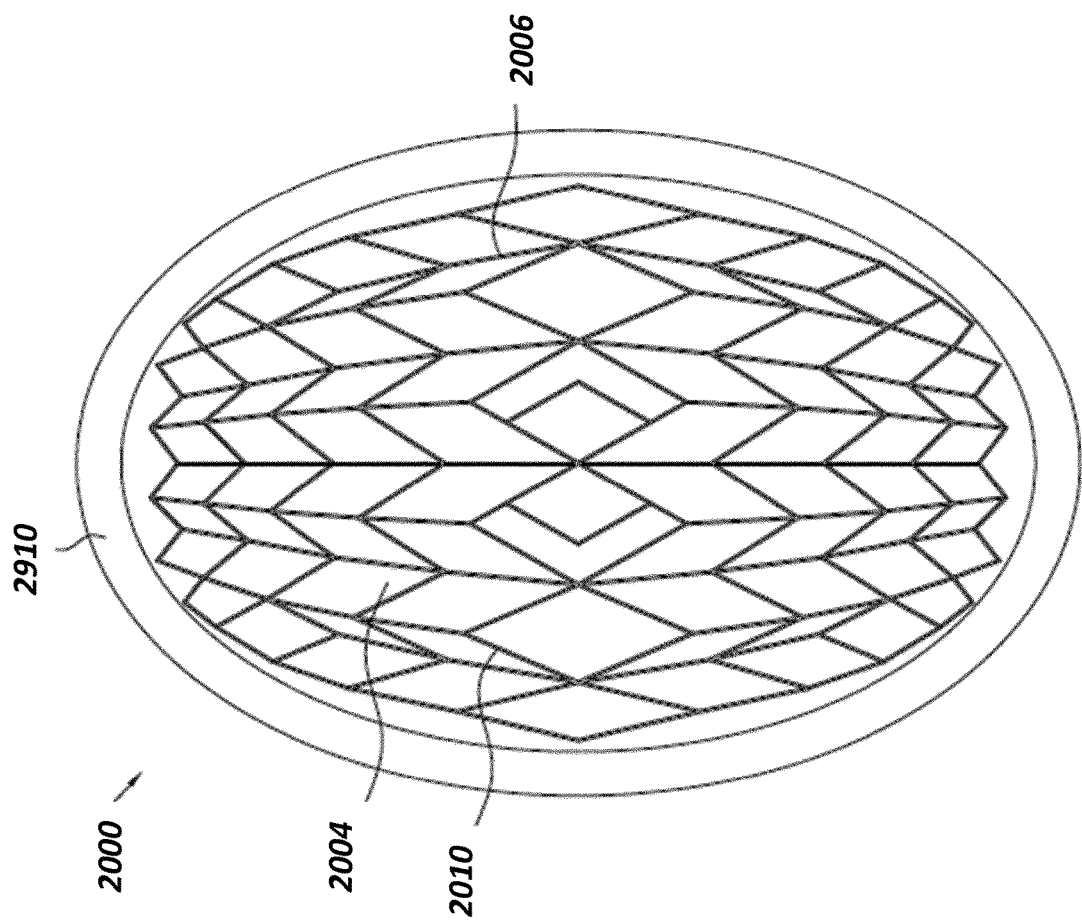
Figure 2C:
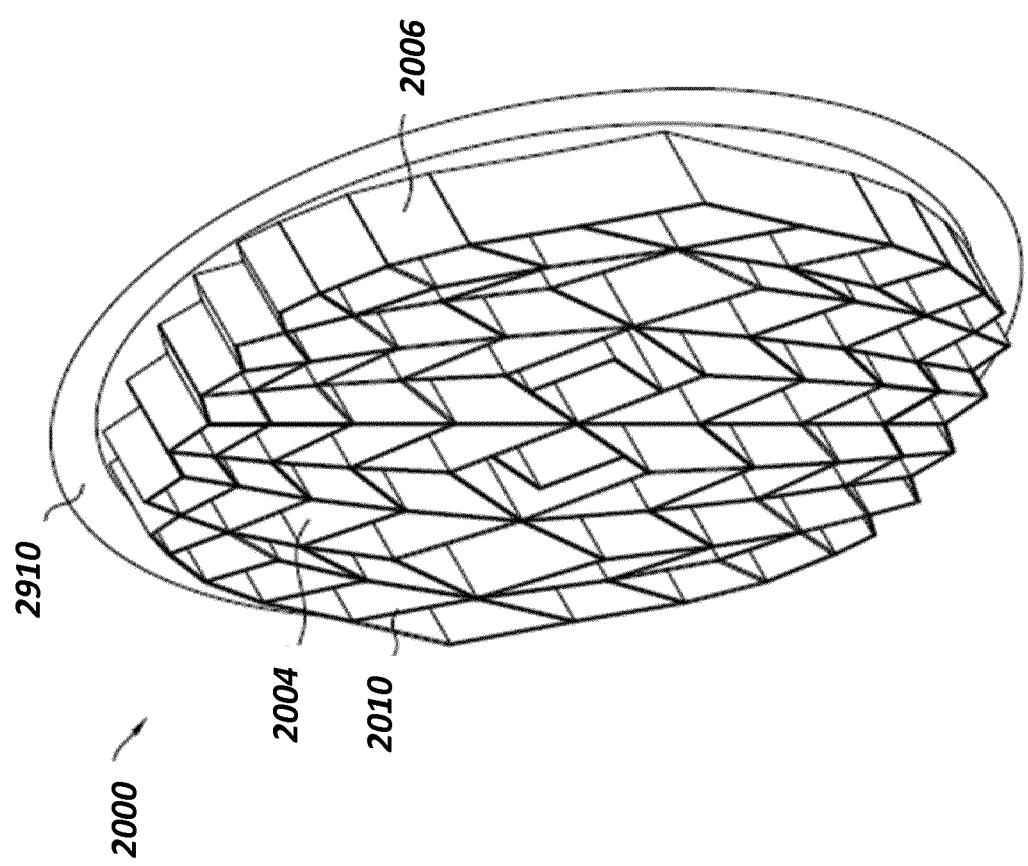

FIGS. 2B-C are illustrations of different views of the stabilizing structure embodiment of FIG. 2A. As described above in relation to FIG. 2A, the stabilizing structure comprises cells 2004, intervening members 2010, and elongate strips 2006; however, here a simulated shape of a wound 2910 is also included for comparison.

Any of the stabilizing structures described herein this section or elsewhere in the specification may be constructed from any suitable means. For example, the stabilizing structures may be constructed via molding or may be printed directly using 3D printing technology. In certain embodiments, the stabilizing structures of FIGS. 2A-C may be constructed from a single polymer via 3D printing. In some embodiments, the stabilizing structures may be constructed from one polymer, two polymers, three polymers, or more than three polymers. The stabilizing structures may be constructed from any material disclosed herein this section or elsewhere in the specification. The stabilizing structure can be made by cutting the structure out of a solid block of material. Methods used for cutting can include, for example, water jet cutting, laser cutting, or die cutting. The stabilizing structures may be cut to size along the walls of the cells 2004. For example, the intervening members along the outside face of elongate strips 2006 can be cut off to appropriately size the stabilizing structure. The stabilizing structure may be cut along the walls, along any portions of the elongate strips, and/or along any portions of the intervening members.

In some embodiments, the stabilizing structure 2000 of FIGS. 2A-C can be configured to include perforations or detachable sections that allow portions of the device to separate from the remainder of the device. For example, perforations may be incorporated into the joints 2900 between various cells 2004 contained within the stabilizing structure 2000, allowing for the removal of individual rows or cells to alter the shape of the stabilizing structure 2000.

Applicable to all stabilizing structures or wound closure devices described in this section or elsewhere in the specification, the stabilizing structure or wound closure device may be tearable such that the stabilizing structure may be shaped into the shape of a wound. In some embodiments, the stabilizing structure may be torn at the intersections between intervening members and elongate strips, while in further embodiments, the elongate strips or intervening members may be torn at any suitable position.

Figure 3B:
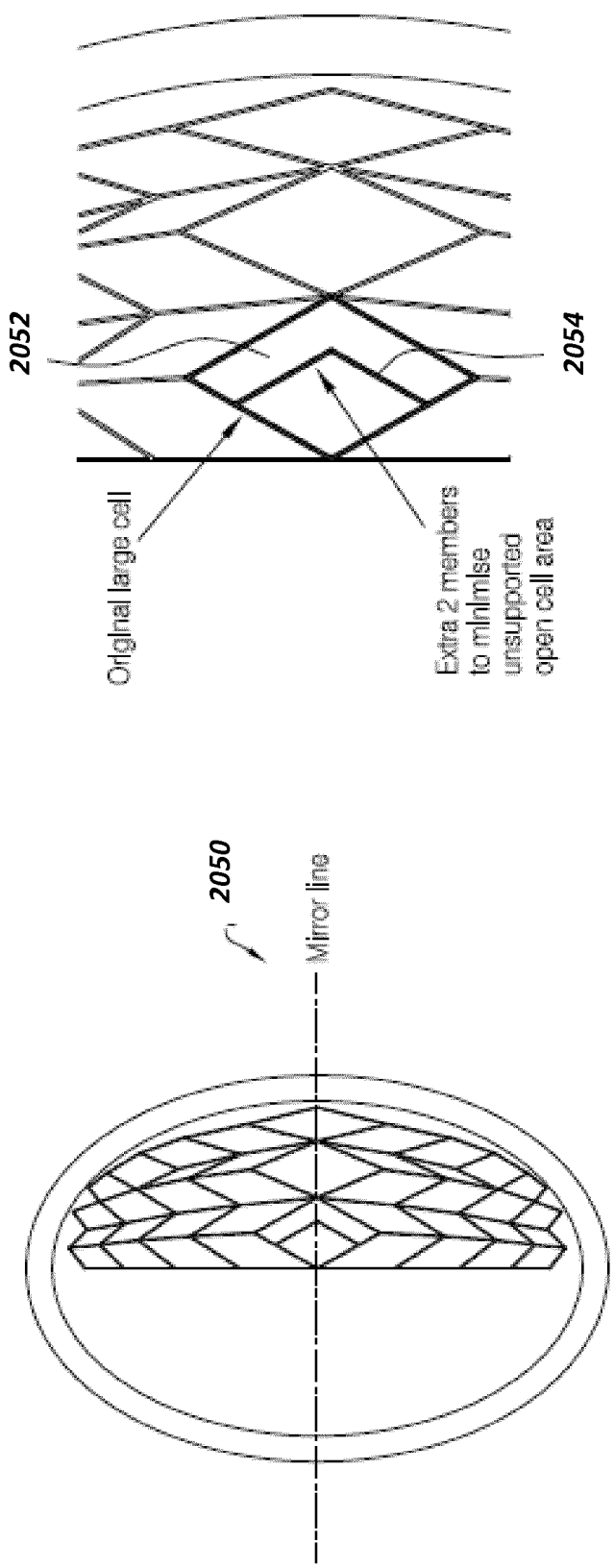

FIGS. 3A-E depict methodologies for generating the design of a stabilizing structure, such as the stabilizing structures of FIGS. 2A-C. To facilitate various types of closure (for example, maximum closure) the shape, size, and location of the elongate strips, intervening members, and cells may be determined via various methods. For example, as depicted in FIG. 3A, each collapsible cell 2030 has four sides, and each intersection between an intervening member (s) and/or elongated strip(s) may be modeled via pin-joints 2032. Further, the entirety of stabilizing structure 2034 may be modeled inside of an oval wound model 2036. As depicted in FIG. 3A, the stabilizing structure 2034 may be modeled to collapse from an open state 2038 to a semi-collapsed state 2040, to a fully collapsed state 2042. In some clinical scenarios, maximum closure down to a completely flattened stabilizing structure may be desirable to maximize wound closure by drawing the edges of the wound as close together as possible.

As illustrated in FIG. 3B, in certain embodiments, the process of determining the optimal shape, size, and location of the elongate strips, intervening members, and cells for wound closure may be facilitated by modeling the stabilizing structure as a mirrored pattern on opposite sides of a mirror line 2050 (which may also be referred to as the transverse axis, perpendicular to a longitudinal axis of the stabilizing structure), thereby making the curve and collapse of the stabilizing structure symmetrical. The mirror axis may be along the minor axis or it may be along the major axis of the stabilizing structure. Alternatively, the mirror line may be located in any suitable location within the stabilizing structure, such as diagonally across the stabilizing structure. In certain embodiments, this method may lead to large diamond-shaped cells near the center line. These large diamond-shaped structures 2052 may be further subdivided to further support the stabilizing structure by including smaller diamond shapes 2054 within larger shapes. In some embodiments, these smaller shapes 2054 within a larger shape 2052 may comprise any shape disclosed herein this section or elsewhere in the specification. The larger cells may be further subdivided by two smaller shapes, three smaller shapes, four smaller shapes, or more than four smaller shapes. It will be understood by one of skill in the art that the mirror line need not be confined to a line perpendicular to the longitudinal orientation of the wound. Instead, the mirror line may be located along the longitudinal axis of the wound or at an angle to the longitudinal axis of the wound. In some embodiments, the stabilizing structure may contain multiple mirror lines, thereby having multiple subsections that are symmetrical or different.

Figure 3C:
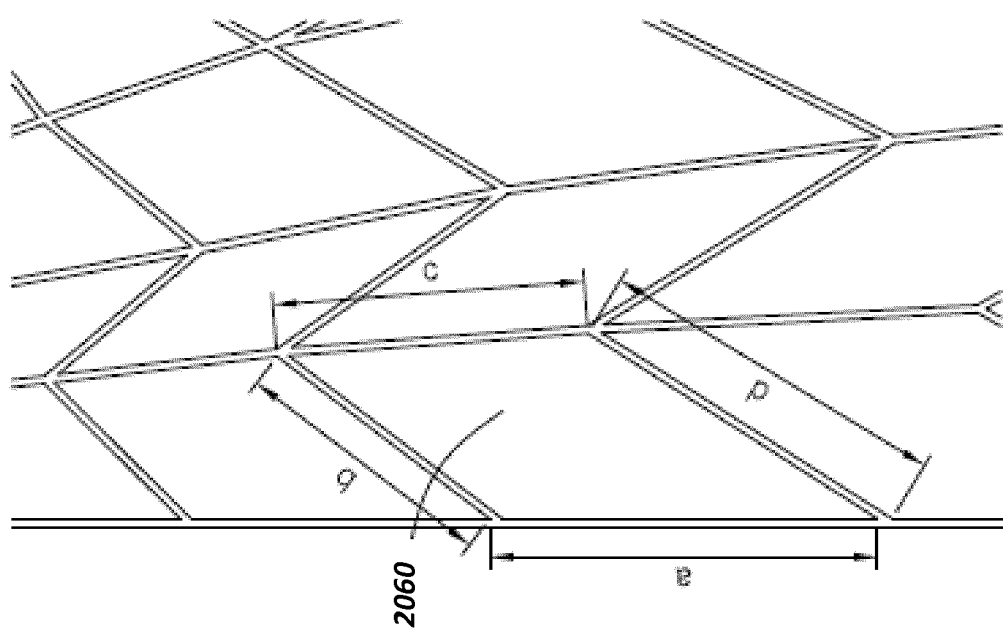

As illustrated in FIG. 3C, for a four-sided cell to collapse, it must follow a simple formula: $a+b=c+d$, where a, b, c, and d are the lengths of individual sides of a single cell within the stabilizing structure such as the cell 2060 of FIG. 3C. When members c and b collapse together, then d and a collapse together. Such a formula may be the basis for developing a pattern for a stabilizing structure that maximizes collapsibility.

Figure 3D:
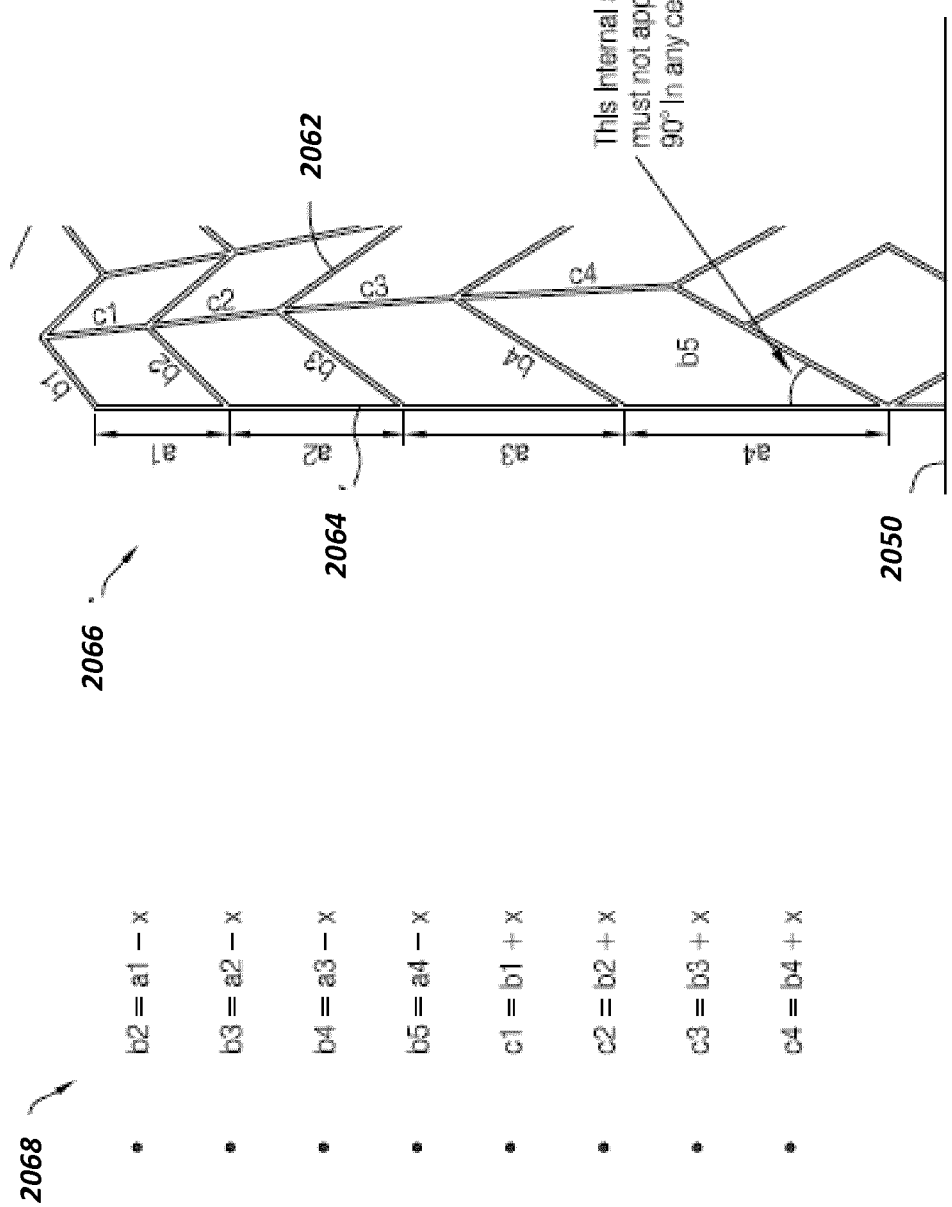
Figure 3E:
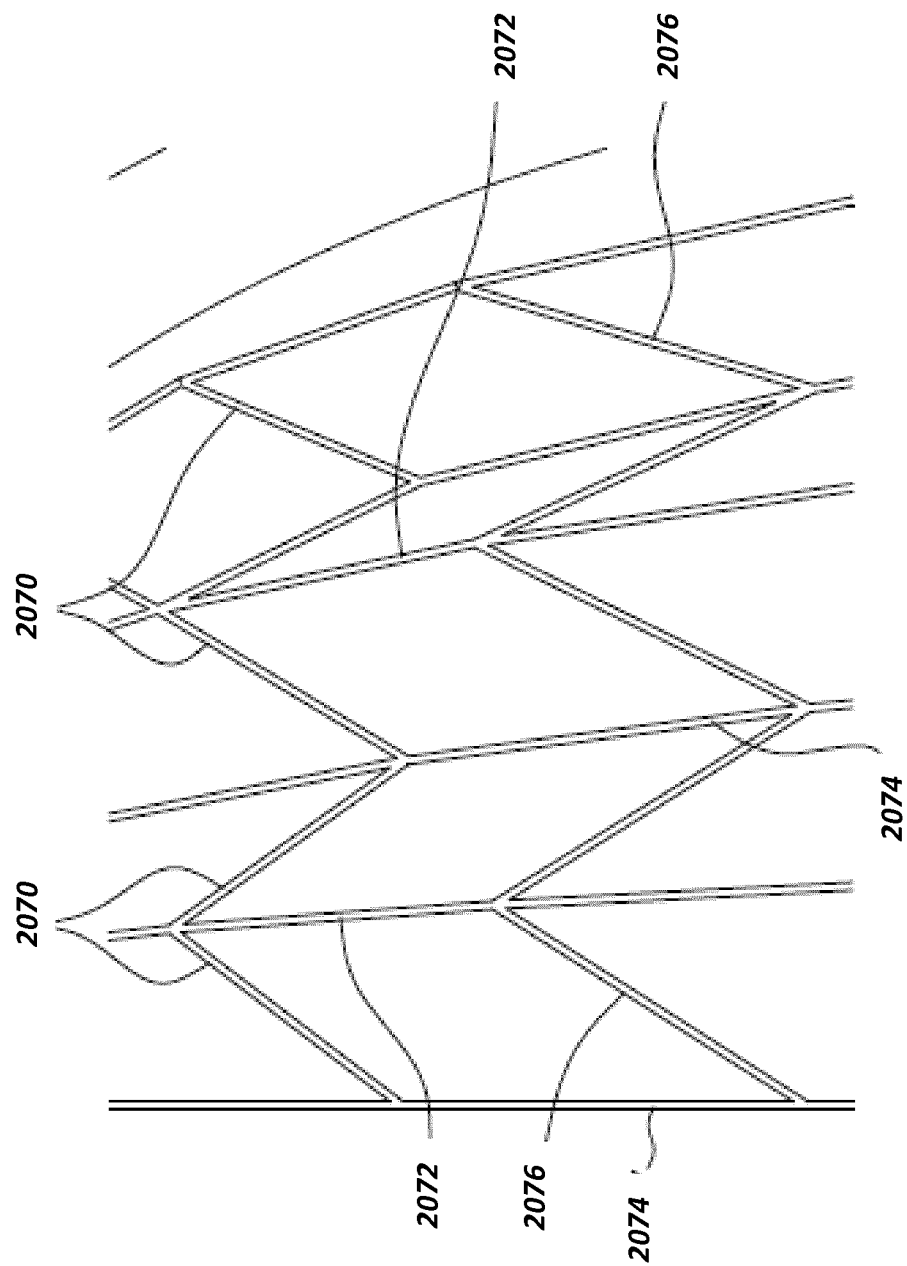

FIG. 3D illustrates an expansion of the concept described in FIG. 3C. By using the base formula $a+b=c+d$, the elongate strips were progressively lengthened ($a4>a3>a2>a1$) towards the horizontal mirror line 2050, thereby achieving a curve in the stabilizing structure while preventing any of the intervening members 2062 from becoming perpendicular to the elongate strips 2064 (i.e. having an internal angle of 90 degrees). As illustrated in FIG. 3D, a value for b1 may be chosen, at which point an arbitrary offset value x may also be chosen to ease the construction of the various cell geometries. Using the progressive values for a1 through a4, illustrated visually in FIG. 3D 2066, values for b1-b4 may be calculated 2068. Using calculated values derived from equations 2068 for the various walls of the individual cells allows for the design of a stabilizing structure that collapses completely, such as those depicted in FIGS. 3A-B.

In some embodiments, a method for generating a stabilizing structure design may include steps to speed up the initial geometry construction. For example, if all members from left to right in a specific row, as visualized by intervening members 2036 in FIG. 3E, a pattern then emerges where alternating vertical members are also the same length. Walls of the same length are indicated by their respective labels 2070, 2072, 2074, and 2076. Once the initial design is generated then individual cells may be modified by lengthening, shortening, removing or inserted according to the formulas of FIG. 3D to achieve the desired shape of the overall stabilizing structure.

Wound Closure and Treatment Methods of FIGS. 4-11G

The stabilizing structures and/or wound closure devices described in this section or elsewhere in this specification may be used in conjunction with methods or systems for the closure of a wound. In some embodiments of methods of use for closure of a wound, one or more of the stabilizing structures or wound closure devices of any of the embodiments described in this section or elsewhere in this specification is placed into a wound. In some embodiments, an organ protection layer may be provided in the wound before placement of the stabilizing structure. In certain embodiments, foam or other porous material may be placed in the wound along with the stabilizing structure or wound closure device, either below, above, or surrounding the stabilizing structure or wound closure device. Foam or other porous material may also surround the perimeter of the stabilizing structure or wound closure device. The stabilizing structure or wound closure device may be configured to collapse in any manner as described in this section or elsewhere in this specification, for example by having a particular size and shape, or by comprising a certain volume of foam or other porous material within the cells of the structure. The stabilizing structure or wound closure device may further be altered in any manner described in this section or elsewhere in this specification so as to better accommodate the shape of the wound. After placement in the wound, the stabilizing structure or wound closure device can be sealed by a fluid-tight drape. The fluid-tight drape can comprise a port configured for the application of negative pressure. A source of negative pressure may then be connected to the port and negative pressure may be applied to the wound. The stabilizing structure or wound closure device may be replaced over time by stabilizing structures or wound closure devices of various shapes and sizes as desired to best promote wound healing.

FIGS. 4-11G are photographs and illustrations depicting embodiments of methods for the treatment of a wound that utilize a wound closure device comprising a stabilizing structure as described herein this section and elsewhere in the specification. To better illustrate non-limiting embodiments of the methods, numbers have been added to the steps of FIG. 10 to allow the reader to more easily follow these steps of the method. However, the steps can be performed in any order, and any numbering system is for clarity only. Further, in some embodiments, different steps of these methods may be excluded. In other embodiments, additional steps may be added to the methods based on methods described herein this section and elsewhere in the specification. The porous layers and structures described in this section may be of any material or structure described elsewhere in the specification, such as foam.

Figure 4:
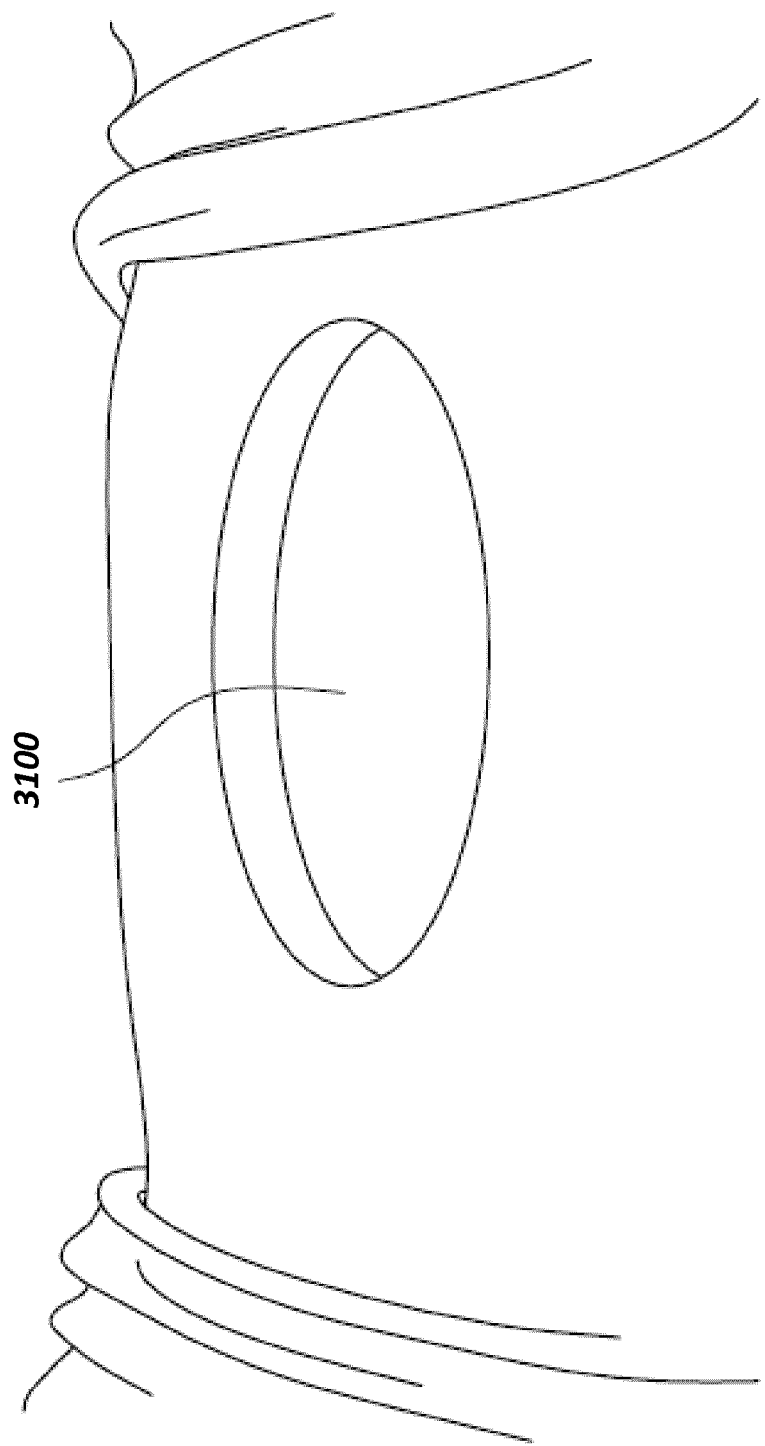
FIG. 4 illustrates an embodiment of an open abdominal wound.

FIG. 4 depicts an embodiment of an open wound 3100 prior to treatment with a wound closure device as will be described in much greater detail below. The open wound of FIG. 4 is similar to the wounds described elsewhere in the specification, particularly as relate to FIG. 1. In some instances, as described elsewhere in the specification, such a wound may be produced via a surgical incision or other means.

Figure 5:
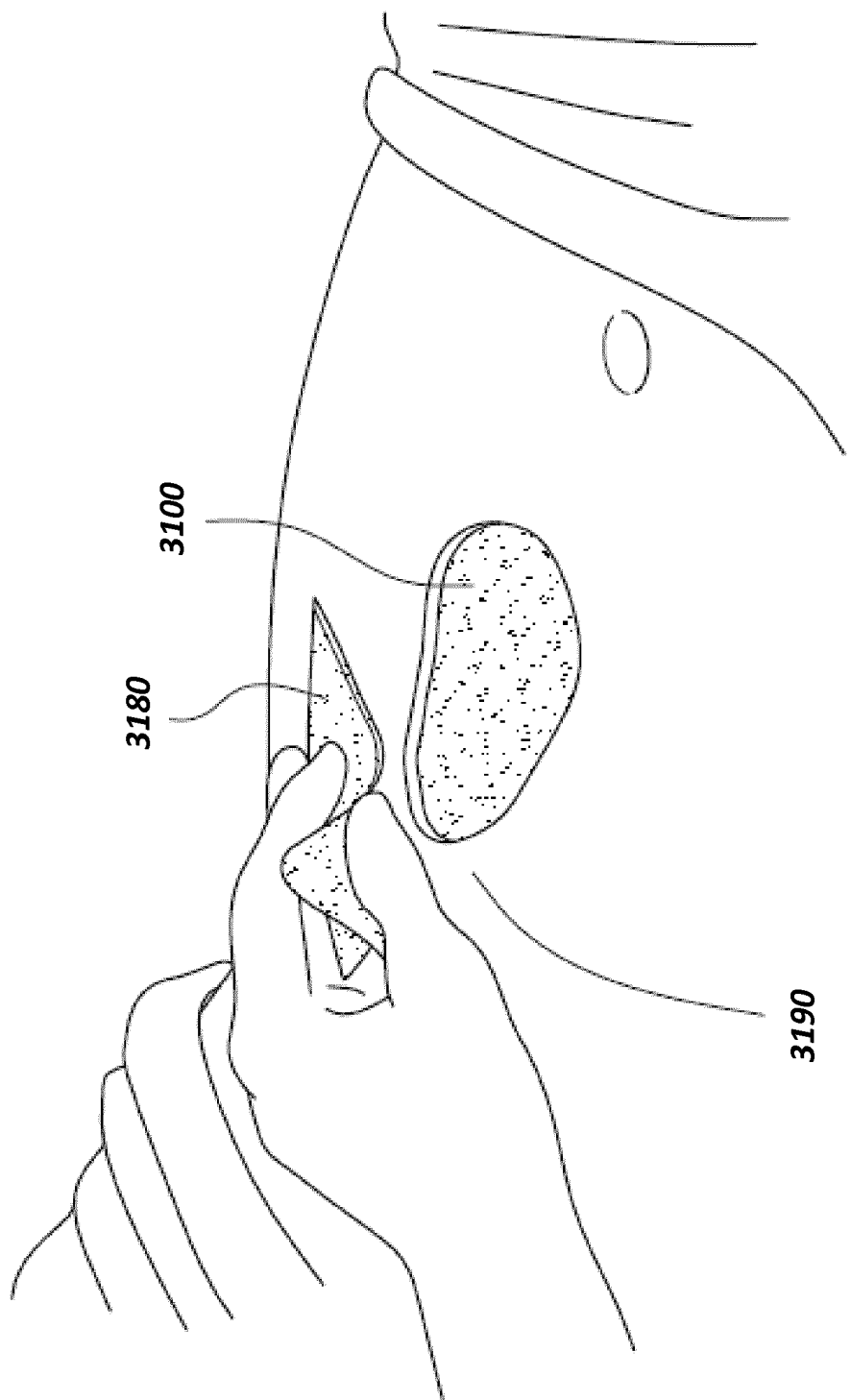
FIG. 5 illustrates an embodiment of a step in a method of treating a wound.

FIG. 5 depicts an embodiment of an initial step in a method for the treatment of an open wound 3100 with a wound closure device. Before treatment, the wound may be cleaned with a pad 3180 and the skin 3190 prepared for application of a wound closure device, such as those described in relation to FIGS. 2A-3E.

Figure 6:
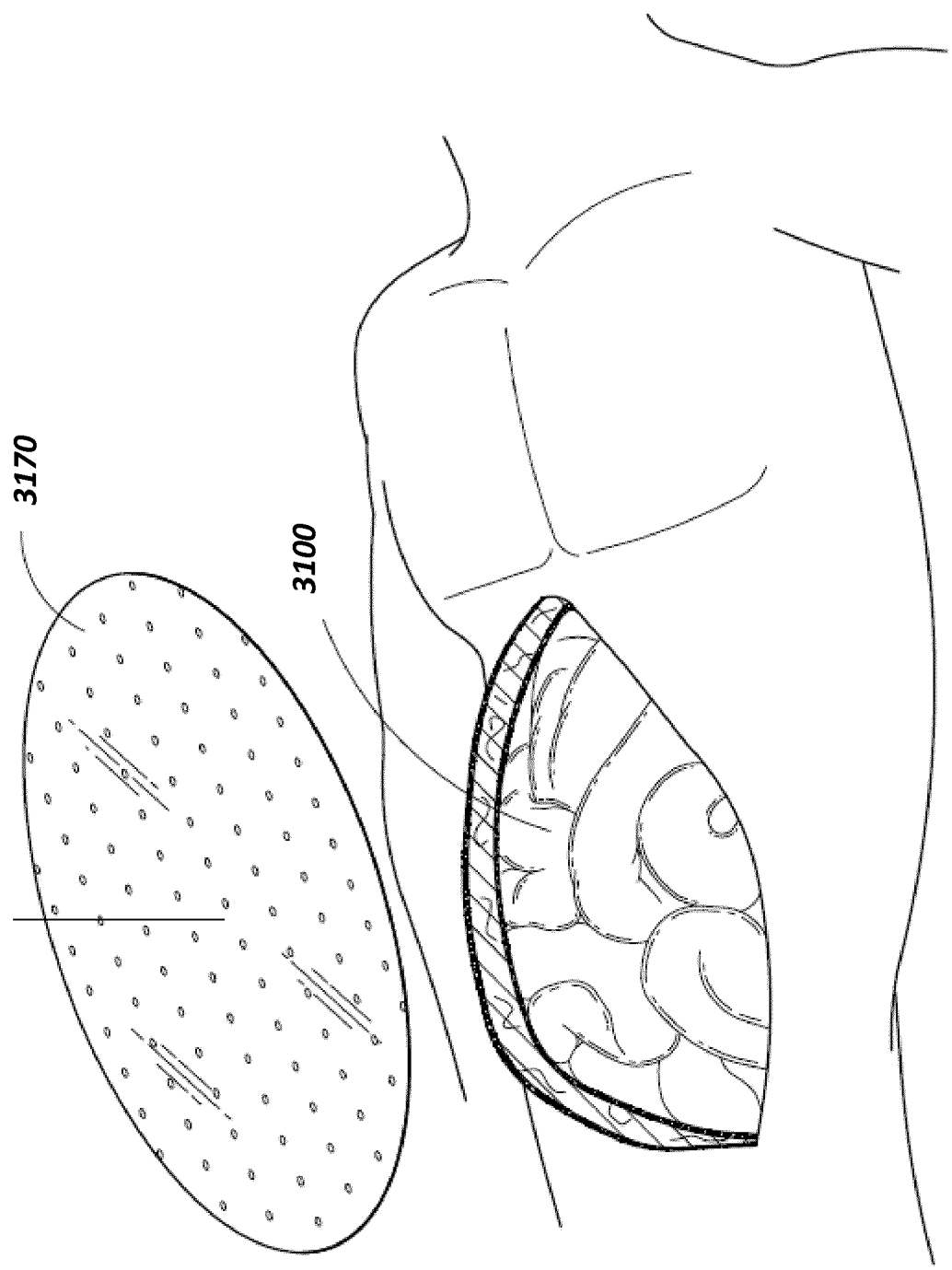
FIG. 6 illustrates an embodiment of a step in a method of treating a wound.

FIG. 6 depicts an embodiment of an early step in a method for the treatment of an open wound 3100. In some embodiments, a tissue protection layer 3170 may be placed over the wound to protect the underlying tissues from the rigors of negative pressure wound therapy or other potential harms. Accordingly, certain embodiments provide for a tissue protection layer 3170 which may be cut to size to be placed over the wound site 3100. The tissue protection layer 3170 can be a material which will not adhere to the wound site or to the exposed viscera in close proximity. Such a tissue protection layer may be constructed from any suitable material such as a biocompatible polymer. For example, organ protection layers manufactured by Smith & Nephew and sold under the brand RENASYS® may act as tissue protection layers and be placed over the abdominal cavity and/or wound bed 3100 and tucked over the peritoneal gutter. In further examples, materials such as the fluoropolymer polytetrafluoroethylene (PTFE) may be applicable as these materials are generally non-adherent and used in surgical grafts. In one embodiment, the tissue protection layer is permeable. For example, the tissue protection layer 3170 can be provided with openings, such as holes, slits, or channels, to allow the removal of fluids from the wound site 3100 or the transmittal of negative pressure to the wound site 3100. In further embodiments, the tissue protection layer may be used over non-abdominal wounds on other areas of the body, such as the leg, arm, shoulder, or back. In certain embodiments, the tissue protection layer may comprise a sensor configured to measure pressures in and around the wound. For example, the sensor may be used to measure the level of negative pressure applied to the wound or to measure the pressure on the underlying organs beneath the abdominal wound.

Figure 7A:
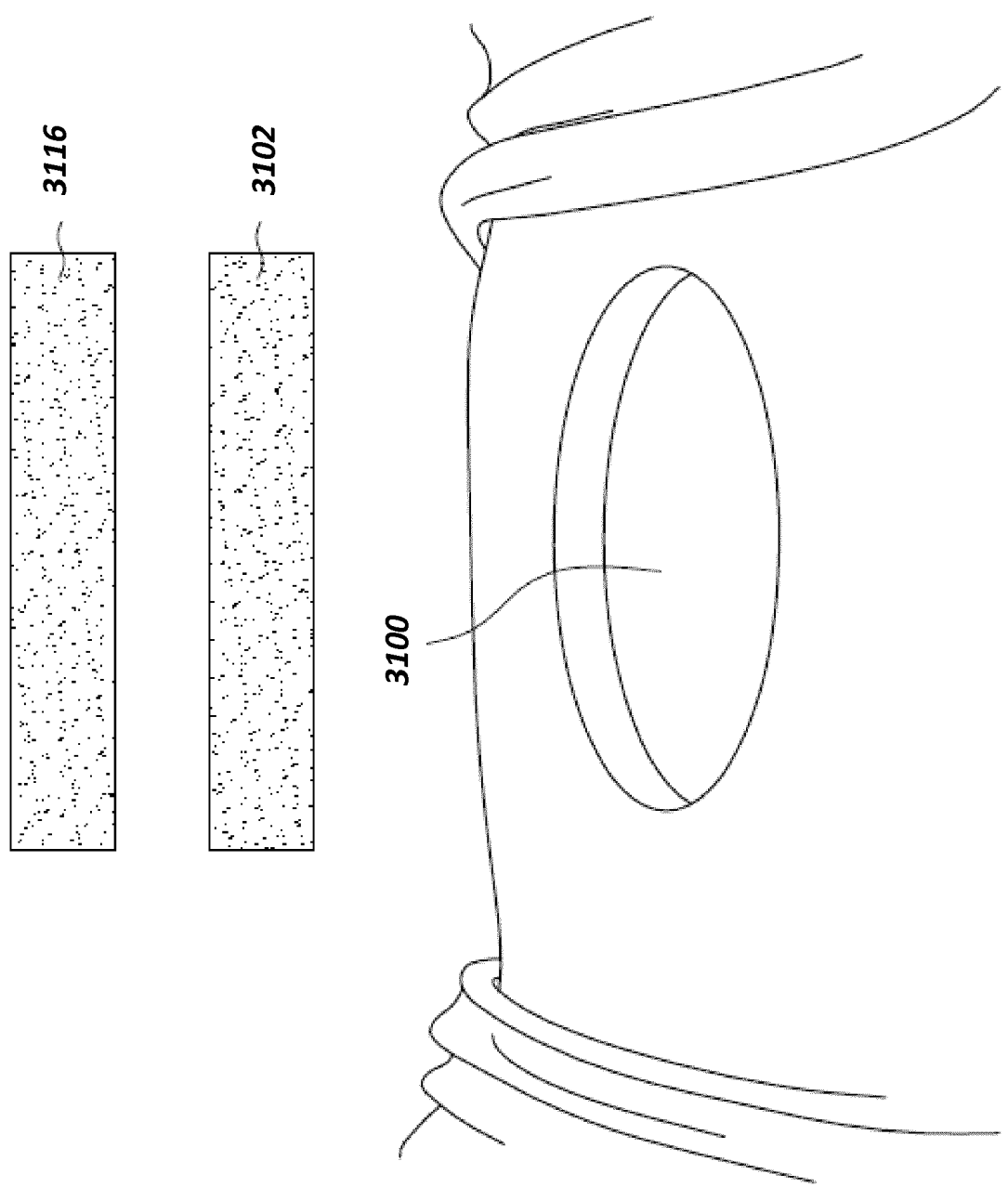
FIGS. 7A-C illustrate an embodiment of steps of a method of treating a wound.
Figure 7B:
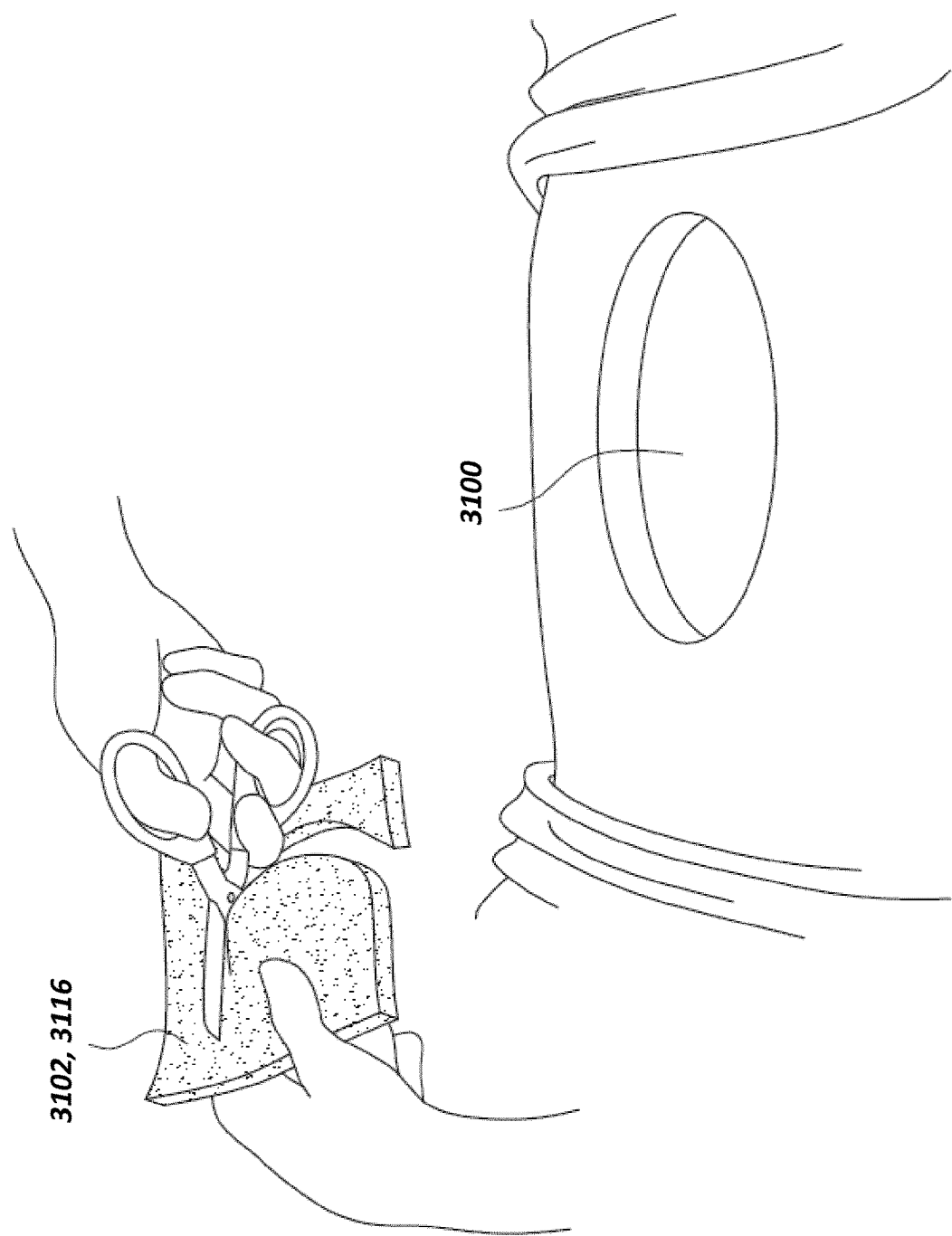
Figure 7C:
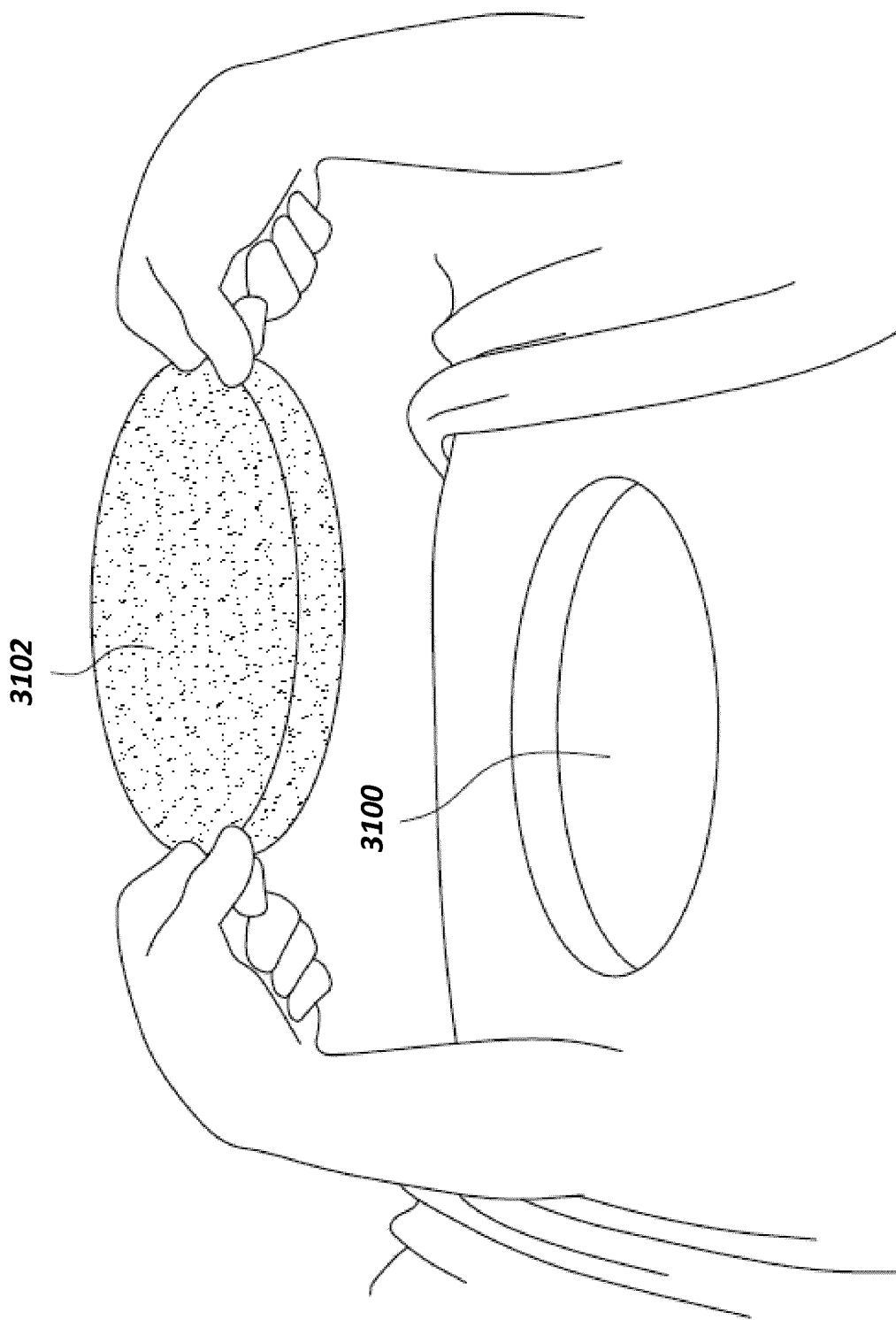

FIGS. 7A-C illustrate embodiments of possible initial steps in a method for the treatment of an open wound. However, as described above, the steps need not be performed in this order and may be performed in any order. In FIG. 7A, two pieces of a porous material such as foam, a bottom piece 3102 and a top piece 3116 are selected so as to approximate the size of the wound 3100. In some embodiments, the top piece and the bottom piece are of identical thickness. However, in certain embodiments, and vice-versa, top piece 3116 may be at least twice as thick, at least four times as thick, at least 10 times as thick or more than ten times as thick as bottom piece 3102. FIG. 7B illustrates an embodiment of additional steps in a method for the treatment of an open wound. Bottom piece 3102 may be shaped via cutting or other suitable means to the shape of the wound and subsequently placed into the wound 3100, as shown in FIG. 7C and depicted further below in FIG. 8A.

Figure 8A:
FIGS. 8A-B are photographs of steps of a method of treating a wound.
Figure 8B:
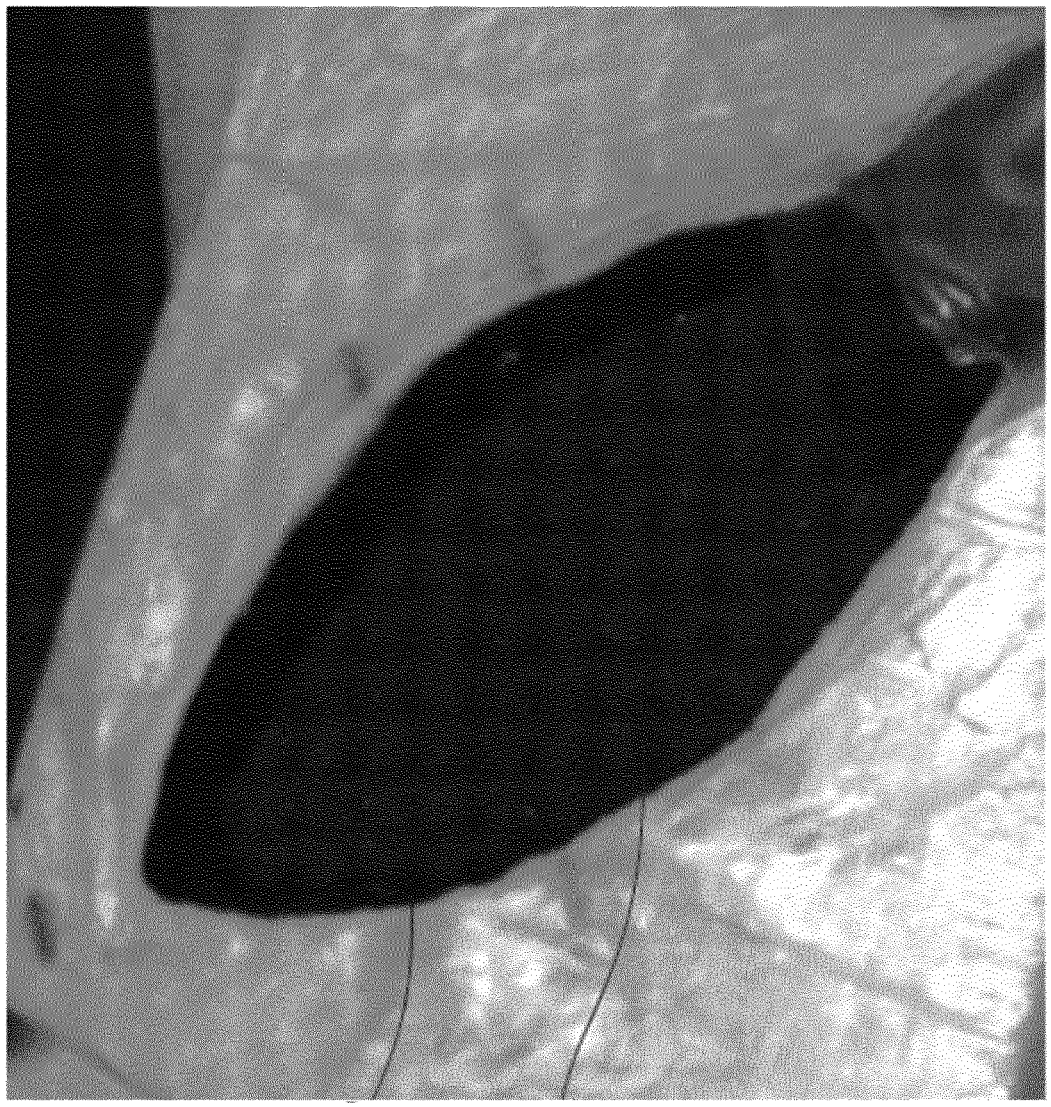
Figure 9A:
FIGS. 9A-C depict an embodiment of steps of a method of treating a wound.
Figure 9B:
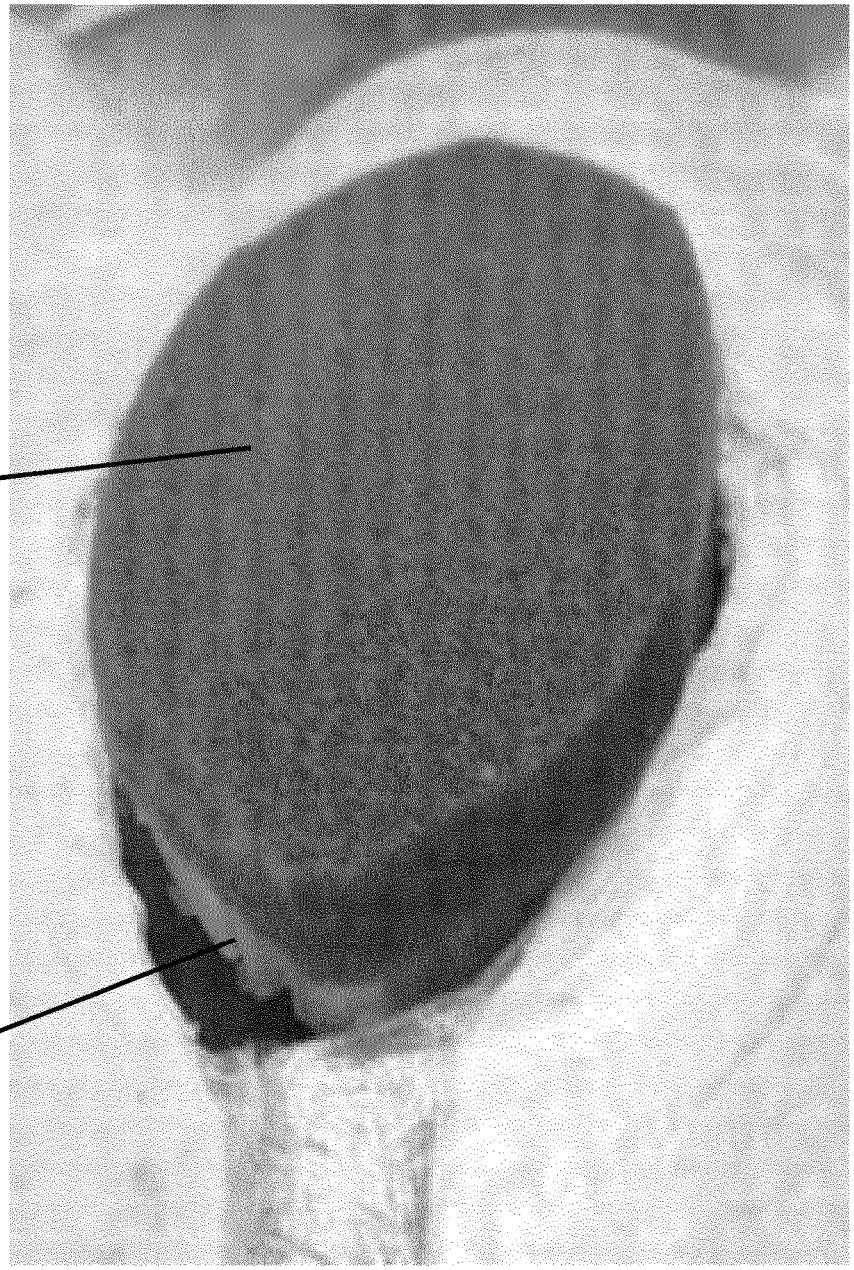
Figure 9C:
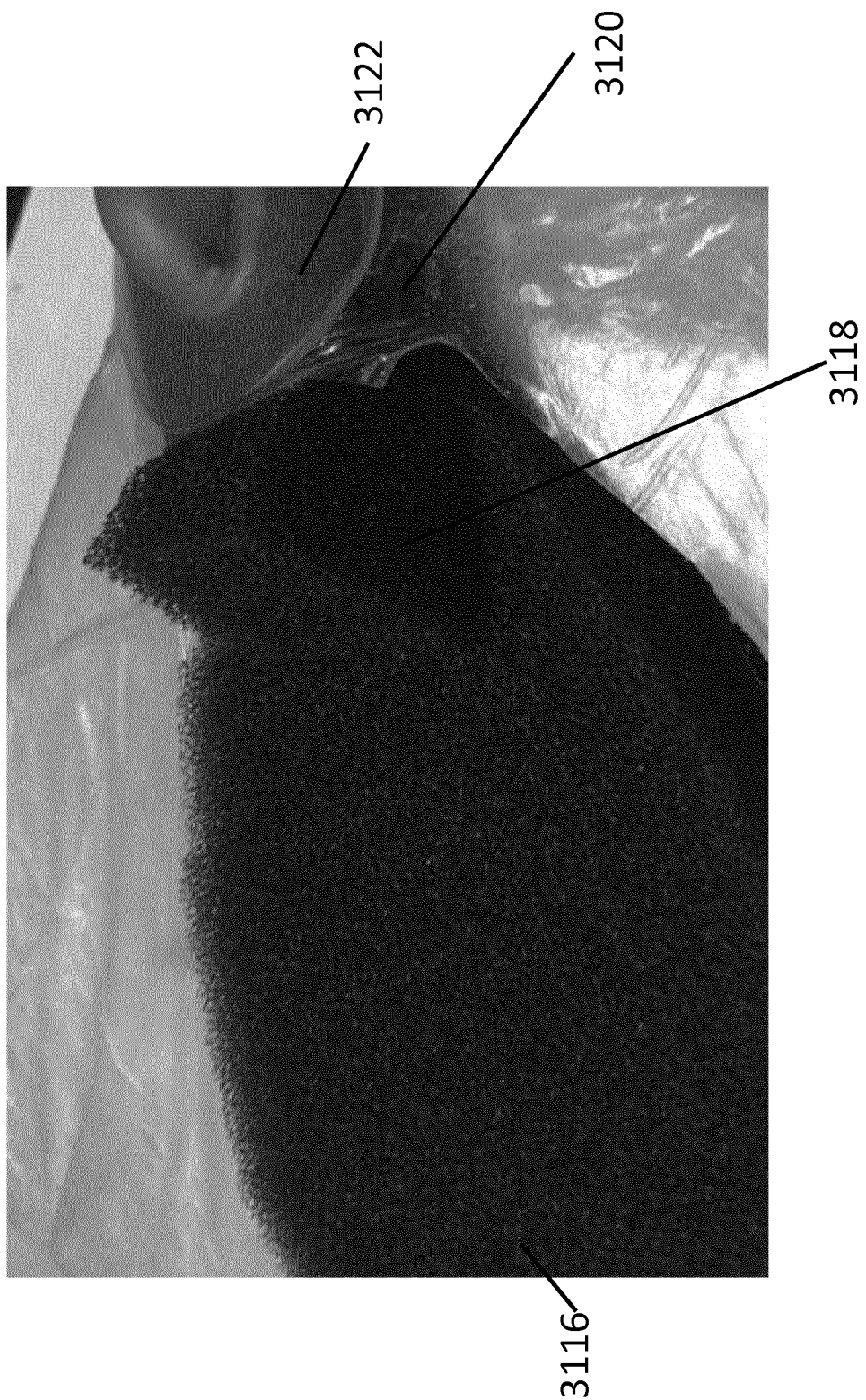

FIGS. 8A-B are photographs of a foam layer 3102 (for example, a 15 mm layer of foam), after shaping, placed into a wound bed 3100. In FIGS. 9A-C, a stabilizing structure 3104 similar to the stabilizing structures disclosed in FIGS. 2A-3E or any other stabilizing structure described elsewhere in the specification, is in the shape of the wound. The stabilizing structure may be shaped into the shape of the wound via cutting or other suitable means or the stabilizing structure may initially be of a size that is readily accommodated by the wound. As displayed in FIG. 9B, the stabilizing structure 3104 may be placed into the wound. To assist with the insertion of the device into the wound bed, the device can be deformed slightly inwardly or horizontally to facilitate entrance into the wound site. In some embodiments, the device may be squeezed slightly during insertion and then release upon contact with the walls of the wound. In certain embodiments, the wound closure device 3104 may be placed such that the longitudinal sides of the matrix align with the longitudinal axis of the wound 3100. Continuing with FIG. 9B, another foam layer 3116 (for example, a 10 mm layer of foam) is placed on top of the wound closure device 3104.

FIG. 9C is a photograph of application of a port 3122 to the stabilizing structure and foam of FIGS. 9A-B. A bridging portion of foam 3118 may be placed in intimate contact with the foam layer 3116 at the edge of the wound. The bridging portion of foam 3118 may extend over intact skin, with a piece of drape 3120 placed between it and the intact skin. Further, a suction port 3122 may be connected to the bridging portion 3118 with a section of drape 3120 between. In alternative embodiments, the bridging portion 3118 and suction port 3122 may be placed on the wound during a different step depicted in FIGS. 8A-9B.

In FIG. 10, as shown by steps 1-4, the device may be covered by one or more drapes 3120. A hole may be made in the drape covering the bridging portion of foam, and a suction port 3122 may be placed over the hole. A protective layer 3124 on the top surface of the one or more drapes may be removed after the drapes 3120 are applied. Once the drapes 3120 are applied and the port is in place, negative pressure may be applied to the wound through the drape from a vacuum source. The negative pressure can cause the stabilizing structure to collapse horizontally as described elsewhere in this specification. The tissue anchors adhered to the stabilizing structure through the porous layer engage tissue of the wound and may facilitate closure of the wound.

In certain embodiments, the suction port may be placed directly over the central portion of the foam layer 3116. In such embodiments, the foam layer may collapse inward along with the stabilizing structure while under negative pressure, thereby collapsing the suction port. To avoid collapse, the suction port may be rigid in comparison to the foam and resist collapse. A washer may be placed inside, below, or around the suction port to provide rigidity and resist collapse.

In some embodiments, the suction port may be pre-attached to the top foam layer so that drapes can be positioned around the port. A hard port or a soft port may be used, such ports may further be used in combination with a washer such as described above. In further embodiments, the suction port could only partially collapse with the collapsing matrix while still maintaining the port opening for negative pressure.

Figure 11A:
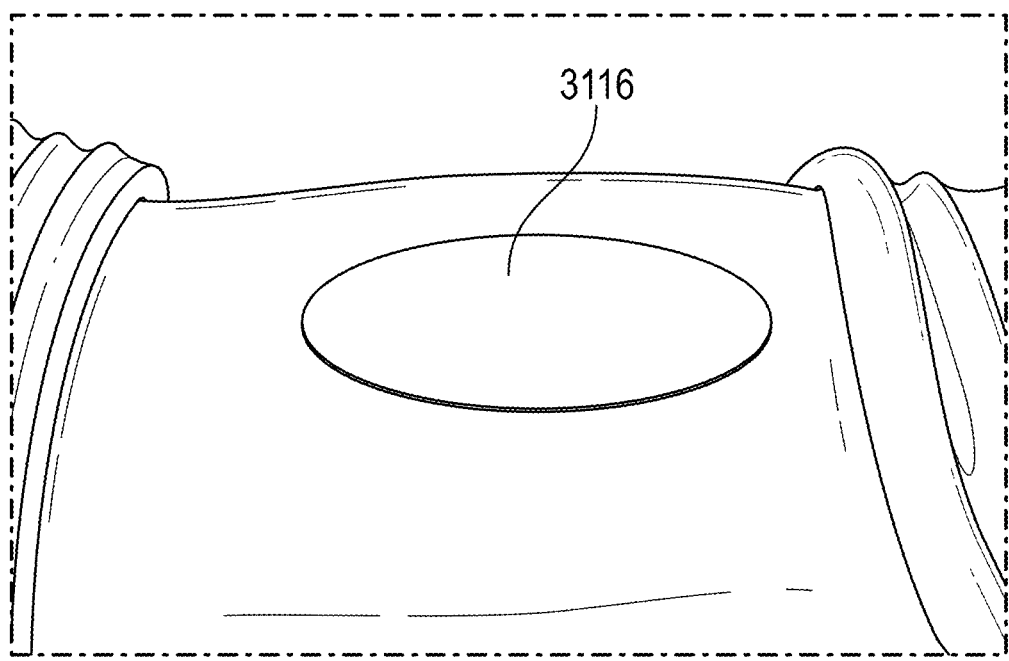
FIGS. 11A-G illustrate an embodiment of a method of treating a wound.
Figure 11B:
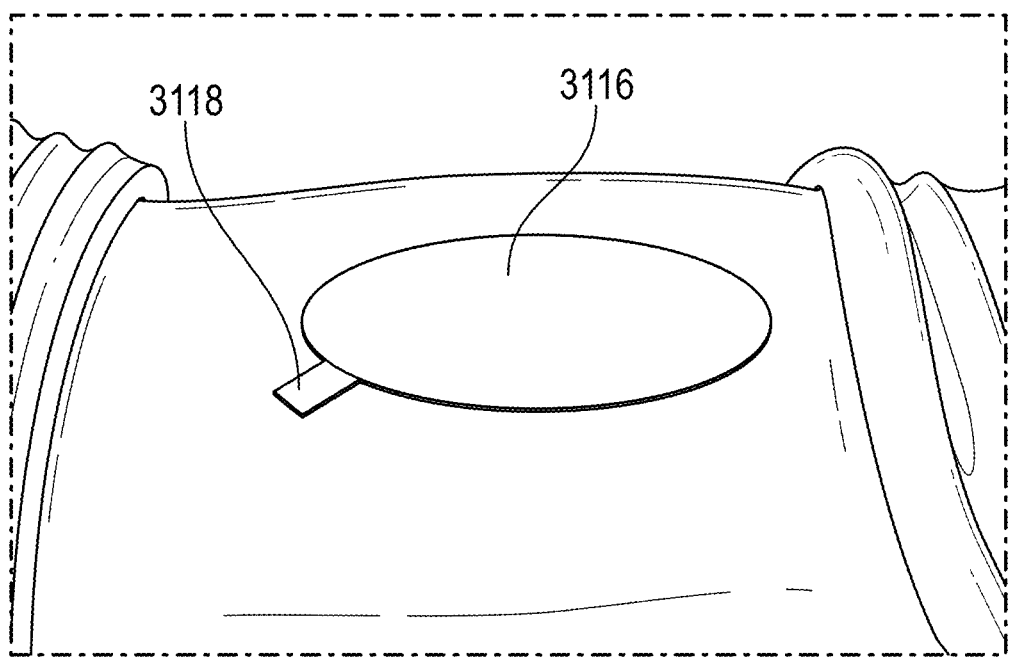
Figure 11C:
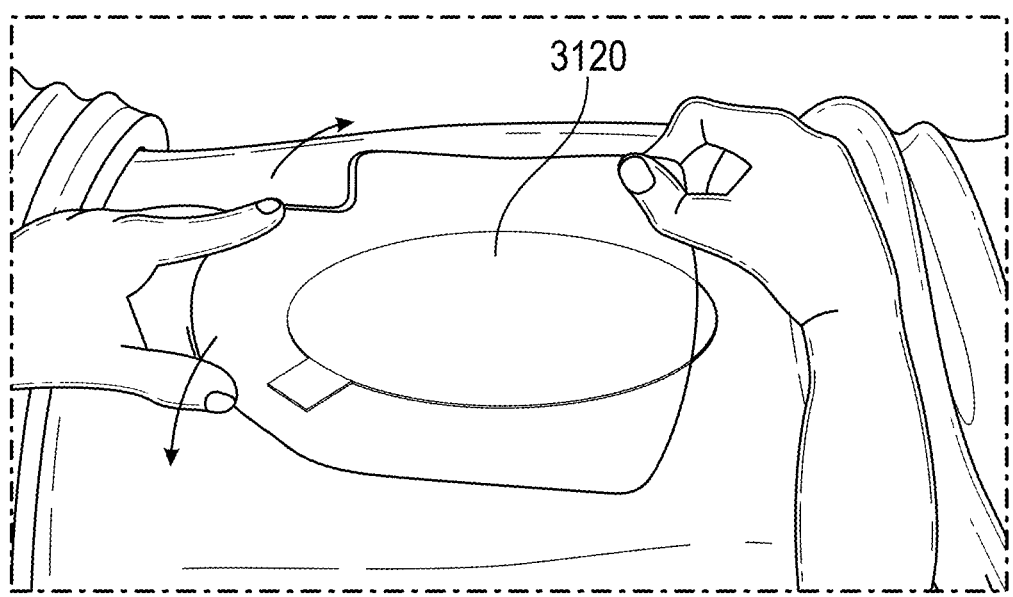
Figure 11D:
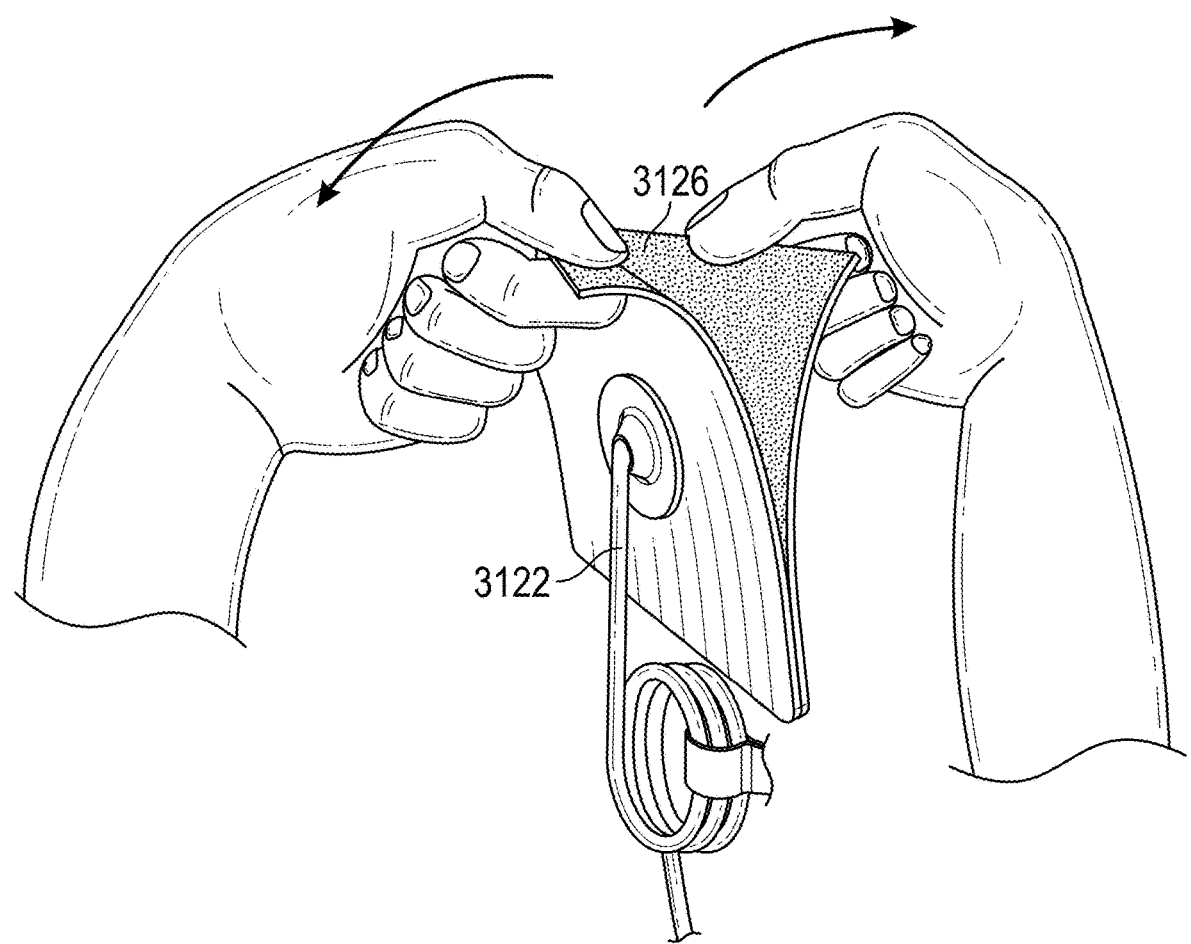
Figure 11E:
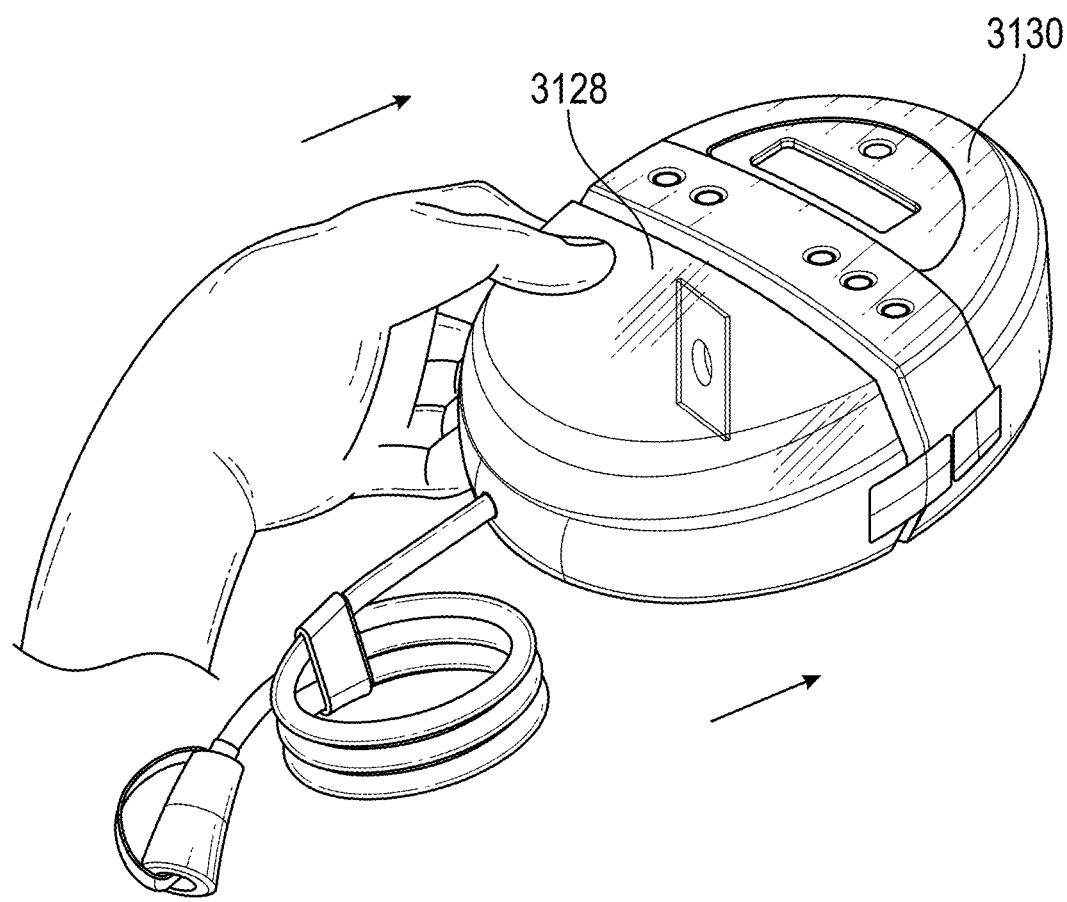
Figure 11F:
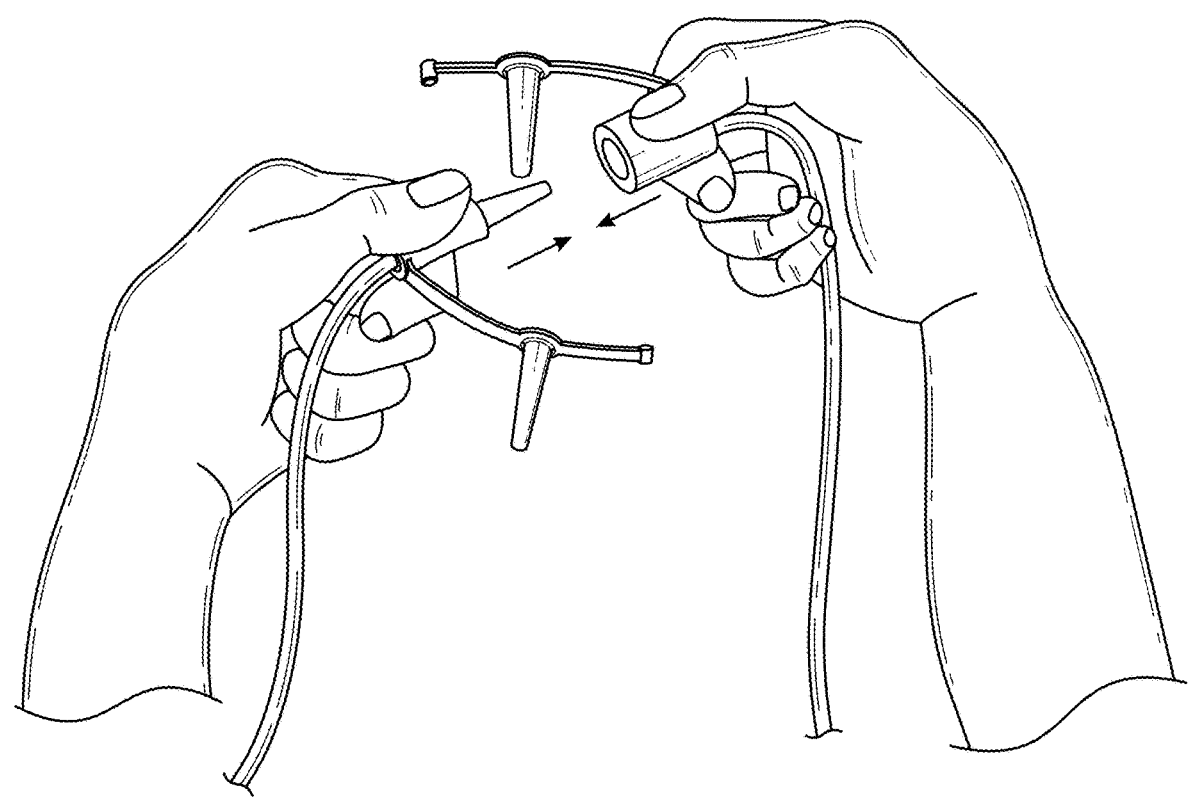
Figure 11G:
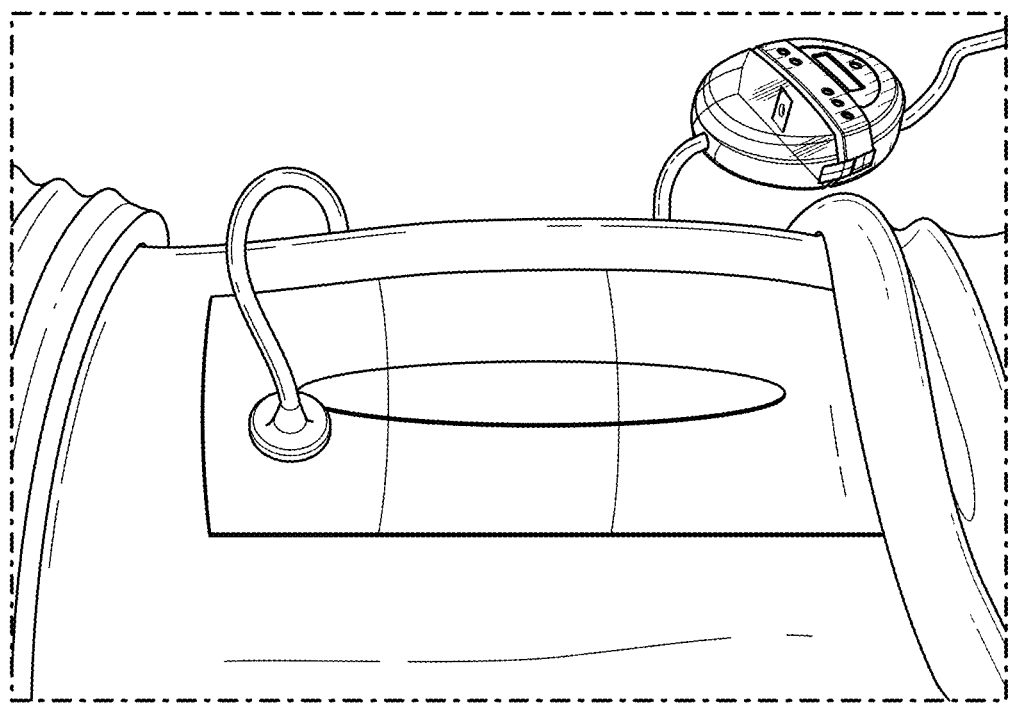

FIGS. 11A-11C provide further illustrations of an upper foam layer 3116 being placed in a wound, followed by placing a bridging portion 3118 and placing one or more drapes or wound covers 3120. FIGS. 11D-11G illustrate an embodiment of several steps in a method for the treatment and closure of a wound. As illustrated in FIG. 11D, a suction port 3122 is separated from a release liner 3126 and later applied to a wound as depicted in FIGS. 8A-10. FIG. 11E illustrates a canister 3128 being inserted into a negative pressure wound therapy device 3130 in preparation for the collection of wound exudate. FIG. 11F illustrates the snap connection between the tubing connected to the suction port and the tubing connected to the negative pressure wound therapy device 3130. Once the connection has been made, negative pressure wound treatment may begin as depicted in FIG. 11G.

Further details regarding the wound closure devices, stabilizing structures, related apparatuses and methods of use that may be combined with or incorporated into any of the embodiments described herein are found elsewhere throughout this specification and in International Application No. PCT/US2013/050698, filed Jul. 16, 2013, published as WO 2014/014922 A1, the entirety of which is hereby incorporated by reference.

Figure 12:
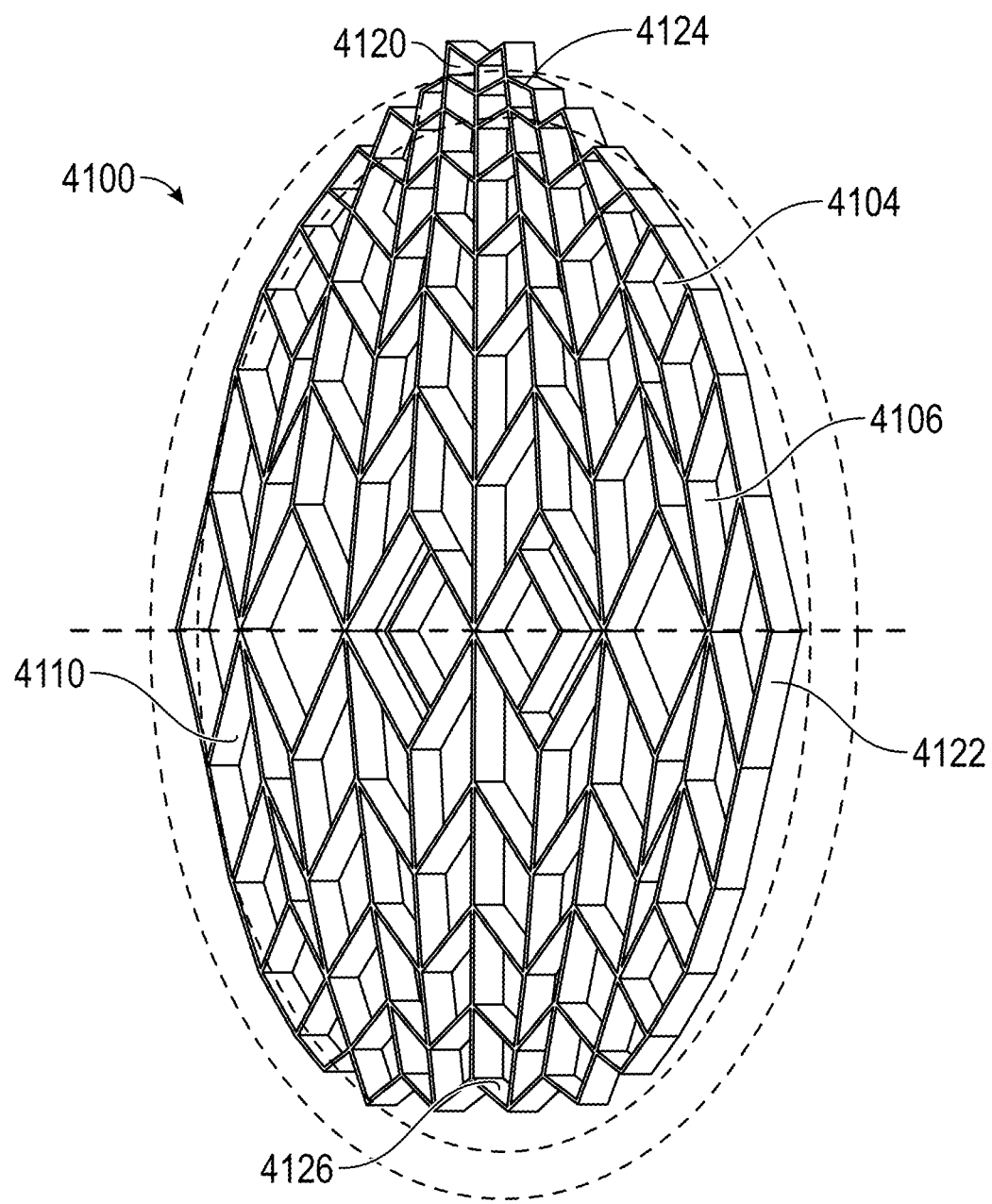
FIG. 12 illustrates an embodiment of a stabilizing structure.
Figure 13A:
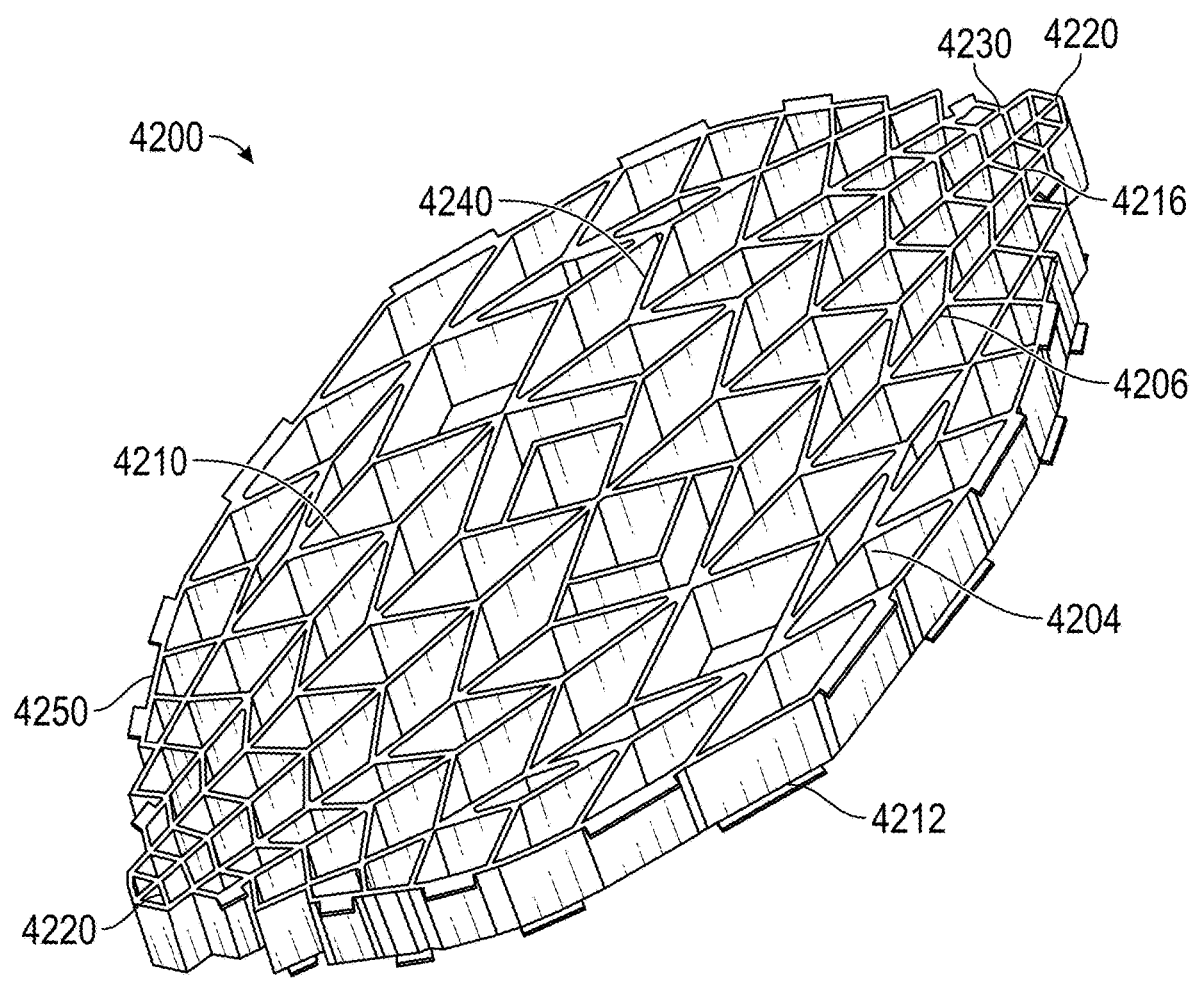
FIGS. 13A-C are drawings of an embodiment of a stabilizing structure.
Figure 13B:
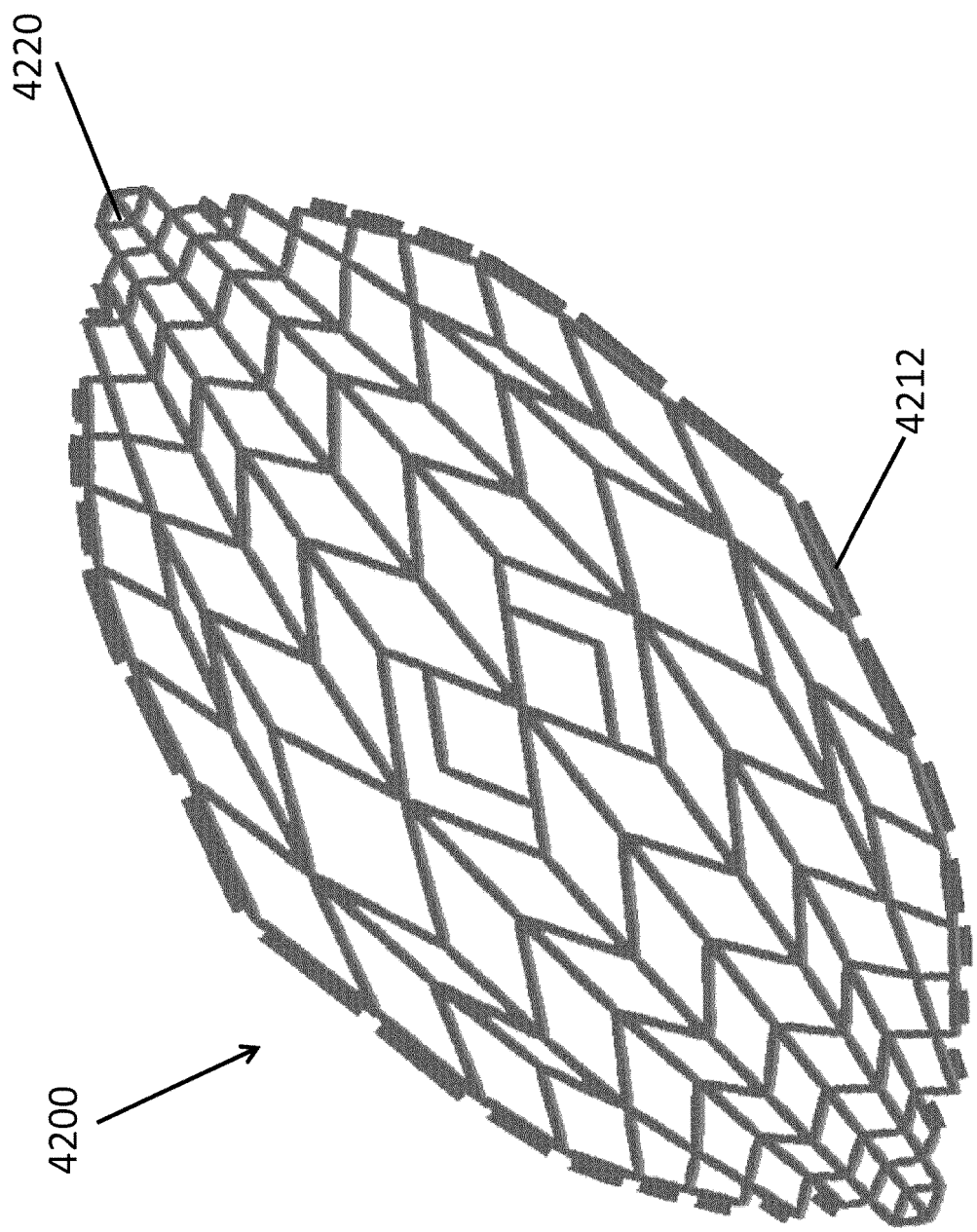
Figure 13C:
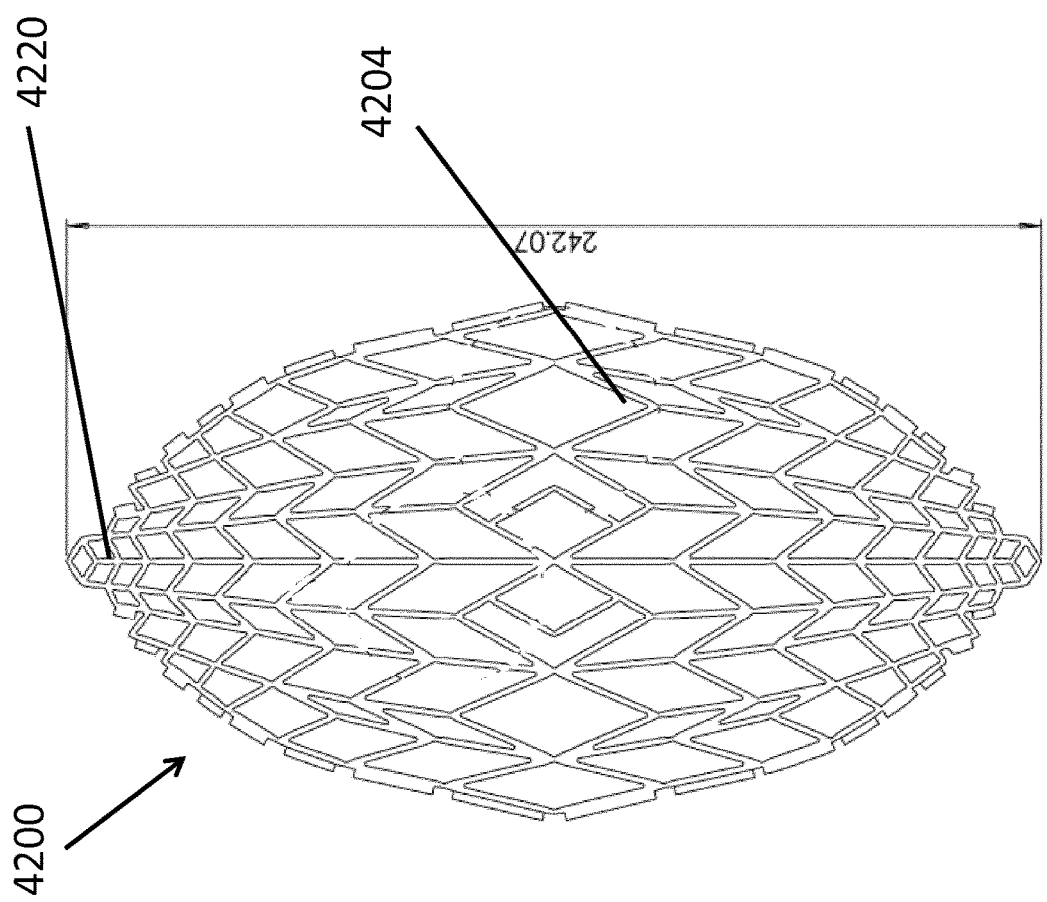

The Stabilizing Structures of FIGS. 12-13C

FIG. 12 is a drawing of an embodiment of a stabilizing structure 4100, similar to the stabilizing structures of FIGS. 2A-3E. Stabilizing structure 4100 may be constructed via any means described herein this section or elsewhere in the specification, such as via 3D printing and via the calculation method described in FIGS. 3A-3E. Further, stabilizing structure 4100 may be constructed from any material described herein this section or elsewhere in this specification such as the materials described in relation to FIGS. 2A-3E. Similar to the stabilizing structures of FIGS. 2A-3E, stabilizing structure 4100 comprises a plurality of elongate strips 4106 arranged in parallel or semi-parallel, whose longitudinal length can be aligned with the longitudinal axis of a wound. In embodiments, the elongate strips 4106 may also be arranged in a non-parallel fashion. The various cells within this stabilizing structure 4100 may have a variety of shapes and sizes. As was described in greater detail above, the length and shape of the elongate strips 4106, intervening members 4110, and cells 4104 may be designed so as to facilitate greater closure of the stabilizing structure.

In embodiments, the stabilizing structure of FIG. 12 differs from the stabilizing structures of FIGS. 2A-3E, due to the inclusion of an extended section 4120. Extended section 4120 comprises one or more additional cells that extend outward along the longitudinal axis of the stabilizing structure 4100. Extended section 4120 may allow the stabilizing structure to better fit within a long incisional wound. Further, the addition of extended section 4120 may serve to prevent pinching of the surrounding tissue during collapse of the stabilizing structure 4100. Extended section may comprise about 6 additional cell, 12 additional cells, 16 additional cells, 20 additional cells, 30 additional cells, or more than 30 additional cells.

As depicted in FIG. 12, extended section 4120 may include additional rows having progressively fewer cells across its width. For example, extended section 4120 may comprise a row of four cells, then a row of two cells, followed by another row of two cells. In some embodiments, a row of six cells precedes the row of four cells. The extended section 4120 extends beyond the outer edge of a virtual ellipse formed by the majority of the perimeter of the stabilizing structure along the longitudinal axis of the stabilizing structure. In certain embodiments, the extended section may extend from both ends of the stabilizing structure along the longitudinal axis. The extended section 4120 in some embodiments provides a stepped outer perimeter to the outer wall of the stabilizing structure at the longitudinal edges of the stabilizing structure, in contrast to the continuous outer perimeter along the sides of the stabilizing structure 4122.

Absent the extended section 4120, the stabilizing structure comprises non-stepped side walls along substantially the entire length of the oval. However, with the extended section, the additional rows may provide a stepped outer perimeter 4124 based on the additional rows, in contrast to the flattened oval end of the stabilizing structure 4126.

Further embodiments of the extended section will be described in more detail below in relation to FIGS. 13A-13C.

In some embodiments, the stabilizing structure may be in the form of two partial ellipse portions, elliptiforms, which are mirror images over a centerline of the stabilizing structure.

FIGS. 13A-13C are drawings of embodiments of stabilizing structure 4200, similar to the stabilizing structures of FIGS. 2A-3E and FIG. 12. Much like the stabilizing structures disclosed elsewhere in the specification, stabilizing structure 4200 comprises elongate strips 4206, cells 4204, and intervening members 4210. Stabilizing structure 4200 further comprises extended sections 4220 at both ends of the longitudinal axis of the stabilizing structure. As described above in relation to FIG. 12, extended sections 4220 may allow the stabilizing structure to better fit within the contours of a wound. Further, extended sections 4220 may prevent pinching of the surrounding tissue after collapse of the stabilizing structure. As described above, extended section may comprise multiple cells.

The stabilizing structures of FIGS. 13A-13C, and any of stabilizing structure disclosed herein this section or elsewhere in the specification may be produced in a variety of sizes. The possible size and shape of an actual wound may vary dramatically in size and shape, thus suitable stabilizing structures may also be prepared in a variety of sizes. For example, the length of an un-collapsed stabilizing structure may be approximately at least 25 mm, 50 mm, 75 mm, 100 mm, 125 mm, 150 mm, 175 mm, 200 mm, 250 mm, 300 mm, 350 mm, 400 mm, 450 mm, 500 mm, 750 mm, or greater than 750 mm. In certain embodiments, the width of an un-collapsed stabilizing structure may be at least 10 mm, 15 mm, 25 mm, 35 mm, 50 mm, 75 mm, 100 mm, 125 mm, 150 mm, 175 mm, 200 mm, 250 mm, 300 mm, 350 mm, 400 mm, 450 mm, 500 mm or greater than 500 mm.

As depicted in FIG. 13C, in some embodiments the un-collapsed stabilizing structure may have a length of approximately 242 mm. However, the stabilizing structure may be of any size disclosed herein this section or elsewhere in the specification. The cells 4204 of the stabilizing structure may be of a variety of sizes, for example the width of a cell 4204 may be approximately at least 5 mm, 10 mm, 15 mm, 20 mm, 25 mm, 30 mm, 50 mm, or more than 50 mm. For example, the length of a cell may be approximately at least 5 mm, 10 mm, 15 mm, 20 mm, 25 mm, 30 mm, 50 mm, or more than 50 mm.

In some embodiments, extended sections 4220 may comprise a first row of four cells, followed by a row of two cells, followed by another row of two cells. The row of four cells may be preceded by a row of six cells. However, in further embodiments, the extended section may comprise various numbers of cells per row and different numbers of rows. For example, extended section may comprise 1 row, 2 rows, 3 rows, 4 rows, 5 rows, 6 rows, or more than 6 rows. In embodiments, the rows may comprise 1 cell, 2 cells, 3 cells, 4 cells, 5 cells, 6 cells, 8 cells, 10 cells, 16 cells, or more than 16 cells.

Returning to FIG. 13A, in certain embodiments, the extended section may comprise a series of cells 4104 comprising walls that are semi-parallel 4230 to the longitudinal axis of the stabilizing structure. These cell walls contrast with cell walls elsewhere in the stabilizing structure which comprise walls that run at an angle 4240 to the longitudinal axis of the stabilizing structure 4200.

In embodiments of the stabilizing structure comprising extended sections 4220, elongate members 4206 closest to the central longitudinal axis of the stabilizing structure extend further along the longitudinal axis than embodiments of the stabilizing structure that do not comprise an extended section. For example, the innermost elongate strips are the longest strips, while the next innermost strips are the second longest and so on. The presence of the extended sections causes the stabilizing structure when viewed from above to appear to be more eye-shaped rather than more oval-shaped.

As depicted in FIG. 13A-C, in embodiments, the stabilizing structure 4200 may be oculiform. An oculiform shape may appear to be shaped like a human eye, with curved upper and lower edges converging to points at either longitudinal pole in the corners of the eye. Here, the outer walls curve inward 4250 to converge at the extended sections 4220. This shape is in contrast to a more diamond shape (not shown) where the outer walls would converge in a straight line to extended section 4220. However, in some embodiments, the stabilizing structure may be in the form of a diamond, rather than an oculiform.

Stabilizing structure 4200 further comprises tabs 4212 extended outward from the outer wall of the stabilizing structure 4200. Such tabs may extend outward from the top or the bottom of the stabilizing structure or both. The tabs may extend out from all outer cells of the stabilizing structure as depicted by FIG. 17B or the tabs may alternate as depicted in FIG. 17A. The tabs may be constructed from any material described herein this section or elsewhere in the specification, such as those materials used for construction of the stabilizing structures. In certain embodiments, the tabs may be 3D printed as part of the stabilizing structure.

The tabs 4212 may further comprise an anchoring layer which may be used to adhere the tabs to a layer of foam. In embodiments, the tabs may be coated in a suitable adhesive, allowing the tabs to be adhered to a layer of foam. The attachment of foam to the upper and lower layers of the stabilizing structure will be described in greater detail below in relation to FIG. 14A-14D. The tabs may further serve to extend outward above or below tissues surrounding the stabilizing structure or around other structures such as foam, wrapped around the perimeter of the stabilizing structure.

The stabilizing structures of FIGS. 13A-13C may be provided in a variety of sizes such as those described above in relation to FIGS. 2A-3E. As described above, it may be advantageous in a clinical setting to minimize adjustments to the size of the stabilizing structure, therefore a kit may be provided that includes stabilizing structures of various sizes that may be fit to a wound of the appropriate size. For example, the kit may comprise only two sizes of matrices, a large size and a small size. The larger size stabilizing structure may be at least about 1.25×, 1.5×, 1.75×, 2×, 2.5×, 3×, 4×, 5×, 6× or greater than 6 times the size of the smaller stabilizing structure.

The Stabilizing Structures and Foam Layers of FIGS. 14A-14D

FIGS. 14A-14D are drawings and photographs of foam layers in combination with stabilizing structures such as those described above in relation to FIGS. 2A-3E and 12-13C. The foam layers described below may include any type of foam described herein this section or elsewhere in the specification. Possible foams may include open-celled and/or reticulated foams made from a polymer. Suitable foams include foams composed of, for example, polyurethane, silicone, hydrophobic materials, hydrophilic materials, open-celled materials, close-celled materials, mixed open and close-celled materials, reticulated materials, polyester, silicone, and/or polyvinyl alcohol. In embodiments, the foam layers described herein may include materials that change their properties over time. For example, a particular foam may be rigid initially but become more flexible when wet and/or lose rigidity over time due to degradation of the material.

The foam layers described in this section or elsewhere in the specification may have a variety of suitable thicknesses. For example, a foam layer may have a thickness of at least about 1 mm, 3 mm, 5 mm, 10 mm, 15 mm, 20 mm, 25 mm, 30 mm, 35 mm, 40 mm, 45 mm, 50 mm, or more than 50 mm thick. Single layers of foam may be laid atop one another to create a greater total thickness of foam, for example, a 15 mm thick layer of foam may be laid atop a 10 mm layer of foam to create a 25 mm total thickness of foam.

In certain embodiments, any of the foam layers described herein this section or elsewhere in the specification, may be pre-attached to an organ protection layer such as described above. For example, the lowest layer of foam, closest to the underlying organs, may be attached to an organ protection layer before placement within the wound, thereby saving the clinician the step of first placing an organ protection layer within the wound. In certain embodiments, the organ protection layer may be pre-attached to the underside of a stabilizing structure such as those described herein this section or elsewhere in the specification. In embodiments, the organ protection layer may be attached to the top of the bottom-most foam layer placed in the wound, thereby positioning the organ protection layer between the stabilizing structure and the bottom-most layer of foam. The organ protection layer may completely encase the bottommost layer of foam or stabilizing structure. The presence of a bottom layer of foam and/or organ protection layer may serve to protect the underlying bowel from damage due to direct interaction with the stabilizing structure.

Figure 14A:
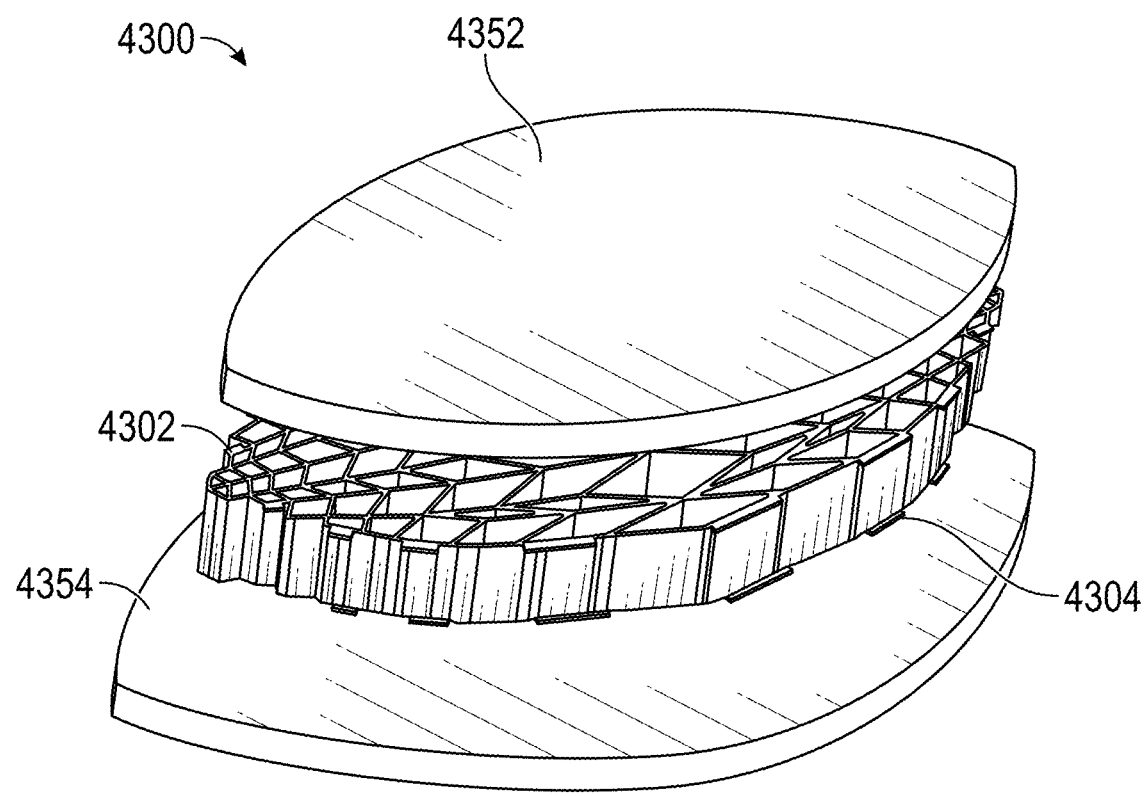
FIGS. 14A-D illustrate embodiments of stabilizing structures and foam layers.
Figure 14B:
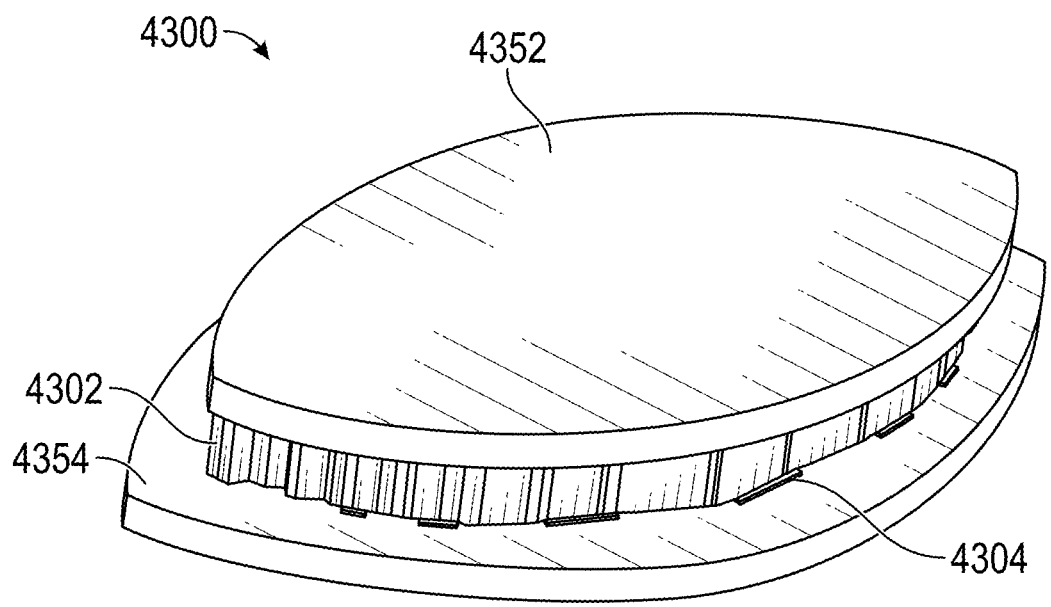
Figure 14C:
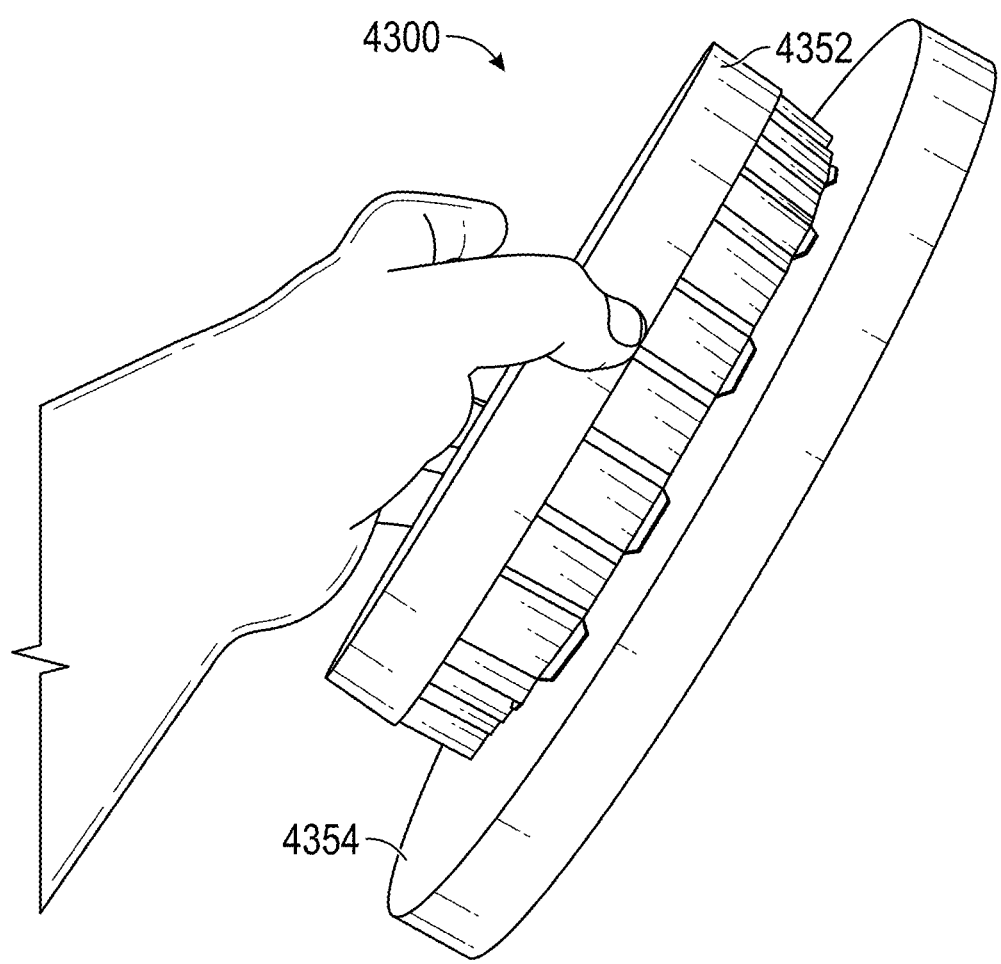

FIGS. 14A-B are drawings and photographs of embodiments of a wound closure device 4350 comprising a stabilizing structure 4302 (similar to the stabilizing structures described above in relation to FIGS. 2A-3E and 12-13C), a top porous foam layer 4352, and a bottom porous foam layer 4354. As will be described in greater detail below, top and bottom porous layers 4352 and 4354 may be shaped in any desired manner to conform to the shape of stabilizing structure 4302. In embodiments, the top and bottom layers of foam may be attached to the stabilizing structure 4302 before placement in the wound. Pre-attachment of the foam layers advantageously reduces the number of steps that need to be completed by the clinician.

As described elsewhere in the specification, stabilizing structure 4302 may comprise tabs 4304. These tabs advantageously provide a larger surface area for attachment of the foam layers to the stabilizing structure. Without the tabs, adhesive would necessarily need to be applied to the narrow upper edges of the stabilizing structure, potentially creating a weak or non-existent attachment. As described above, the tabs may be located on the top and bottom edges of the stabilizing structure. In embodiments, rather than adhesive, the tabs may be covered in anchors, which may act much like the adhesive, allowing the foam layers to be attached to the stabilizing structure prior to placement in the wound. The stabilizing structure may be pre-attached to the bottom layer of foam, top layer, or both. In certain embodiments, the adhesive may be applied to the central longitudinal elongate member of the stabilizing structure rather than to the tabs or other location. By applying adhesive only to the central elongate member, the stabilizing structure may collapse without resistance from the foam.

FIGS. 14A-B show embodiments of wound closure devices where the bottom foam is larger than the top foam, either by width, length, or both. Here, the foam extends outward from the stabilizing structure to create a lip, thereby allowing the lip of foam to extend above or below the surrounding tissue layers such as the fascia. The lip may serve to maintain the stabilizing structure in place by providing a downward force to resist the upward force applied by the expanding underlying viscera. In certain embodiments, the lip may need to be folded during placement within the wound bed so as to allow the closure device to be properly positioned. Thereafter the lip may unfold and extend into the surrounding tissues to aid in securing the device and applying negative pressure to the surrounding tissues.

The top layer may be sized to the top of the stabilizing structure, thereby facilitating closure of the wound to the size of the collapsed stabilizing structure. The lip extending outward from the matrix may be rounded so as to provide a better fit within the wound. In contrast, in the embodiment of FIG. 14C, the bottom layer may be smaller than the top layer. The top layer may advantageously prevent drawing of the drape down into the stabilizing structure or between the stabilizing structure and the edges of the wound.

In certain embodiments, the foam layers may be of any thickness disclosed herein this section or elsewhere in the specification. The bottom layer of foam 4354 may be approximately 15 mm thick or approximately 10 mm thick. For example, the bottom foam 4354 of FIG. 14B may be thicker than the bottom foam of FIG. 14B.

Figure 14D:
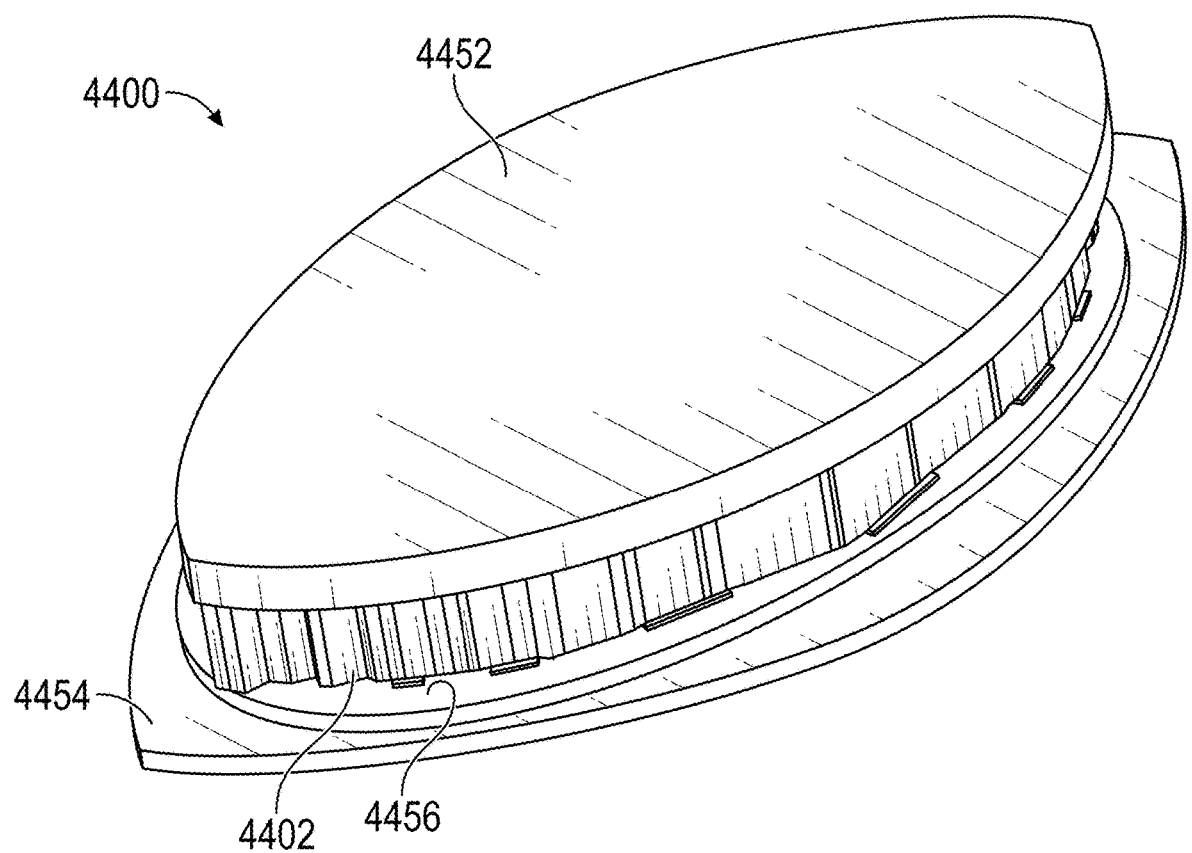

FIG. 14D depicts an embodiment of a wound closure device involving a total of 3 layers of foam. Here, wound closure device 4400 comprises stabilizing structure 4402, top layer of foam 4452, bottom layer of foam 4454, and middle layer of foam 4456. The stabilizing structure may be pre-attached to the middle layer of foam, top layer of foam, or both. Further, the bottom layer of foam may be pre-attached to the middle layer of foam, or may be placed into the wound separately. In some embodiments, the top layer is 15 or 10 mm thick, the middle layer is 15 mm thick, and the bottom layer is 10 mm thick. Foam layers may be attached by any suitable means, such as via adhesive or anchors. As depicted in FIG. 14D, the bottommost layer of foam may comprise a lip that extends outward from the wound closure device into the surrounding tissue. As described above, such a lip may secure the device in place. The bottom layer of foam may be wider and/or longer than the middle and/or top layers of foam. In certain embodiments, in addition to the foam on the top and bottom of the stabilizing structure, foam may be attached to the entire outer perimeter of the stabilizing structure. Foam may be attached to the perimeter of the stabilizing structure via any suitable means, such as by adhesive or anchoring layer. Once foam has been applied to the perimeter of the stabilizing structure, the stabilizing structure will no longer be visible if there are also top and bottom layers of foam.

In embodiments of the foam layers of FIGS. 14A-14D, the layers of foam may comprise any type of suitable foam material described herein this section or elsewhere in the specification. For example, the foam may comprise "black foam" such as polyurethane and/or "white foam" comprising polyvinyl alcohol (PVA). In embodiments involving PVA foam, thinner foam layers may be needed as compared to other types of foam, because PVA foam is often more resilient and dense than other types of foam. Further, once PVA foam becomes wet it may also aid with lateral slip. In some embodiments, the foam layers may be combined with other fillers such as gauze, or other mesh/net products such as those on Fry and Kossel.

The Stabilizing Structures and Foam Layers of FIGS. 15A-16E

Figure 15A:
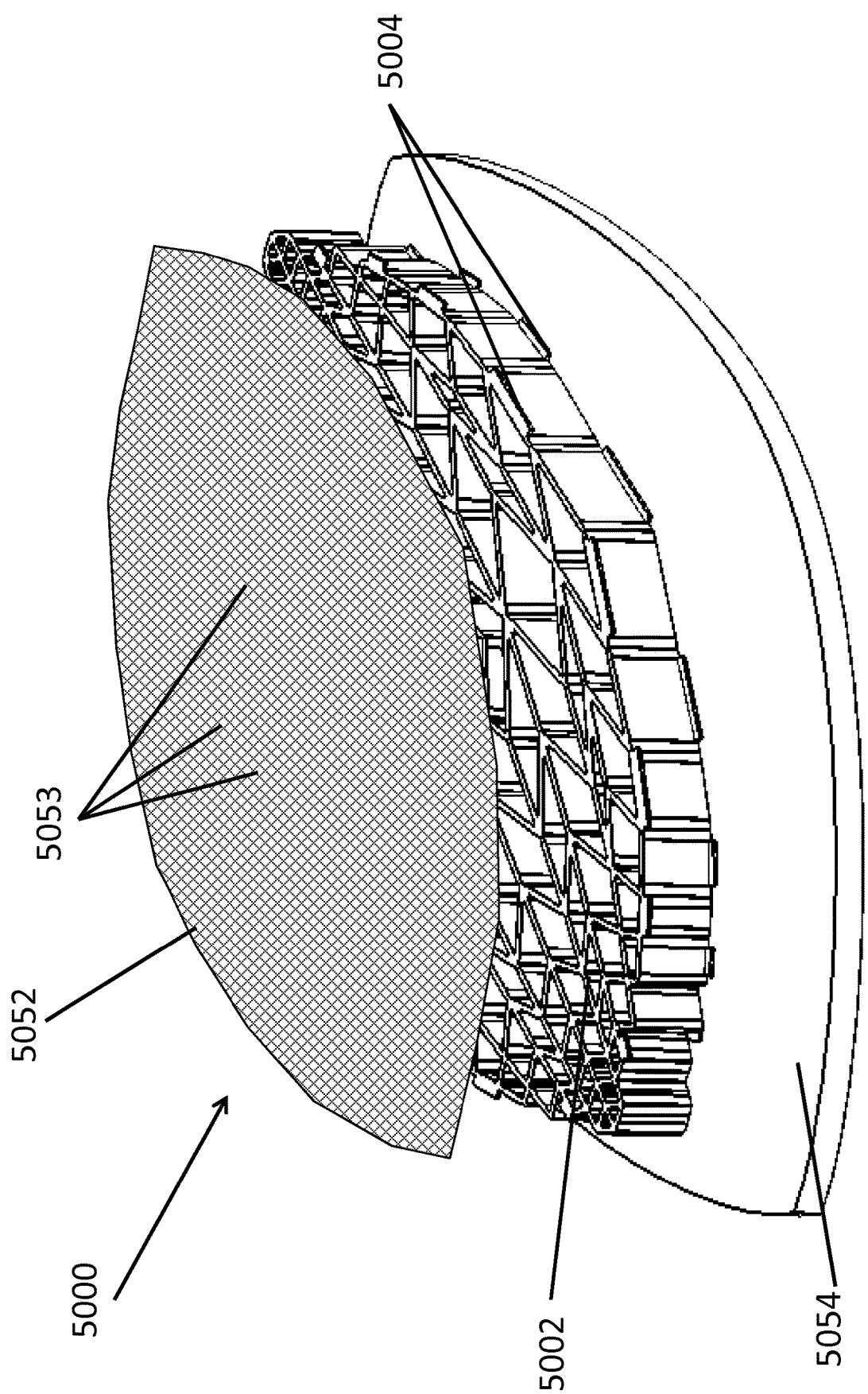
FIGS. 15A-B illustrate an embodiment of a stabilizing structure with a protective layer and a foam layer.
Figure 15B:
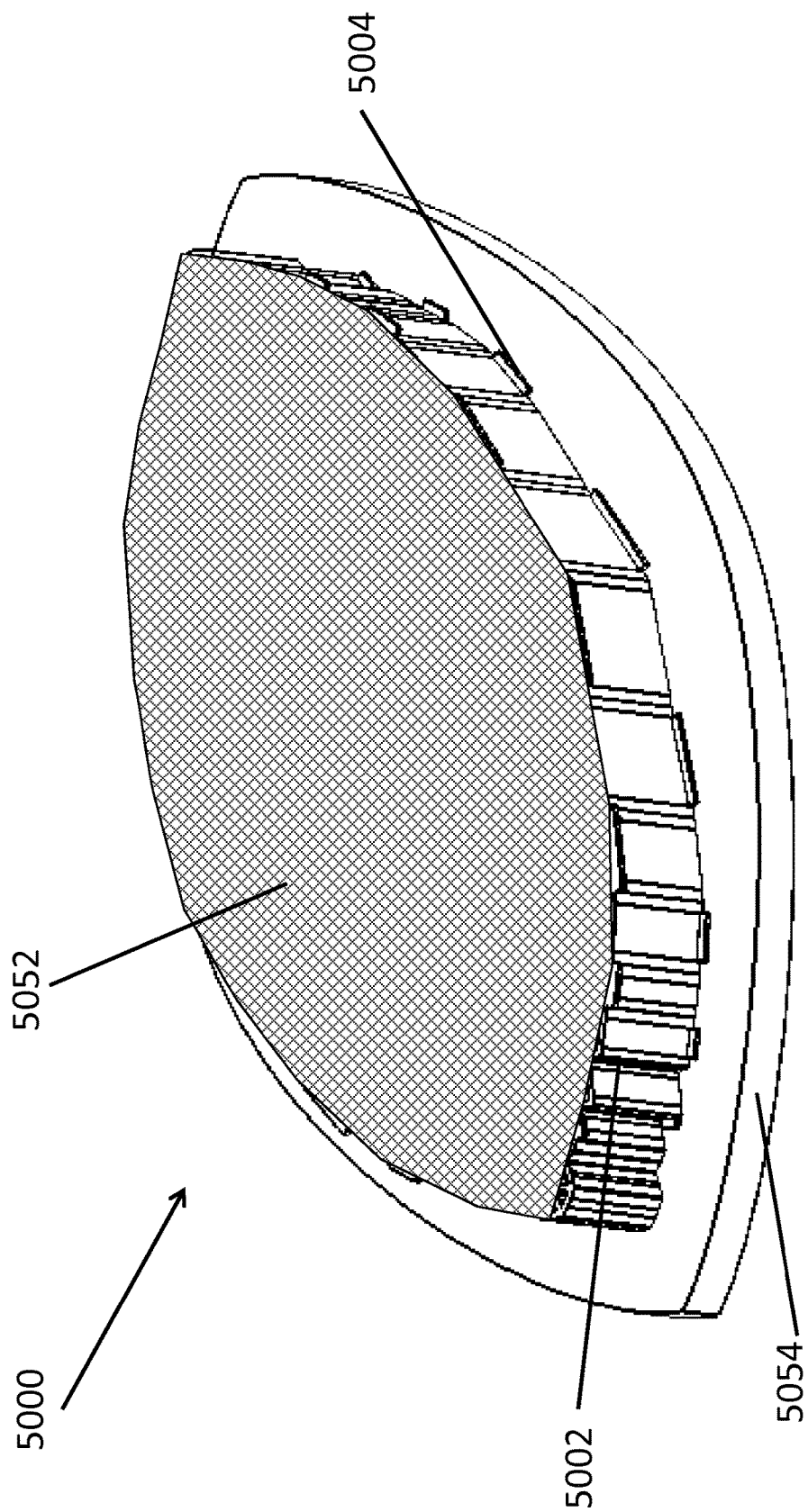

In some embodiments, a wound closure device may include a protective layer 5052, such as a mesh or net layer, in addition to or in place of a foam layer. FIGS. 15A-15B illustrate an embodiment of a wound closure device 5000 including a top layer of mesh or net 5052, a stabilizing structure 5002 (similar to the stabilizing structures described in relation to FIGS. 2A-3E and 12-14D) and a bottom layer of foam 5054 (similar to the bottom layer of foam described in relation to FIGS. 14A-D). As will be described in greater detail below, the protective layer 5052 may have a plurality of openings or pores 5053, and may be shaped in any desired manner to conform to the shape of the stabilizing structure 5002.

The protective layer 5052 may advantageously prevent drawing of the drape down into the stabilizing structure 5002 while permitting transmission of negative pressure to the wound site. In some embodiments, the protective layer 5052 may replace the thicker top layer of foam described in relation with FIGS. 14A-D or elsewhere in the specification. The stabilizing structure 5052 beneath the top protective layer 5052 may be visible through openings or pores 5053, such that the clinician can monitor the collapse of the stabilizing structure 5052 and visualize collapse of the cells of the stabilizing structure. Further, the protective layer 5052, or any additional/alternative protective layers (e.g., additional layers of mesh or net) which may be placed anywhere in wound closure devices may advantageously filter wound fluid.

In some embodiments, the protective layer 5052 and/or the bottom layer of foam 5054 may be attached to the stabilizing structure 5002 before placement in the wound. Pre-attachment of layers of protective layer advantageously reduces the number of steps that need to be completed by the clinician. As described elsewhere in the specification, the stabilizing structure 5002 may comprise tabs 5004, which may be located on the top and bottom edges of the stabilizing structure 5002. These tabs advantageously provide a larger surface area for attachment of the protective layer 5052 to the stabilizing structure 5002. Without the tabs, adhesive would necessarily need to be applied to the narrow upper edges of the stabilizing structure, potentially creating a weak or non-existent attachment. In some embodiments, rather than adhesive, the tabs 5004 may be covered in anchors, act much like the adhesive, allowing the protective layer to be attached to the stabilizing structure prior to placement in the wound.

The stabilizing structure 5002 may be pre-attached to the bottom layer of foam 5054, the top protective layer 5052, or both. In certain embodiments, the adhesive may be applied to the central longitudinal elongate member of the stabilizing structure rather than to the tabs or other location. By applying adhesive only to the central elongate member, the stabilizing structure may collapse without resistance from the foam or protective layer. In some embodiments, the mesh or net may be welded to the stabilizing structure, for example around the edge of stabilizing structure.

FIGS. 15A-B show an embodiment of a wound closure device where the top protective layer 5052 conforms to the size and the shape of the stabilizing structure 5002 along its width and length. The protective layer 5052 may be cut or torn from a larger layer (such as a larger layer of mesh or net) to the shape and size of the stabilizing structure 5002. The protective layer 5052 may be cut or torn either before or after the protective layer is attached to the stabilizing structure 5002. In some embodiments, the protective layer 5052 may include perforations or pre-cuts, such that a portion of the protective layer 5052 may be detachable to form a protective layer having smaller size or different shape. In some embodiments, the protective layer 5052 may have multiple detachable portions to better accommodate various shape and size of stabilizing structures.

In some embodiments, the protective layer 5052 may be larger than the stabilizing structure 5002 such that the protective layer partially extends outward from the stabilizing structure 5002. In some embodiments, the portion of the protective layer extending outward from the stabilizing structure may be wrapped around the outer wall of the stabilizing structure, and may be optionally adhered and/or welded to the outer wall of the stabilizing structure. In some embodiments, a portion of the protective layer extending outward from the stabilizing structure may be large enough, such that a portion of the protective layer wraps around the outer wall of the stabilizing structure and cover at least part of the bottom face of the stabilizing structure. The portion covering the bottom face of the stabilizing structure may be placed between the stabilizing structure and the bottom layer of the stabilizing structure. In some embodiments, the stabilizing structure may be fully encased by a layer of protective layer.

FIGS. 15A-B show an embodiment of the wound closure device 5000 where a protective layer such as a mesh or net is placed above the stabilizing structure, but other configurations are also available. For example, the protective layer(s) may be placed below the bottom layer of foam and/or below the stabilizing structure. The wound closure device 5000 may further include a top layer of foam above the top protective layer 5052, and/or between the stabilizing structure 5002 and the top protective layer 5052. In some embodiments, wound closure device may include two or more protective layers. In some embodiments, the protective layers may be integrated into/onto any layers of foam.

Mesh or net layers or other protective layer materials described in this section or elsewhere in the specification may have a variety of opening or pore sizes. For example, a mesh or net layer may have a pore size of at most 10 mm, 5 mm, 3 mm, 1 mm, 0.5 mm, 0.3 mm, 0.1 mm or less than 0.1 mm. In some embodiments, a protective layer may have an average pore size of 1 mm-3 mm. In some embodiments, the pore size may be smaller than the size of cells of the stabilizing structure. In some embodiments, a protective layer may have a substantially uniform pore size. In some embodiments, a protective layer may contain two or more different pore sizes. In some embodiments, a kit may be provided that includes protective layers, such as meshes or nets, of various pore sizes, allowing the clinician to select the appropriate protective layer according to, for example, desired degree of filtering. Pores or openings may have a variety of shapes, for example, diamond, hexagon, circle, or any other suitable shapes.

Any of the protective layers described herein this section or elsewhere in the specification may be constructed from any suitable means. For example, a mesh or net layer may be knitted and/or woven, and/or constructed by molding and/or extrusion. In some embodiments, a mesh or net layer may be printed directly using 3D printing technology.

In certain embodiments, any of the protective layers described herein this section or elsewhere, such as the layer of mesh or net of FIGS. 15A-B may be constructed from a single polymer. In some embodiments, the protective layers may be constructed from one polymer, two polymers, three polymers, or more than three polymers. The protective layers described in this section or elsewhere in the specification may be constructed from any suitable materials described herein this section or elsewhere in the specification, or any type of suitable materials, such as polymers, metals, or fabrics. For example, a mesh or net layer may be a least partially constructed from polyethylene, polypropylene, polystyrene, polyester, or copolymers thereof. In some embodiments, the protective layer may be constructed from two or more different materials. The protective layer may have two or more sub-layers. The protective layer may be constructed from hydrophobic material and/or hydrophilic material. In some embodiments, to avoid collapse of pores, to avoid deformation of the protective layer, and/or to avoid being drawn into the stabilizing structure, the protective layer may be sufficiently rigid and/or resilient. In some embodiments, the protection layer may contain DelStar PT20, SN42, H526 or CB32.

Figure 16A:
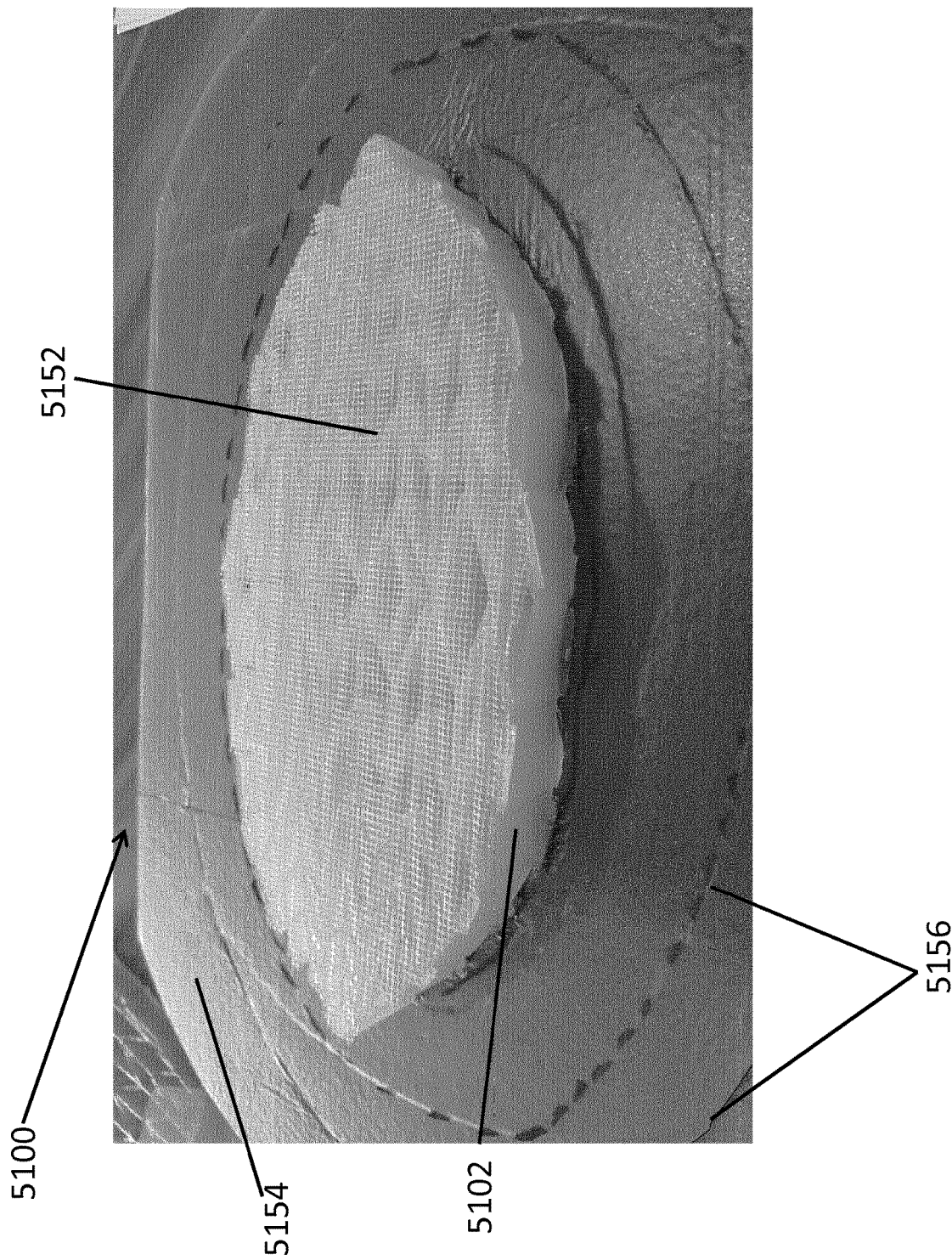
FIGS. 16A-E are photographs of an embodiment of a stabilizing structure with a protective layer and a foam layer.
Figure 16B:
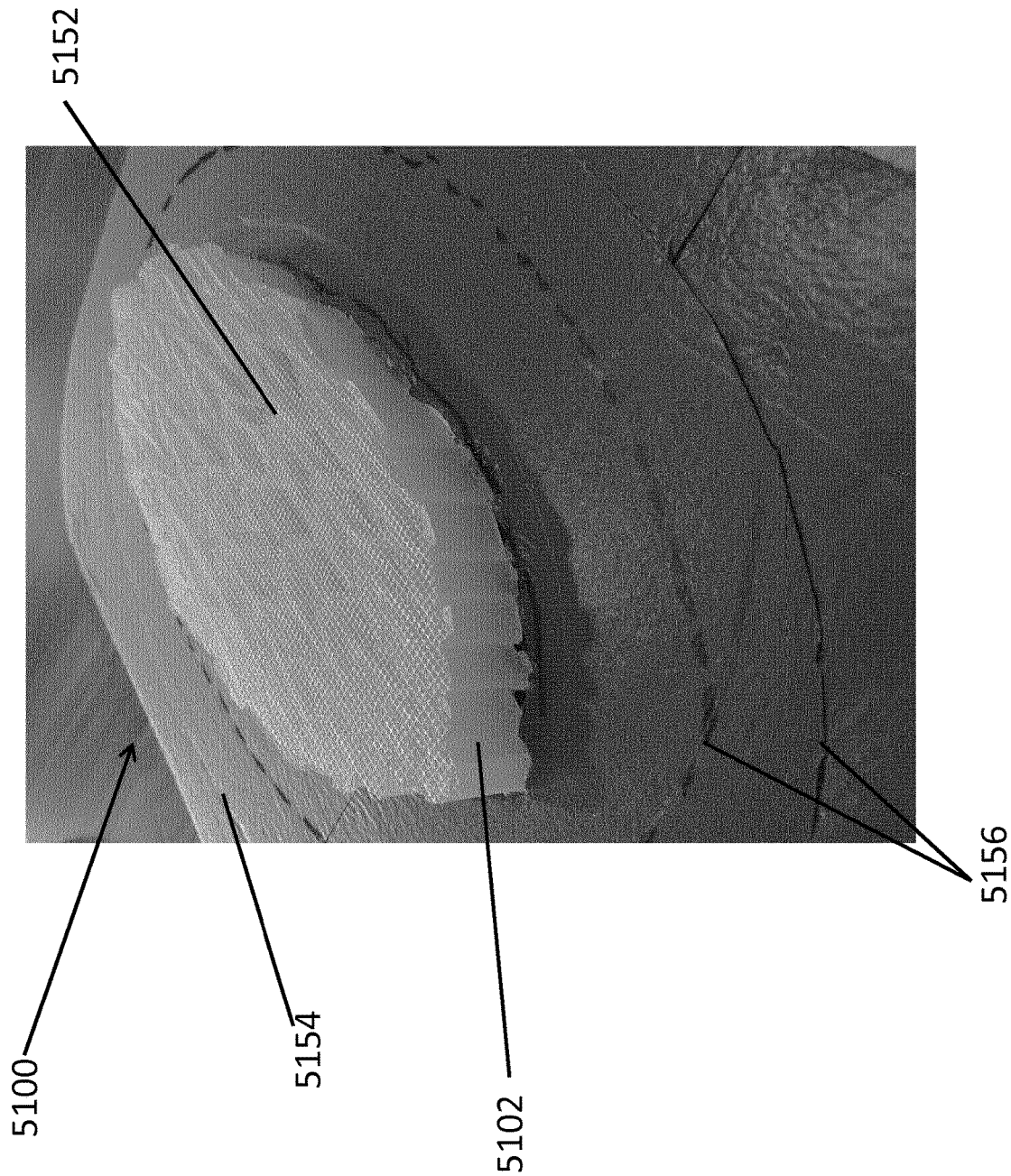
Figure 16C:
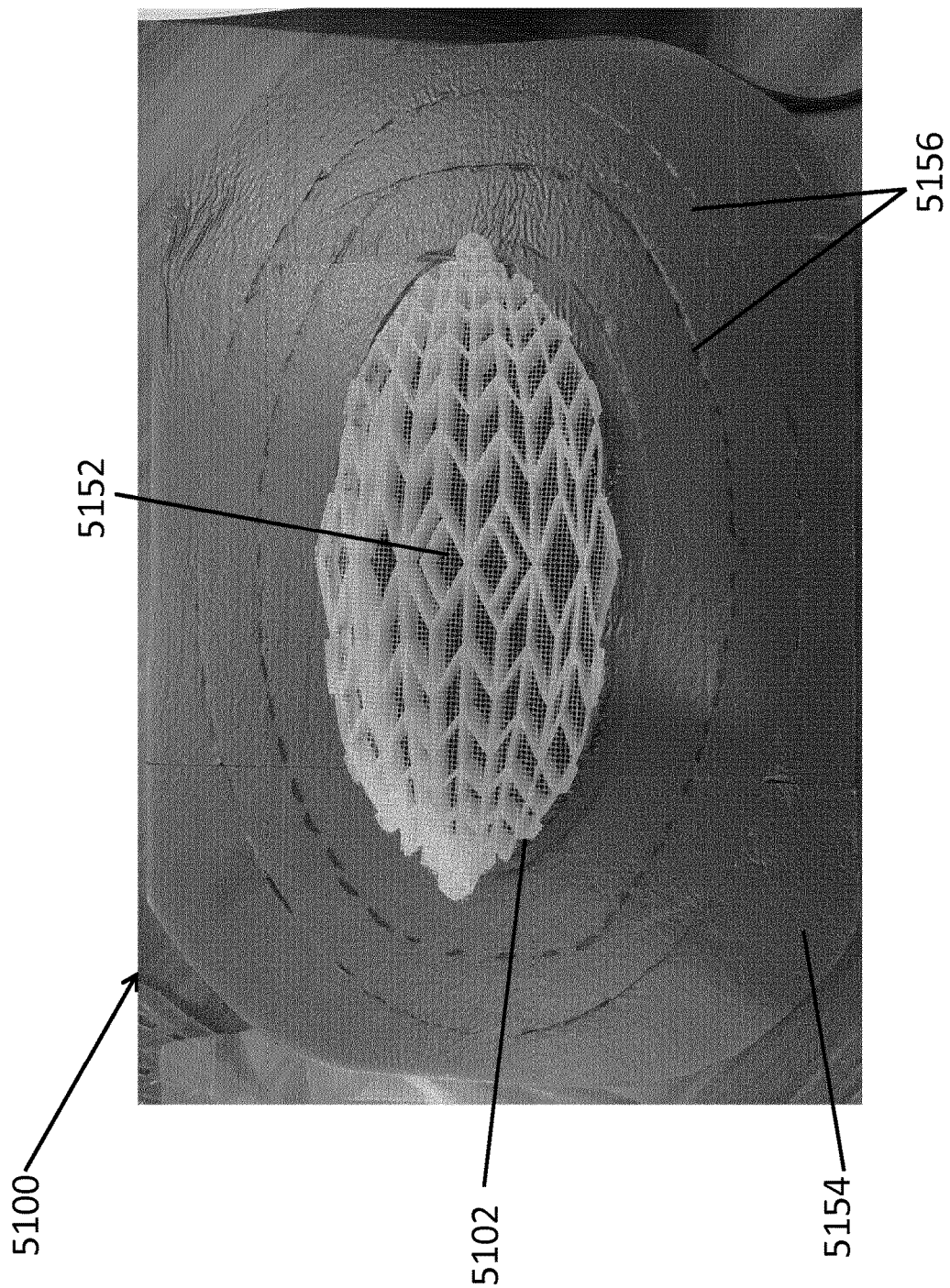
Figure 16D:
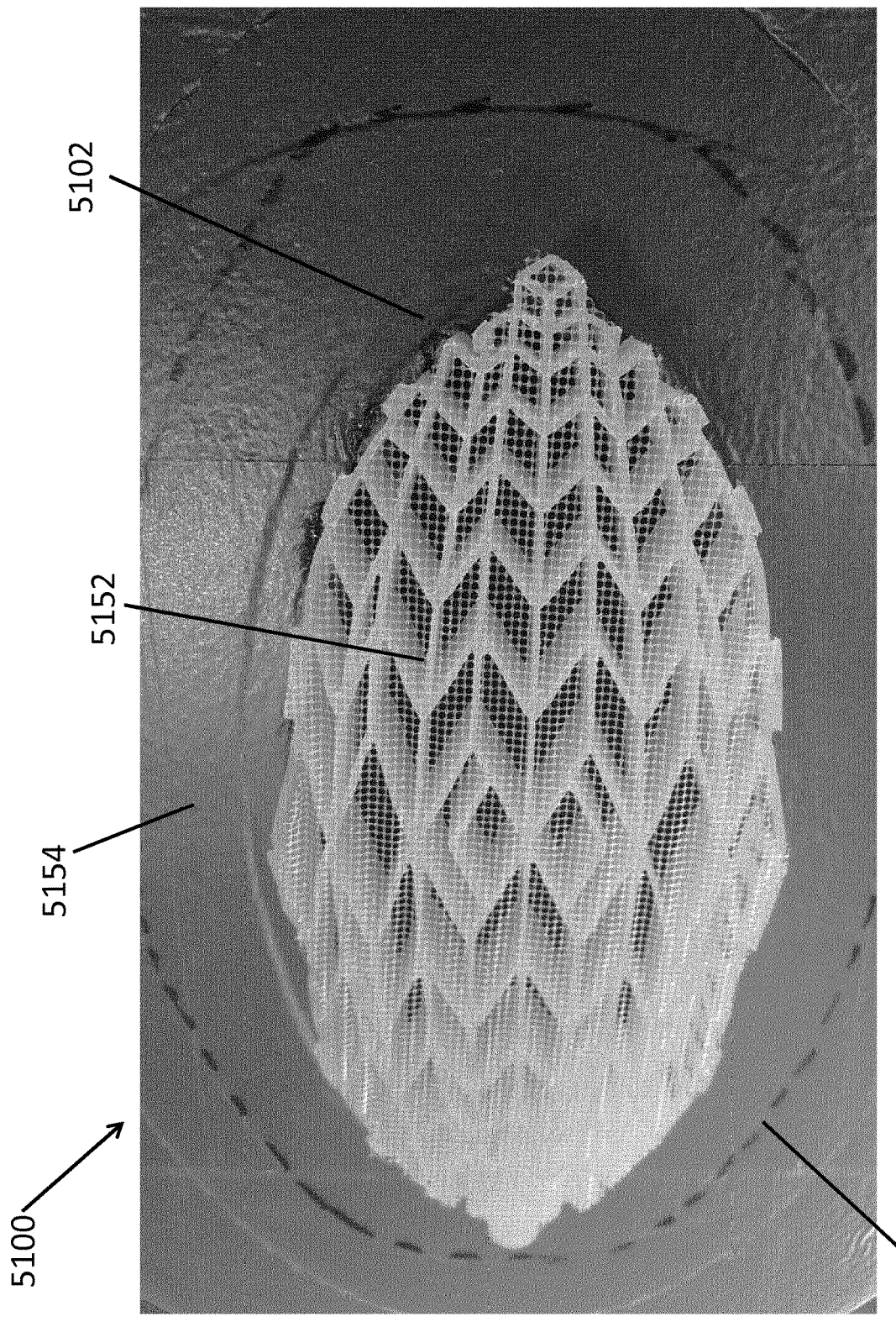
Figure 16E:
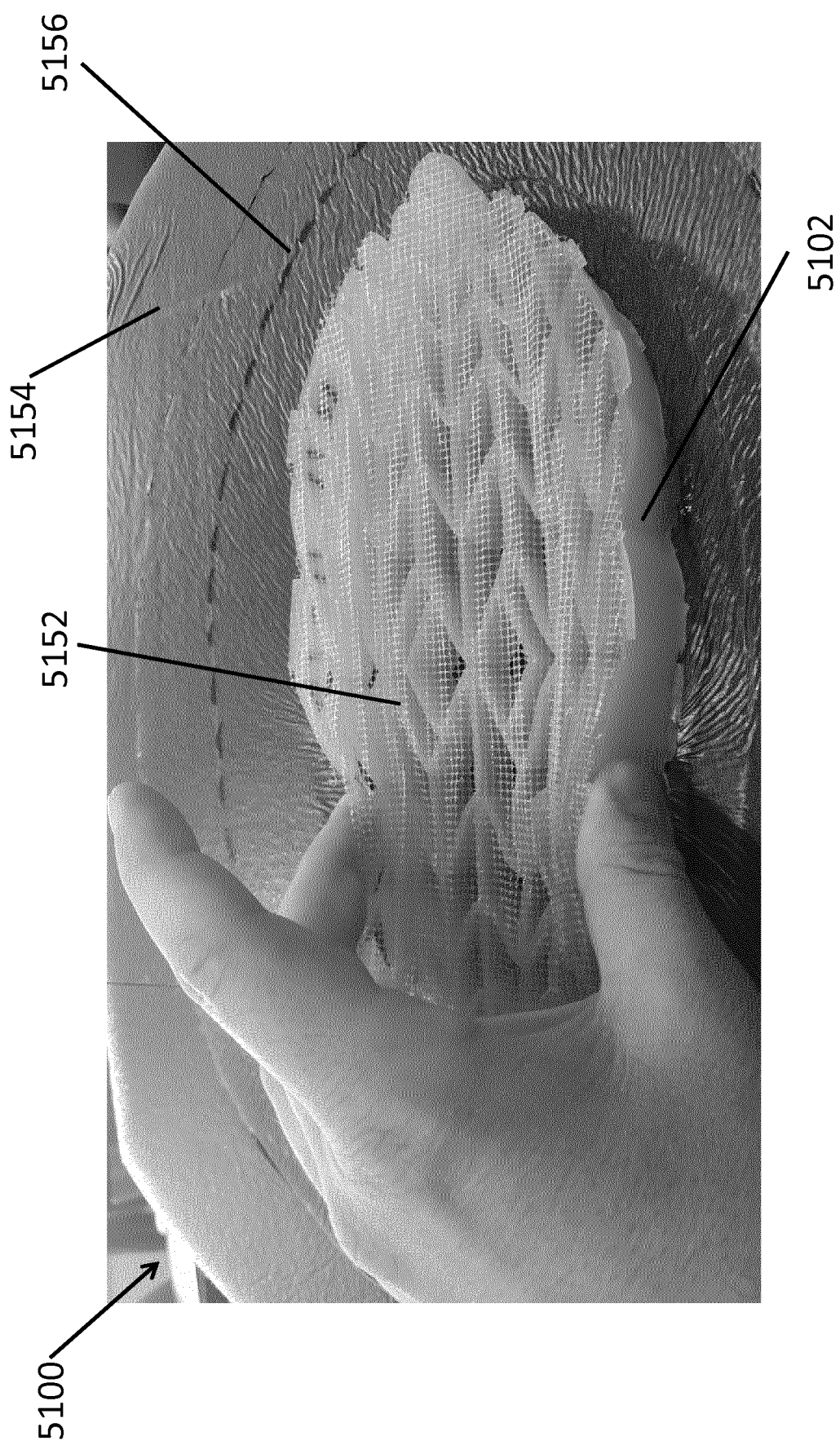

FIGS. 16A-E are photographs of an embodiment of a wound closure device 5100 similar to the wound closure device 5000 of FIGS. 15A-B. The wound closure device 5100 includes a stabilizing structure 5102 (similar to the stabilizing structures described in relation to FIGS. 2A-3E and 12-15B), a top protective layer 5152 shown as mesh or net (similar to the top protective layer described in relation to FIGS. 15A-B), and a bottom layer of foam 5154 (similar to the bottom layer of foam described in relation to FIGS. 14A-15B). Here, the bottom layer of foam 5154 has a greater size relative to the stabilizing structure 5102, than bottom layers of foam described in relation to FIGS. 15A-15B. Such as shown in FIGS. 16A-E, the bottom layer of foam 5154 may include cuts or pre-cuts 5156 defining frangible portions of the foam, such that the bottom layer of foam 5154 may be cut or torn to accommodate to the size and shape of the wound site. Examples of such layers of foam which may be cut or torn applications may be found in U.S. Pat. No. 8,791,315, titled "SYSTEMS AND METHODS FOR USING NEGATIVE PRESSURE WOUND THERAPY TO MANAGE OPEN ABDOMINAL WOUNDS," issued Jun. 29, 2014, which is hereby incorporated by reference in its entirety. The protective layer 5152 may be constructed from a flexible material, such that it does not prevent the collapse of the stabilizing structure 5102, as shown in FIG. 16E.

A wound closure device having a protective layer, such as the wound closure device 5000 of FIGS. 15A-B or the wound closure device 5100 of FIG. 16A-E may be positioned within the wound, for example in similar manner with the wound closure devices described in relation to FIG. 9B or elsewhere in the specification. Also, one or more drapes may be applied over the wound closure device having a stabilizing structure and a protective layer to form a fluid tight seal, for example in similar manner with the method described in relation to FIG. 10, or elsewhere in the specification. When negative pressure is delivered under the drape(s) as described in this section or elsewhere in the specification, the protective layer such as mesh or net described in relation to FIGS. 15A-16E may permit negative pressure to be delivered to the stabilizing structure beneath it through its pores, while preventing the drape from being drawn into the cells of the stabilizing structure. Further, a clinician may visualize the collapse of the cells of the stabilizing structure through the pores of the protective layer.

Other Variations

Although this disclosure describes certain embodiments, it will be understood by those skilled in the art that many aspects of the methods and devices shown and described in the present disclosure may be differently combined and/or modified to form still further embodiments or acceptable examples. All such modifications and variations are intended to be included herein within the scope of this disclosure. Indeed, a wide variety of designs and approaches are possible and are within the scope of this disclosure. No feature, structure, or step disclosed herein is essential or indispensable. Moreover, while illustrative embodiments have been described herein, the scope of any and all embodiments having equivalent elements, modifications, omissions, combinations (e.g., of aspects across various embodiments), substitutions, adaptations and/or alterations as would be appreciated by those in the art based on the present disclosure. While certain embodiments have been described, these embodiments have been presented by way of example only, and are not intended to limit the scope of protection.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:
1. A wound closure device, comprising:
a stabilizing structure for insertion into a wound, the stabilizing structure comprising a top surface and a bottom surface and a plurality of cells extending between the top surface and the bottom surface, the cells configured to allow the stabilizing structure to collapse; and a protective layer positioned directly against the top surface of the stabilizing structure, the protective layer comprising a layer of mesh or a layer of net having a plurality of openings sized and configured to allow visualization of the cells underneath the protective layer;

wherein:
the protective layer is directly attached to the top surface of the stabilizing structure; and
the protective layer is configured to prevent a drape positioned over the stabilizing structure from being drawn into the cells of the stabilizing structure while permitting transmission of negative pressure to the wound site.

2. The wound closure device of claim 1, wherein the protective layer is configured to allow visualization of the cells of substantially the entire stabilizing structure underneath the protective layer.

3. The wound closure device of claim 2, wherein the layer of mesh or net comprises polyethylene.

4. The wound closure device of claim 1, wherein the plurality of openings of the protective layer have a size smaller than the cells.

5. The wound closure device of claim 1, wherein the plurality of openings has average size of 1-3 mm.

6. The wound closure device of claim 1, wherein the protective layer conforms to the shape of the stabilizing structure.

7. The wound closure device of claim 1, further comprising a bottom layer of foam positioned or positionable underneath the stabilizing structure, wherein the bottom layer of foam comprises a lip that is configured to extend outward relative to the stabilizing structure.

8. The wound closure device of claim 7, wherein the bottom layer of foam is attached to the bottom surface of the stabilizing structure.

9. The wound closure device of claim 7, further comprising a middle layer of foam attached to the bottom surface of the stabilizing structure, wherein the middle layer of foam conforms to the shape of the stabilizing structure.

10. The wound closure device of claim 9, wherein the bottom layer of foam is attached to the middle layer of foam.

11. The wound closure device of claim 7, wherein the bottom layer of foam comprises cuts, the cuts defining frangible portions of the foam.

12. The wound closure device of claim 1, wherein the stabilizing structure is configured to collapse more in a horizontal plane parallel to a length and a width of the stabilizing structure than in a vertical plane perpendicular to the horizontal plane.

13. The wound closure device of claim 1, further comprising a drape configured to be positioned over the protective layer and the stabilizing structure to seal to skin surrounding the wound.

14. The wound closure device of claim 13, further comprising a port, wherein the port is configured to transmit negative pressure through the drape.

15. The wound closure device of claim 1, further comprising a source of negative pressure.

16. A method of treating a wound with the wound closure device of claim 1, comprising:
positioning the stabilizing structure within the wound;
applying one or more drapes over the stabilizing structure and the protective layer to create a fluid tight seal; and
delivering negative pressure through or under the one or more drapes to cause collapse of the cells, wherein the protective layer permits the collapse of the cells to be visualized during delivery of negative pressure.

17. The method of claim 16, further comprising cutting the protective layer such that the protective layer conforms to the shape of the stabilizing structure.

18. The method of claim 16, wherein the stabilizing structure is positioned within the wound with a bottom layer of foam attached to a bottom of the stabilizing structure, the bottom layer of foam comprising a lip extending outward of the stabilizing structure and positioned beneath tissue surrounding the stabilizing structure.

19. The method of claim 18, wherein the bottom layer of foam comprises detachable portions, the method further comprising detaching portions of the bottom layer of foam before positioning the bottom layer of foam within the wound.

20. The wound closure device of claim 1, wherein the protective layer is configured to permit a collapse of the stabilizing structure in a horizontal direction.

21. The wound closure device of claim 1, wherein the protective layer comprises the layer of net and the layer of net is knitted and/or woven.

22. The wound closure device of claim 1, wherein the protective layer comprises the layer of net and the layer of net is 3D printed.

23. The wound closure device of claim 1, wherein the protective layer has a size and a shape that matches a size and a shape of the top surface of the stabilizing structure.

24. A wound closure device, comprising:
a stabilizing structure for insertion into a wound, the stabilizing structure comprising a top surface and a bottom surface and a plurality of cells extending between the top surface and the bottom surface, the cells configured to allow the stabilizing structure to collapse in one or more horizontal directions; and
a protective layer positioned against the top surface of the stabilizing structure;
wherein:
the protective layer comprises a top surface and a bottom surface;
the protective layer is directly attached to the top surface of the stabilizing structure;
the protective layer comprises a plurality of openings across substantially the entire top surface, the openings extending through the top and bottom surfaces of the protective layer;
the plurality of openings across substantially the entire protective layer are sized and configured to allow visualization of the cells of substantially the entire stabilizing structure underneath the protective layer;
the protective layer is configured to permit a collapse of the stabilizing structure in a horizontal direction; and
the protective layer is configured to prevent a drape positioned over the stabilizing structure from being drawn into the cells of the stabilizing structure while permitting transmission of negative pressure to the wound site.

25. The wound closure device of claim 1, wherein the protective layer is welded to the stabilizing structure.

26. The wound closure device of claim 1, wherein the protective layer is welded or adhered to the outer wall of the stabilizing structure.

27. The wound closure device of claim 1, wherein the protective layer is attached to the top surface of the stabilizing structure with adhesive applied to a central longitudinal elongate member of the stabilizing structure.

28. The wound closure device of claim 1, wherein the stabilizing structure further comprises tabs on the top surface of the stabilizing structure that provide a larger surface area for attachment of the protective layer to the stabilizing structure, wherein the tabs are covered with adhesive or anchors to adhere to the protective layer.

\* \* \* \* \*